United States Patent
McDonald et al.

(10) Patent No.: US 10,195,174 B2
(45) Date of Patent: Feb. 5, 2019

(54) CARBONIC ANHYDRASE IX-RELATED MARKERS AND USE THEREOF

(71) Applicants: SIGNALCHEM LIFESCIENCES CORPORATION, Richmond (CA); BRITISH COLUMBIA CANCER AGENCY, Vancouver (CA)

(72) Inventors: Paul C. McDonald, Coquitlam (CA); Frances E. Lock, Vancouver (CA); Shoukat Dedhar, Richmond (CA)

(73) Assignees: SIGNALCHEM LIFESCIENCES CORPORATION, Richmond (CA); BRITISH COLUMBIA CANCER AGENCY BRANCH, Vancouver (CA)

( * ) Notice: Subject to any disclaimer, the term of this patent is extended or adjusted under 35 U.S.C. 154(b) by 0 days.

(21) Appl. No.: 14/353,665

(22) PCT Filed: Oct. 24, 2012

(86) PCT No.: PCT/US2012/061711
§ 371 (c)(1),
(2) Date: Apr. 23, 2014

(87) PCT Pub. No.: WO2013/063130
PCT Pub. Date: May 2, 2013

(65) Prior Publication Data
US 2014/0303103 A1 Oct. 9, 2014

Related U.S. Application Data

(60) Provisional application No. 61/550,807, filed on Oct. 24, 2011.

(51) Int. Cl.
| | | |
|---|---|---|
| *A61K 31/63* | (2006.01) | |
| *G01N 33/50* | (2006.01) | |
| *A61K 31/337* | (2006.01) | |
| *C12Q 1/6886* | (2018.01) | |
| *G01N 33/574* | (2006.01) | |
| *A61K 31/7048* | (2006.01) | |

(52) U.S. Cl.
CPC ............ *A61K 31/337* (2013.01); *A61K 31/63* (2013.01); *A61K 31/7048* (2013.01); *C12Q 1/6886* (2013.01); *G01N 33/5011* (2013.01); *G01N 33/5023* (2013.01); *G01N 33/5073* (2013.01); *G01N 33/57484* (2013.01); *G01N 33/57492* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 5,474,796 | A * | 12/1995 | Brennan | ............... 427/2.13 |
| 2004/0146955 | A1 | 7/2004 | Supuran et al. | |
| 2005/0048566 | A1 | 3/2005 | Delisi et al. | |
| 2007/0105133 | A1 * | 5/2007 | Clarke | ............ C12N 5/0693 435/6.12 |
| 2008/0255243 | A1 | 10/2008 | Petricoin et al. | |
| 2009/0123439 | A1 | 5/2009 | Yun et al. | |
| 2010/0311084 | A1 * | 12/2010 | Brower | ............ G01N 33/5091 435/7.23 |
| 2010/0317533 | A1 | 12/2010 | Lou et al. | |
| 2011/0171633 | A1 | 7/2011 | Cowens et al. | |

FOREIGN PATENT DOCUMENTS

| | | |
|---|---|---|
| JP | 2010-178650 A | 8/2010 |
| WO | 2006/056766 A2 | 6/2006 |
| WO | 2008/079269 A2 | 7/2008 |
| WO | 2009/037454 A2 | 3/2009 |

OTHER PUBLICATIONS

Enard et al. (Science 2002 vol. 296 p. 340).*
Cobb et al (Crit Care Med 2002 vol. 30 p. 2711).*
Affymetrix (HGU133 array affymetrix.com).*
"Affymetrix GeneChip Human Genome U133 Array Set HG-U133A," GEO accession: GPL96, public on Mar. 11, 2002, 511 pages.
Dontu et al., "In vitro propagation and transcriptional profiling of human mammary stem/progenitor cells," *Genes & Development* 17:1253-1270, 2003.
Hwang-Verslues et al., "Multiple Lineages of Human Breast Cancer Stem/Progenitor Cells Identified by Profiling with Stem Cell Markers," *PLoS One* 4(12):e8377, Dec. 2009, 11 pages.
Lock et al., "Targeting carbonic anhydrase IX depletes breast cancer stem cells within the hypoxic niche," *Oncogene* 32:5210-5219, 2013.
Lou et al., "Epithelial-Mesenchymal Transition (EMT) Is Not Sufficient for Spontaneous Murine Breast Cancer Metastasis," *Developmental Dynamics* 237:2755-2768, 2008.
Lou et al., "Targeting Tumor Hypoxia: Suppression of Breast Tumor Growth and Metastasis by Novel Carbonic Anhydrase IX Inhibitors," *Cancer Res* 71(9):3364-3376.
Pacchiano et al., "Ureido-Substituted Benzenesulfonamides Potently Inhibit Carbonic Anhydrase IX and Show Antimetastatic Activity in a Model of Breast Cancer Metastasis," *J. Med. Chem.* 54:1896-1902, 2011.
Ponti et al., "Isolation and In vitro Propagation of Tumorigenic Breast Cancer Cells with Stem/Progenitor Cell Properties," *Cancer Res* 65(13):5506-5511, Jul. 1, 2005.

(Continued)

*Primary Examiner* — Katherine D Salmon
(74) *Attorney, Agent, or Firm* — Seed IP Law Group LLP

(57) ABSTRACT

The present disclosure provides methods for detecting the presence of a cancer stem cell and their use in cancer prognosis, evaluating risk of cancer metastasis, identifying or validating drug candidates, and determining treatment efficacy. It also provides kits useful for detecting the presence of cancer stem cells as well as methods of treating cancer using CAIX inhibitors.

23 Claims, 39 Drawing Sheets

(56) References Cited

OTHER PUBLICATIONS

Stingl et al., "Characterization of bipotent mammary epithelial progenitor cells in normal adult human breast tissue," *Breast Cancer Research and Treatment* 67:93-109, 2001.

Supuran et al., "Carbonic Anhydrase Inhibitors: Aromatic Sulfonamides and Disulfonamides Act As Efficient Tumor Growth Inhibitors," *J. Enzyme Inhibition* 15:597-610, 2000.

Wong et al., "Stemness, cancer and cancer stem cells," *Cell Cycle* 7(23):3622-3624, 2008.

Yip et al., "Disulfiram modulated ROS-MAPK and $NF_\kappa B$ pathways and targeted breast cancer cells with cancer stem cell-like properties," *British Journal of Cancer* 104:1564-1574, 2011.

\* cited by examiner

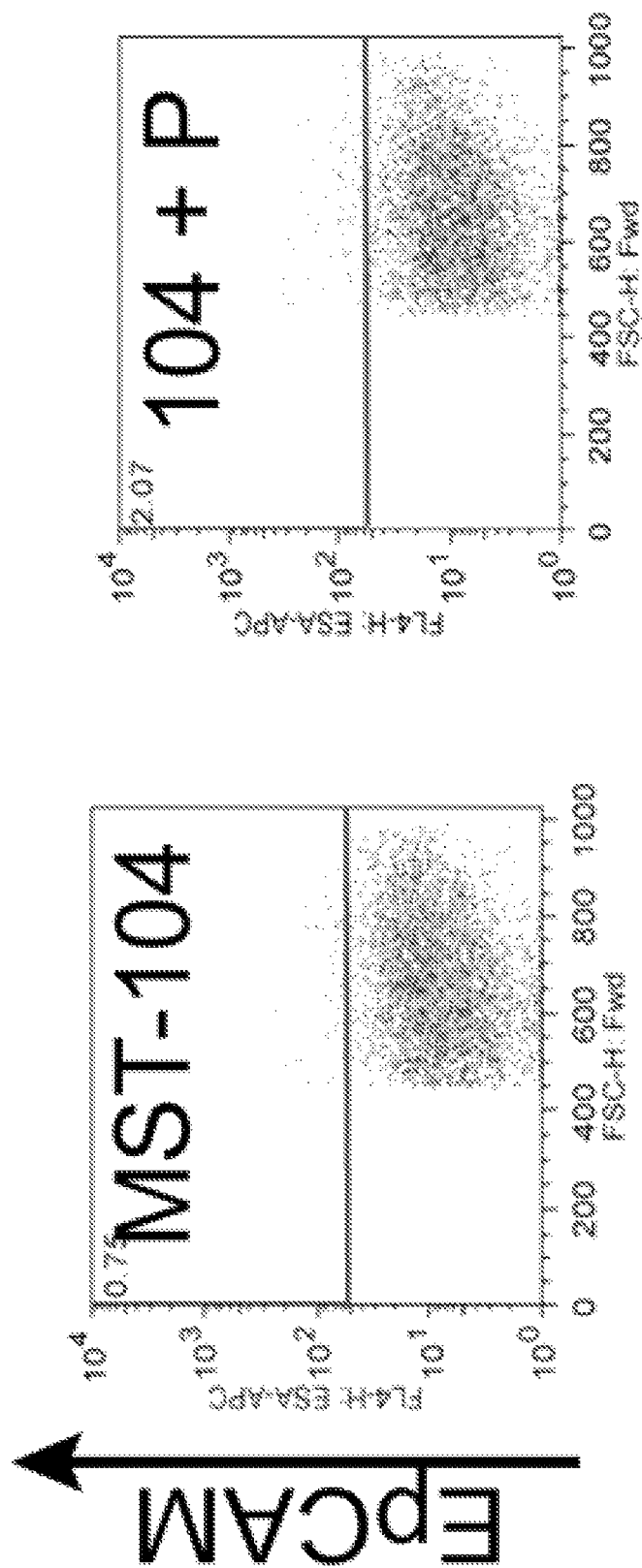

CARBONIC ANHYDRASE IX-RELATED MARKERS AND USE THEREOF

BACKGROUND

Technical Field

The invention lies in the field of cancer stem cell markers and use of such markers in identifying or validating putative cancer therapeutics, detecting cancer stem cells, and treating cancer.

Description of the Related Art

Cancer stem cells (CSCs) are a small, distinct subpopulation of cancer cells within tumors. CSC have stem-like properties including self-renewal and increased clonogenic potential, and divide infrequently to produce daughter stem cells and differentiated tumor cells. CSCs possess the capability to regenerate a tumor, whereas the majority of tumor cells are differentiated and lack this regenerative capability.

CSC are thought to be responsible for patient relapse and metastasis, as they survive conventional treatment, mediating chemotherapy resistance and tumor progression. Hence, only when CSC have been eradicated can a malignancy be effectively "cured".

Tissue oxygen levels play a key role in regulating cancer stem cells in a variety of settings, including the breast. Hypoxia induces expression of hypoxia-response genes, including Carbonic Anhydrase IX (CAIX). This metalloenzyme catalyzes hydration of carbon dioxide to bicarbonate and protons, hence plays an important role in intracellular and extracellular pH regulation.

CAIX is upregulated in hypoxic tumors, including breast malignancies, where it is considered to be a poor prognostic marker for distant metastasis and survival of human breast cancer. In the hypoxic regions of these breast tumors, CAIX activity plays an important role in the survival of tumor cells, through its regulation of tumor pH. CAIX may increase metastatic potential by allowing aggressive tumor cells to survive the hostile environment imposed by hypoxia, facilitating the proliferation and invasion of surviving cells.

Tools for assessing tumors for CAIX pathway involvement, in order to identify whether a given patient or tumor will be susceptible to CAIX inhibition as a treatment, and to monitor treatment progress, could be of immense value to the medical community in treating tumors.

BRIEF SUMMARY

The present disclosure provides the following embodiments:

1. A method for identifying or validating a putative cancer therapeutic, comprising:
   (a) exposing cancer cells to a putative cancer therapeutic to obtain treated cancer cells,
   (b) measuring, of the treated cells, levels of at least three markers, wherein each of the at least three markers is from a different type of markers, the different types of markers being selected from:
   (1) cancer stem cell markers,
   (2) epithelial-mesenchymal transition (EMT) markers selected from mesenchymal markers and epithelial markers,
   (3) stemness markers,
   (4) mTORC1 markers, and
   (5) chemokine markers;
   (c) comparing the level of each of the at least markers measured in step (b) with a reference level for each of the at least three markers;
   wherein a decrease in the levels of cancer stem cell markers, mesenchymal markers, stemness markers, mTORC1 markers, and chemokine markers if measured in step (b) and an increase in the levels of epithelial markers if measured in step (b) indicate that the putative cancer therapeutic is effective in treating cancer.

2. The method of embodiment 1, wherein the cancer stem cell marker is CAIX, EpCAM, ALDH1A3, CD44, ESA, or CD133.

3. The method of embodiment 1 or 2, wherein the mesenchymal maker is smooth muscle actin, Snail-1, Snail-2, Wnt5B, Goosecoid, Zeb2, FoxC2, or p23.

4. The method of any of embodiments 1 to 3, wherein the epithelial marker is E-Cadherin or Desmoplakin.

5. The method of any of embodiments 1 to 4, wherein the stemness marker is Notch 1 or Jagged 1.

6. The method of any of embodiments 1 to 5, wherein the mTORC1 marker is mTOR, Raptor, 4EBP1 or TSC2.

7. The method of any of embodiments 1 to 6, wherein the chemokine marker is RANTES, PIGF, G-CSF, CXCR3, or CXCL10.

8. The method of any of embodiments 1 to 7, wherein the levels of at least 5 markers selected from cancer stem cell markers, mesenchymal markers, epithelial markers, stemness markers, mTORC1 markers and chemokine markers are measured.

9. The method of any of embodiments 1 to 8, wherein step (a) comprises measuring the expression level of one or more of the at least three markers.

10. The method of embodiment 9, wherein the expression level is the level of gene transcription expression.

11. The method of embodiment 9, wherein the expression level is the level of protein expression.

12. The method of any of embodiments 1 to 8, wherein the at least three markers comprises a chemokine marker, and wherein step (b) comprises measuring the level of the chemokine marker secreted by the treated cells.

13. The method of any of embodiments 1 to 8, wherein step (b) comprises measuring the phosphorylation level of one or more of the at least three markers.

14. The method of any of embodiments 1 to 13, wherein the cancer cells are human cancer cells.

15. The method of any of embodiments 1 to 14, wherein the cancer cells area breast cancer cells, brain cancer cells, colon cancer cells, ovarian cancer cells, pancreas cancer cells, prostate cancer cells, melanoma cells, or multiple myeloma cells.

16. The method of any of embodiments 1 to 15, wherein the putative cancer therapeutic is a CAIX inhibitor.

17. A method for detecting the presence of a cancer stem cell in a population of cells, comprising:
   (a) measuring, of a population of cells, levels of at least three markers, wherein each of the at least three markers is from a different type of markers, the different types of markers being selected from:
   (1) cancer stem cell markers,
   (2) epithelial-mesenchymal transition (EMT) markers selected from mesenchymal markers and epithelial markers,
   (3) stemness markers,
   (4) mTORC1 markers, and
   (5) chemokine markers;

(b) comparing the level of each of the at least three markers measured in step (a) with a reference level for each of the at least three markers measured;

wherein an increase in the levels of cancer stem cell markers, mesenchymal markers, stemness markers, mTORC1 markers, and chemokine markers if measured in step (a) and a decrease in the levels of epithelial markers if measured in step (a) indicate the presence of cancer stem cells in the population of cells.

18. The method of embodiment 17, wherein the cancer stem cell marker is CAIX, EpCAM, ALDH1A3, CD44, ESA, or CD133.

19. The method of embodiment 17 or 18, wherein the mesenchymal maker is smooth muscle actin, Snail-1, Snail-2, Wnt5B, Goosecoid, Zeb2, FoxC2, or p23.

20. The method of any of embodiments 17 to 19, wherein the epithelial marker is E-Cadherin or Desmoplakin.

21. The method of any of embodiments 17 to 20, wherein the stemness marker is Notch 1 or Jagged 1.

22. The method of any of embodiments 17 to 21, wherein the mTORC1 marker is mTOR, Raptor, 4EBP1 or TSC2.

23. The method of any of embodiments 17 to 22, wherein the chemokine marker is RANTES, PlGF, G-CSF, CXCR3, or CXCL10.

24. The method of any of embodiments 17 to 23, wherein the levels of at least 5 markers selected from cancer stem cell markers, mesenchymal markers, epithelial markers, stemness markers, mTORC1 markers and chemokine markers are measured.

25. The method of any of embodiments 17 to 24, wherein step (a) comprises measuring the expression level of one or more of the at least three markers.

26. The method of embodiment 25, wherein the expression level is the level of gene transcription expression.

27. The method of embodiment 25, wherein the expression level is the level of protein expression.

28. The method of any of embodiments 17 to 24, wherein the at least three markers comprises a chemokine marker, and wherein step (a) comprises measuring the level of the chemokine marker secreted by the population of cells.

29. The method of any of embodiments 17 to 24, wherein step (a) comprises measuring the phosphorylation level of one or more of the at least three markers.

30. The method of any of embodiments 17 to 29, wherein the population of cells is from a human biological sample.

31. The method of any of embodiments 17 to 30, wherein the cancer stem cell is a breast cancer stem cell, a brain cancer stem cell, a colon cancer stem cell, an ovarian cancer stem cell, a pancreas cancer stem cell, a prostate cancer stem cell, a melanoma stem cell, or a multiple myeloma stem cell.

32. The method of any of embodiments 17 to 30, wherein the population of cells is from a cancer patient after a cancer treatment.

33. A method for treating cancer, comprising:
(a) detecting the presence of a cancer stem cell in a cancer sample according to any of embodiments 17 to 32, wherein the population of cell is from the cancer sample, and
(b) if a cancer stem cell is detected in the cancer sample, administering to the patient an effective amount of a CAIX inhibitor.

34. A method for treating cancer, comprising: administering to the patient an effective amount of a CAIX inhibitor, wherein the patient has been diagnosed to contain cancer stem cells according to any of embodiments 17 to 32.

35. The method of embodiment 33 or embodiment 34, wherein the CAIX inhibitor is MST-104 or MST-205.

36. The method of any of embodiments 33 to 35, further comprising administering an effective amount of taxane to the patient.

37. The method of embodiment 36, wherein the taxane is paclitaxel.

38. A kit comprising protein-binding molecules having specific binding affinity for at least three markers, wherein each of the at least three markers is from a different type of markers, the different types of markers being selected from:
(1) cancer stem cell markers,
(2) epithelial-mesenchymal transition (EMT) markers selected from mesenchymal markers and epithelial markers,
(3) stemness markers,
(4) mTORC1 markers, and
(5) chemokine markers.

39. The kit of embodiment 38, wherein the cancer stem cell marker is CAIX, EpCAM, ALDH1A3, CD44, ESA, or CD133.

40. The kit of embodiment 38 or 39, wherein the mesenchymal maker is smooth muscle actin, Snail-1, Snail-2, Wnt5B, Goosecoid, Zeb2, FoxC2, or p23.

41. The kit of any of embodiments 38 to 40, wherein the epithelial marker is E-Cadherin or Desmoplakin.

42. The kit of any of embodiments 38 to 41, wherein the stemness marker is Notch 1 or Jagged 1.

43. The kit of any of embodiments 38 to 42, wherein the mTORC1 marker is mTOR, Raptor, 4EBP1 or TSC2.

44. The kit of any of embodiments 38 to 43, wherein the chemokine marker is RANTES, PlGF, G-CSF, CXCR3, or CXCL10.

45. The kit of any of embodiments 38 to 44, comprising protein-binding molecules having specific binding affinity for at least 5 markers selected from cancer stem cell markers, mesenchymal markers, epithelial markers, stemness markers, mTORC1 markers, and chemokine markers.

46. The kit of any of embodiments 38 to 45, wherein the kit comprises an array to which the protein-binding molecules are attached.

47. A kit comprising oligonucleotide primers or probes specific for at least three markers, wherein each of the at least three markers is from a different type of markers, the different types of markers being selected from:
(1) cancer stem cell markers,
(2) epithelial-mesenchymal transition (EMT) markers selected from mesenchymal markers and epithelial markers,
(3) stemness markers,
(4) mTORC1 markers, and
(5) chemokine markers.

48. The kit of embodiment 47, wherein the cancer stem cell marker is CAIX, EpCAM, ALDH1A3, CD44, ESA, or CD133.

49. The kit of embodiment 47 or 48, wherein the mesenchymal maker is smooth muscle actin, Snail-1, Snail-2, Wnt5B, Goosecoid, Zeb2, FoxC2, or p23.

50. The kit of any of embodiments 47 to 49, wherein the epithelial marker is E-Cadherin or Desmoplakin.

51. The kit of any of embodiments 47 to 50, wherein the stemness marker is Notch 1 or Jagged 1.

52. The kit of any of embodiments 47 to 51, wherein the mTORC1 marker is mTOR, Raptor, 4EBP1 or TSC2.

53. The kit of any of embodiments 47 to 52, wherein the chemokine marker is RANTES, PlGF, G-CSF, CXCR3, or CXCL10.

54. The kit of any of embodiments 47 to 53, comprising oligonucleotide probes or primers specific for at least 5 markers selected from cancer stem cell markers, mesenchymal markers, epithelial markers, stemness markers, mTORC1 markers, and chemokine markers.

55. The kit of any of embodiments 47 to 54, wherein the kit comprises an array to which the oligonucleotide probes are attached.

In the following description, any ranges provided herein include all the values in the ranges. It should also be noted that the term "or" is generally employed in its sense including "and/or" (i.e., to mean either one, both, or any combination thereof of the alternatives) unless the content clearly dictates otherwise. The term "about" when referring to a number or a numerical range means that the number or numerical range referred to is an approximation within experimental variability (or within statistical experimental error), and thus the number or numerical range may vary between 1% and 15% of the stated number or numerical range. Also, as used in this specification and the appended claims, the singular forms "a," "an," and "the" include plural referents unless the content clearly dictates otherwise.

BRIEF DESCRIPTION OF THE DRAWINGS

FIGS. 29A-29E show representative FACS data. NOD-SCID mice mammary fat pad were inoculated with MDA-MB-231 LM2-4 breast cancer cells. Mice were IV dosed with Paclitaxel, or MST-104, or both drugs in combination, or vehicle. At the humane end point, tumours were excised and the viable EpCAM positive population was assessed by FACS.

DETAILED DESCRIPTION

Figure 1:
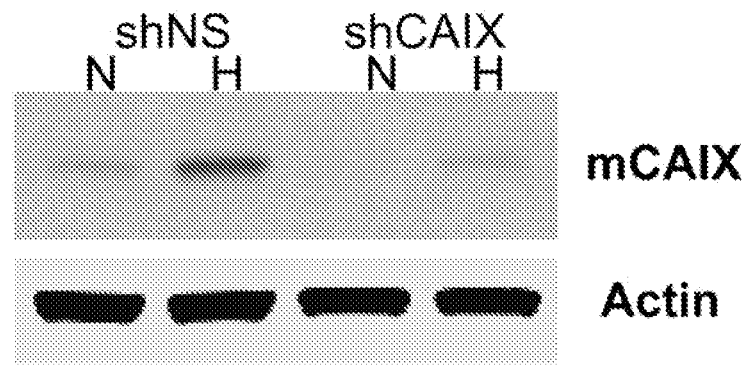
FIG. 1 shows a reproduction of a Western blot of CAIX levels in 4T1-shNS and 4T1-shCAIX cell lines cultured as tumorspheres (TSs) in normoxia or hypoxia. Actin expression levels are shown as a loading control.

The present disclosure provides methods for detecting the presence of a cancer stem cell and their use in cancer prognosis, evaluating risk of cancer metastasis, identifying or validating drug candidates, and determining treatment efficacy. It also provides kits useful for detecting the presence of cancer stem cells as well as methods of treating cancer using CAIX inhibitors.

The present disclosure is based on in part the following discoveries by the present inventors: (1) CAIX is required for expression of certain epithelial-mesenchymal transition (EMT) markers and regulators, expression of stemness markers, and cancer stem cells to expand in hypoxia, (2) the mTORC1 signaling pathway is the critical pathway downstream of CAIX in regulating cancer stem cell function, and (3) CAIX is required for the secretion of chemokines by cancer stem cells in hypoxia. Thus, the present inventors discovered several different types of markers the levels of which are affected by CAIX. Such markers are herein collectively referred to as "CAIX-related biomarkers" or "CAIX-related markers."

Biomarkers

"Biomarker" or "markers," as used herein, refers to a molecule (e.g., genes, mRNAs, or proteins) whose presence, absence, or amount is characteristic of, or required by, a specific cell type or cellular process. "Biomarker," as used herein, may also refer to components of a specific signal pathway or a group of proteins having similar functions and genes or mRNAs encoding the group of proteins.

Gene or protein names and symbols, as used herein, are intended to encompass corresponding genes, mRNA, cDNAs, proteins, or fragments thereof unless otherwise specified.

"Cancer stem cells" (CSCs) are cancer cells found within tumors or hematological cancers capable of giving rise to all cell types found in a particular cancer sample. CSCs are thus tumorigenic (tumor-forming) and may generate tumors through the stem cell processes of self-renewal and differentiation into multiple cell types.

"Cancer stem cell marker" or "cancer stem cell biomarker" refers to a molecule (e.g., genes, mRNAs, or proteins) that is differentially present in cancer stem cells as compared with other cancer cells. A molecule is differentially present in cancer stem cells if the level of the marker in cancer stem cells is statistically different from (e.g., less than or more than) that of other cells (e.g., non-tumorigenic cancer cells or cells that are not cancer cells). Common tests for statistical significance include t-test, ANOVA, Kruska-Wallis, and Wilcoxon.

Different types of cancer may have different cancer stem cell markers. For example, bladder cancer stem cell markers include CD44 and CD47. Breast cancer stem cell markers include aldehyde dehydrogenase I-A1 (ALDH1A1), ALDH1A3, BMI-1, CAIX, CD24, CD44, CD133, CXCR4, DLL4, EpCAM, ErbB2, ESA, GLI-1, GLI-2, IL-1 alpha, IL-6 R alpha, CXCR1, Integrin alpha 6, and PTEN. Colon cancer stem cell markers include ALDH1A1, CD44, CD166, DPPIV/CD26, EpCAM, GLI-1, and Musashi-1. Gastric cancer stem cell markers include CD44 and DLL4. Giloma cancer stem cell markers include A20, ABCG2, CX3CL1, CX3CR1, CXCR4, HIF-2 alpha, Integrin alpha 6, L1CAM, Musashi-1, c-Myc, Nestin, Podoplanin, and IL6 R alpha. Head and neck cancer stem cell markers include ABCG2, ALDH1A1, BMI-1 and CD44. Leukemia cancer stem cell markers include BMI-1, CD34, CD38, CD44, CD47, CD96, GLI-1, GLI-2, IL-3 R alpha, MICL, Musashi-2, SCF R, and TIM-3. Liver cancer stem cell markers include alpha-Fetoprotein, Aminopeptidase N, CD90, and NF2. Lung cancer stem cell markers include ABCG2, ALDH1A1, CD90, EpCAM, and SCF R. Melanoma cancer stem cell markers include ABCB5, ABCG2, ALCAM, MS4A1, Nestin, and NGF R. Myeloma cancer stem cell markers include CD19, CD27, CD38, MS4A1, and Syndecan. Osteosarcoma cancer stem cell markers include ABCG2, Nestin, and STRO-1. Ovarian cancer stem cell markers include alpha-Methylacyl-CoA racemase, CD44, and SCF R. Pancreatic cancer stem cell markers include BMI-1 CD24, CD44, CXCR4, and EpCAM. Prostate cancer stem cell markers include ABCG2, alpha-Methylacyl-CoA racemase, BMI-1, CD44 and c-Myc. In certain preferred embodiments, cancer stem cell markers include CAIX, EpCAM, ALDH1A3, CD44, ESA and CD133.

"Epithelial-mesenchymal transition" (EMT) is a process characterized by loss of cell adhesion, repression of E-cadherin expression, and increased cell motility. EMT promotes CSC migration and invasion, enabling CSC dissemination and metastasis.

"Epithelial-mesenchymal transition biomarker" (EMT biomaker) or "EMT markers" refers to a molecule (e.g., genes, mRNAs, or proteins) the level of which changes during epithelial-mesenchymal transition. An EMT marker may be a mesenchymal marker or an epithelial marker.

"Mesenchymal biomarkers" or "mesenchymal markers" refers to a molecule (e.g., genes, mRNAs, or proteins) that is differentially present in mesenchymal cells compared to other types of cells (e.g., epithelial cells), and the level of which is increased during EMT. Preferred mesenchymal markers include smooth muscle actin, Snail-1, Snail-2 (slug), Wnt5B, Goosecoid, Zeb2, FoxC2, and p23. Additional mesenchymal markers include, twist, TGF-beta 1, osteopontin, type I collagen, matrix metalloproteases (MMP) 2, MMP-3, MMP-9 and Sox10. "Epithelial biomarker" or "epithelial marker" refers to a molecule (e.g., genes, mRNAs, or proteins) that is differentially present in epithelial cells compared to other types of cells (e.g., mesenchymal cells), and the level of which is decreased during EMT. Preferred epithelial markers include E-Cadherin and Desmoplakin. Additional epithelial markers include β-catenin, cytokeratins, desmocollins, desmogleins, claudins and occludin.

"Stemness" is the ability of unspecialized cells to renew themselves as unspecialized cells but still retain the ability to specialize.

"Stemness biomarker" or "stemness marker" refers to a molecule (e.g., genes, mRNAs, and proteins) that are required for maintaining stemness of an unspecialized cell.

Preferred stemness markers include Notch 1 and Jagged 1. Additional stemness markers include Oct 4, Sox2 and Nanog. "mTOR complex 1" (mTORC1) is one of two distinct complexes composed the mammalian target of rapamycin (mTOR). mTORC1 is composed of mTOR, Raptor, GβL (mLST8), PRAS40 and Deptor, and is partially inhibited by rapmycin. mTORC1 integrates multiple signals reflecting the availability of growth factors, nutrients, or energy to promote either cellular growth when conditions are favorable or catabolic processes during stress or when conditions are unfavorable. Growth factors and hormones (e.g., insulin) signal to mTORC1 via Akt, which inactivates TSC2 to prevent inhibition of mTORC1. Alternatively, low ATP levels lead to the AMPK-dependent activation of TSC2 to reduce mTORC1 signaling. Amino acid availability is signaled to mTORC1 via a pathway involving the Rag proteins. Active mTORC1 has a number of downstream biological effects including translation of mRNA via the phosphorylation of downstream targets (4EBP1 and p70 S6 Kinase), suppression of autophagy, ribosome biogenesis, and activation of transcription leading to mitochondrial metabolism or adipogenesis.

"mTORC1 biomarker" or "mTORC1 marker" is a component of mTORC1 signaling pathway or a gene or mRNA encoding the component. Preferred mTORC1 markers include mTOR, Raptor, 4EBP1, and TSC2. Additional mTORC1 markers include PRAS40, ATG13, and p70 S6 Kinase (p70S6K). "Chemokines" refers to a family of small cytokines (small signaling proteins secreted by cells and used extensively in intercellular communication) capable of induce directed chemotaxis in nearby responsive cells. They are small in size (about 8-10 KD) and have 2-6 cysteine residues in conserved locations that are key to forming their 3-dimensional shape.

"Chemokine biomarker" or "chemokine marker" refers to a chemokine or a gene or mRNA encoding the chemokine Preferred chemokine markers include RANTES (CCL5), PlGF, G-CSF, CXCR3 and CXCL10. Additional chemokine markers include CCR1, CCR2, CCR3, CCR4, CCR5, CCR6, CCR7, CCR8, CCR9, CCR10, CCL1, CCL2, CCL3, CCL4, CCL6, CCL7, CCL8, CCL9 (same as CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCR1, CXCR2, CXCR4, CXCR5, CXCR6, CXCR7, CXCL1, CXCL2, CXCL3, CXCL4, CXCL5, CXCL6, CXCL7, CXCL8, CXCL9, CXCL11, CXCL12, CXCL13, CXCL14, CXCL15, CXCL16, CXCL17, XCR1, XCL1, XCL2, $CX_3CR1$ and $CX_3CL1$.

Method for Detecting CSCs

In one aspect, the present disclosure provides a method for detecting the presence of a cancer stem cell in a population of cells using a combination of different types of markers. The method comprises (a) measuring levels of different types of markers, and (b) comparing such levels with reference levels, thereby determining the presence or absence of cancer stem cells in the population of cells. Cancer stem cells are detected if there is a statistically significant increase in the level of a cancer stem cell marker, a mesenchymal marker, a stemness marker, an mTORC1 marker, and/or a chemokine marker, and/or a statistically significant decrease in the level of an epithelial marker compared to the corresponding reference levels of those markers.

The different types of markers that may be used in the method disclosed herein include: (1) cancer stem cell markers, (2) EMT markers, including mesenchymal markers and epithelial markers, (3) stemness markers, (4) mTORC1 markers, and (5) chemokine markers.

The method of the present disclosure may use markers from two or more different types of markers. Preferably, the method use markers from three, four, or five different types of markers provided herein.

The total number of markers used in the method of the present disclosure may be at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25.

In certain embodiments, the markers used in the method of the present disclosure may be at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 markers selected from the group consisting of (1) cancer stem cell markers: CAIX, EpCAM, ALDH1A3, CD44, ESA, and CD133; (2) mesenchymal markers: smooth muscle actin, Snail-1, Smail-2, Wnt5B, Goosecoid, Zeb2, FoxC2, and p23; and epithelial markers: E-Cadherin and Desmoplakin; (3) stemness markers: Notch 1 and Jagged 1; (4) mTORC1 markers: mTOR, Raptor, 4EBP1, and TSC2; and (5) chemokine markers: RANTES, PlGF, G-CSF, CXCR3, and CXCL10.

For example, the method may use at least 3 different markers each of which is of a type different from the types of the other 2 markers. The method may use at least 4 different markers each of which is of a type different from the types of the other 3 markers. The method may use at least 5 markers each of which is of a type different from the types of the other 4 markers. Preferably, the markers are selected from the group consisting of (1) cancer stem cell markers: CAIX, EpCAM, ALDH1A3, CD44, ESA, and CD133; (2) mesenchymal markers: smooth muscle actin, Snail-1, Smail-2, Wnt5B, Goosecoid, Zeb2, FoxC2, and p23; and epithelial markers: E-Cadherin and Desmoplakin; (3) stemness markers: Notch 1 and Jagged 1; (4) mTORC1 markers: mTOR, Raptor, 4EBP1, and TSC2; and (5) chemokine markers: RANTES, PlGF, G-CSF, CXCR3, and CXCL10.

The level of a marker measured according to the method disclosed herein may be the expression level of the marker or the level of a modification of the marker. The expression level may be a gene transcription expression level of the marker or a protein expression level of the marker. The level of a modification of a marker (protein) may be at the level of phosphorylation, glycosylation, nitrosylation, citrullination, or proteolytic processing, of the marker (protein).

Gene transcription expression level of a marker is the amount of mRNA encoding a marker (protein) in cells of interest. Such an amount may be measured by various techniques known in the art, including reverse-transcription PCR (RT-PCR) or real time RT-PCR, a cDNA-based array, an oligonucleoltide array, or a Northern blot hybridization. Exemplary techniques for measuring gene transcription expression levels are also provided in the Examples of the present disclosure.

Protein expression level of a marker is the amount of a marker (protein) in cells of interest or secreted by cells of interest. The amount of a marker (protein) secreted by cells of interest may be determined by measuring the amount of the marker (protein) in serum of a subject from which the cells of interest are obtained. Protein expression level may be measured by various techniques known in the art, including Western blot analysis, ELISA, immunohistochemical analysis, and mass spectrometry analysis. Exemplary techniques for measuring protein expression levels are also provided in the Examples of the present disclosure.

Phosphorylation level of a marker is the amount, the proportion, or the degree of a marker (protein) that has been phosphorylated in cells of interest. Such a level may be measure by various techniques known in the art, including Western blot analysis and electrophoresis and radiography of $P^{32}$ labeled proteins. Exemplary techniques for measuring protein phosphorylation levels are also provided in the Examples of the present disclosure.

The method disclosed herein may be used to detect CSCs in any population of cells suspected to contain cancer cells. Such a cell population may be in vitro cultured cells or may be from a biological sample removed or collected from an animal (e.g., non-human mammals and humans), including tissue biopsies, needle biopsies, blood, lymph, bone marrow, and the like. In certain embodiments, a sample (e.g., blood or serum) other than a cancer tissue biopsie may be obtained from a subject suffering from or suspected to be suffering from a cancer to determine the level of one or more secreted chemokine markers. In certain preferred embodiments, the population of cells of interest is from a hypoxic tumor or malignancy, one or more portions of which are in regions where the oxygen concentration is significantly lower (e.g., 90-95% lower) than in healthy tissues. The method disclosed herein may be used to detect different types of CSCs, including breast, bladder, brain, colon, gastric, hepatic, head and neck, lung, ovarian, osteosarcoma, pancreas, prostate, renal, melanoma and multiple myeloma, leukemia and lymphoma CSCs. Because different types of CSCs may have different CSC markers, it is within ordinary skills to select appropriate CSC markers for detecting a particular type of CSCs. Exemplary CSC markers for various types of cancers are provided above.

After measuring the levels of markers of cells of interest, these levels are compared with a reference level of each of the markers measured. The reference level of a marker may be the level of the marker in reference cells such as normal cells or non-tumorigenic cancer cells, preferably from the same tissue origin. The normal cells or non-tumorigenic cancer cells may be from the same subject from which the population of cells of interest is obtained. Alternatively, these cells may be from another subject or a group of subjects. The other subject or the group of subjects preferably share one or more cancer-related characteristics with the test subject (e.g., same type or subtype of cancer, same or similar tumor grade).

The presence of CSCs in a population of cells may be detected by determining the difference between the level of each marker measured and the reference level of each marker. Cancer stem cells are detected in a population of cells if there is a statistically significant increase in the level of a cancer stem cell marker, a mesenchymal marker, a stemness marker, an mTORC1 marker, and/or a chemokine marker, and/or a statistically significant decrease in the level of an epithelial marker when compared to the corresponding reference levels of those markers. For example, in certain embodiments, 3 markers selected from 3 of the following different types of markers: (1) CSC markers, (2) mesenchymal markers, (3) stemness markers, (4) mTORC1 markers, and (5) chemokine markers are used for detecting CSCs. In such embodiments, CSCs are detected if there is a statistically significant increase in the level of all of the 3 markers measured. In certain other embodiments, an epithelial marker and 2 markers selected from 2 of the other five different types of markers are used to detect CSCs. In such embodiments, CSCs are detected if there is a statistically significant decrease in the level of the epithelial marker and a statistically significant increase in the level of the other 2 markers.

CSCs can be detected if at least 60%, 70%, 80%, or 90% of the markers measured meet the following description: (1) the level of the CSC marker is statistically significantly increased compared to its reference level, (2) the level of the mesenchymal marker is statistically significantly increased compared to its reference level, (3) the level of stemness marker is statistically significantly increased compared to its reference level, (4) the level of mTORC1 marker is statistically significantly increased compared to its reference level, (5) the level of chemokine marker is statistically significantly increased compared to its reference level, and (6) the level of epithelial marker is statistically significantly decreased compared to its reference level. For example, in certain embodiments, 3 or 4 markers out of 5 markers measured meet the above description.

The level of a CSC marker, mesenchymal marker, stemness marker, mTORC1 marker, and/or chemokine marker of CSCs may be at least 2×, at least 3×, at least 4×, or at least 5× of that of reference cells. The level of an epithelial marker of CSCs may be at most 50%, at most 40%, at most 30%, at most 20%, at most 10%, at most 5%, or at most 1% of that of reference cells.

The method disclosed herein may also be used to quantify the amount of CSCs in a population of cells based on the amount of increase in the levels of CSC markers, mesenchymal markers, stemness markers, mTORC1 markers, and/or chemokine markers, and/or the amount of decrease in the levels of epithelial markers compared to their corresponding reference levels.

The method for detecting CSCs may be used in assessing the risk of tumor metastasis. For example, the amount of increase in the levels of CSC markers, mesenchymal markers, stemness markers, mTORC1 markers, and/or chemokine markers, and/or the amount of decrease in the levels of epithelial markers of a test population of cells may be compared to those of a known population of cells with high, moderate, or low metastatic potential. Alternatively, the levels of CSC markers, mesenchymal markers, stemness markers, mTORC1 markers, chemokine markers, and/or epithelial markers of a test population of cells may be directly compared with those of a known population of cells with high, moderate, or low metastatic potential. Such comparisons are helpful in determining the risk of metastasis of the cancer from which the test population of cells is obtained. For example, if the levels of markers of the test population are closer to a known population of cells with high metastatic potential than to a known population of cells with moderate or low metastatic potential, the test population is likely to be highly metastatic.

"High metastatic potential" refers to a propensity to form distant metastasis or metastasis to multiple sites or organs. An exemplary cell line with high metastatic potential is the 4T1 cell line.

"Moderate metastatic potential" refers to a propensity to form local, tissue- or organ-specific metastasis. An exemplary cell line with moderate metastatic potential is the 66c14 cell line.

"Low metastatic potential" refers to a low or no propensity of metastasizing. An exemplary cell line with low metastatic potential is the NR67 cell line.

The method for detecting the presence of CSCs may also be used in cancer diagnosis or prognosis. For example, such a method may be used to determine tumor grade or tumor sub-type or predict likelihood of tumor recurrence. In addition, by detecting and/or quantifying CSCs in a biological sample obtained from a subject at different time points using the method disclosed herein, one may monitor or predict disease progression of cancer in the subject.

Method for Identifying or Validating Drug Candidates

In another aspect, the present disclosure provides a method for identifying or validating a putative cancer therapeutic. The method comprises (a) exposing cancer cells to a putative cancer therapeutic to obtain treated cancer cells, (b) measuring levels of different types of markers, and (c) comparing such levels with reference levels, thereby identifying or validating the putative cancer therapeutic. A putative cancer therapeutic is identified or validated if after exposing cancer cells to the putative cancer therapeutic, there is a statistically significant decrease in the level of a cancer stem cell marker, a mesenchymal marker, a stemness marker, an mTORC1 marker, and/or a chemokine marker, and/or a statistically significant increase in the level of an epithelial marker when compared to the corresponding reference levels of those markers.

Cancer cells to which a putative cancer therapeutic is exposed may be in vitro cultured cancer cells, such as those of cell lines derived from cancer cells. Preferred in vitro cultured cancer cells are those capable of forming tumorspheres, such as cells of the murine breast cancer cell line 4T1. Additional cancer cell lines useful in identifying or validating a cancer drug candidate would include the mouse breast cancer cell line 66c14, and human cell lines MDA-MB-231, MDA-231 LM2-4 MDA-MB-468, HT29, HeLa, and A549. Mouse breast cancer cells overexpressing CAIX, including the 67NR/hCAIX cells, may also be used.

Exposing in vitro cultured cancer cells to a putative cancer therapeutic may be performed by any methods for contacting the cancer cells with the putative cancer therapeutic, including culturing or incubating the cells in the presence of the putative cancer therapeutic. In certain preferred embodiments, the cells are cultured in hypoxia. "Hypoxia," as used in this context, refers to an atmosphere having reduced content of oxygen (i.e., 2% or less oxygen, such as 1% of oxygen).

Cancer cells to which a putative cancer therapeutic is exposed may be cancer cells of a subject (including a non-human mammal and a human) having a cancer. Exposing cancer cells to a putative cancer therapeutic may be performed by locally administering the putative therapeutic to cancer cells or systemically administering the putative therapeutic to the subject.

The different types of markers, exemplary markers of each type, various combinations of markers, techniques for measuring various levels of markers described above in connection with a method of detecting the presence of CSCs are also applicable to the method for identifying or validating a putative cancer therapeutic.

After measuring the levels of markers of cells treated with a putative cancer therapeutic, these levels are compared with a reference level of each of the markers measured. For in vitro cultured cancer cells, the reference level of a marker may be the level of the marker of untreated cultured cancer cells of the same cell line as the treated cancer cells. For example, the level of a particular marker (e.g., EpCAM) of cultured 4T1 cells that are not treated with a putative cancer therapeutic may be used as a reference level to compare with the level of this particular marker of cultured 4T1 cells after treated with the putative cancer therapeutic.

For cancer cells from a subject suffering from a cancer, the reference level of a marker may be the level of the marker of cancer cells from the same cancer tissue as the treated cancer cells, but obtained prior to the treatment of the subject with the putative cancer therapeutic. For example, the level of a particular marker (e.g., EpCAM) of breast cancer cells from a patient prior to the treatment with a putative cancer therapeutic may be used as a reference level to compare with the level of this particular marker of breast cancer cells from the same patient after the patient has been treated with the putative cancer therapeutic.

Alternatively, the reference level of a marker may be the level of the marker of cancer cells from the same tissue types as the treated cancer cells, but obtained from another subject or a group of subjects that has not been treated with the putative cancer therapeutic. Preferably, the other subject or the group of subjects shares one or more common cancer-associated characteristics (e.g., same type or subtype of cancer, same or similar tumor grade) as the subject that has been treated with the putative cancer therapeutic.

A putative cancer therapeutic may be identified or validated by determining the difference between the level of each marker measured and the reference level of each marker. A putative cancer therapeutic may be identified or validated if there is a statistically significant decrease in the level of a cancer stem cell marker, a mesenchymal marker, a stemness marker, an mTORC1 marker, and/or a chemokine marker, and/or a statistically significant increase in the level of an epithelial marker of cells treated with the putative cancer therapeutic when compared to the corresponding reference levels of those markers (e.g., the levels of cancer cells without or prior to the treatment with the putative cancer therapeutic). For example, in certain embodiments, 3 markers selected from 3 of the following different types of markers: (1) CSC markers, (2) mesenchymal markers, (3) stemness markers, (4) mTORC1 markers, and (5) chemokine markers are used for detecting CSCs. In such embodiments, a putative cancer therapeutic may be identified or validated if there is a statistically significant increase in the level of all of the 3 markers measured in/of cancer cells treated with the putative cancer therapeutic. In certain other embodiments, an epithelial marker and 2 markers selected from 2 of the other five different types of markers are used to detect identify or validate a putative cancer therapeutic. In such embodiments, a putative cancer therapeutic is identified or validated if there is a statistically significant increase in the level of the epithelial marker and a statistically significant decrease in the level of the other 2 markers in/of cancer cells treated with the putative cancer therapeutic.

A putative cancer therapeutic can be identified or validated if at least 60%, 70%, 80%, or 90% of the markers measured meet the following description: (1) the level of the CSC marker is statistically significantly decreased compared to its reference level, (2) the level of the mesenchymal marker is statistically significantly decreased compared to its reference level, (3) the level of stemness marker is statistically significantly decreased compared to its reference level, (4) the level of mTORC1 marker is statistically significant decreased compared to its reference level, (5) the level of chemokine marker is statistically significantly decreased compared to its reference level, and (6) the level of epithelial marker is statistically significantly increased compared to its reference level. For example, in certain embodiments, 3 or 4 markers out of 5 markers measured meet the above description.

The level of a CSC marker, mesenchymal marker, stemness marker, mTORC1 marker, and/or chemokine marker of cancer cells treated with an identified or validated cancer therapeutic may be at most 50%, at most 40%, at most 30%, at most 20%, at most 10%, at most 5%, or at most 1% of that of cancer cells of the same tissue origin that have not been treated with the cancer therapeutic. The level of an epithelial marker of cancer cells treated with an identified or validated cancer therapeutic may be at least 2×, at least 3×, at least 4×, or at least 5× of that of that of cancer cells of the same tissue origin that have not been treated with the cancer therapeutic The method disclosed herein may be used to identify or validate any putative cancer therapeutics. Exemplary putative cancer therapeutics include small molecules, antibodies, antigen-binding fragment thereof, polypeptides, peptides, hormones, and nucleic acids (e.g., antisense polynucleotides and short interfering RNAs including siRNA, miRNA, and shRNA). Potential therapeutic agents may be identified from libraries or collections of compounds, compositions, or molecules.

As disclosed herein, the present disclosure is based on in part the following discoveries by the present inventors: CAIX is required for expression of epithelial-mesenchymal transition (EMT) markers and regulators, expression of stemness markers, and cancer stem cells to expand in hypoxia, is upstream of the mTORC1 signaling pathway, and is also required for the secretion of chemokines by cancer stem cells in hypoxia. Thus, the markers disclosed herein are especially useful in identifying or validating CAIX inhibitors as cancer therapeutics.

CAIX inhibitors that may be identified as cancer therapeutics include CAIX-specific antibodies, antigen-binding fragments of CAIX-specific antibodies, fusion proteins comprising antigen-binding fragments of CAIX-specific antibodies, small molecule CAIX inhibitors, antisense polynucleotides and short interfering RNAs (e.g., siRNA, miRNA, and shRNA) that interfere, reduce or eliminate expression of a CAIX gene. Exemplary small molecule CAIX inhibitors include those disclosed in WO 2012/021963 and PCT Application No. PCT/IB2011/055312.

In a related aspect, the method for identifying or validating a putative cancer therapeutic disclosed herein may also be used to evaluate the efficacy of a cancer treatment regimen. By monitoring the changes in level of biomarkers of cancer cells from a patient as disclosed herein during the treatment regimen or after the treatment, one may determine whether the cancer treatment regimen is effective in the particular patient. Such determination may then guide the decision on whether to continue the treatment regimen or repeat the treatment regimen.

Method of Treating Cancer

In another aspect, the present disclosure provides a method for treating cancer that comprises (a) detecting the presence of CSCs in a cancer sample from a patient using the biomarkers and methods disclosed herein, and (b) if CSCs are detected in the cancer sample, administering to the patient an effective amount of a CAIX inhibitor.

In a related aspect, the present disclosure provides a method for treating cancer that comprises administering to a cancer patient an effective amount of a CAIX inhibitor, the cancer patient having been diagnosed to contain CSCs using the biomarkers and methods disclosed herein.

As understood by a person skilled in the medical art, the terms, "treat" and "treatment," refer to medical management of a disease, disorder, or condition of a subject (i.e., patient) (see, e.g., Stedman's Medical Dictionary). "Treating cancer" refers to reducing the number of symptoms of cancer, decreasing the severity of one or more symptoms, or delaying cancer progression.

A cancer patient that may be treated using the method disclosed herein may be a patient that has undergone a cancer treatment other than a treatment using a CAIX inhibitor, but the cancer treatment has not eliminated all cancer stem cells in the patient. Treating such a patient with a CAIX inhibitor, which is specifically directed to CSCs, will be more effective and prevent or reduce the risk of cancer recurrence or metastasis.

Any types of cancer of which CSCs may be detected using the biomarkers and methods disclosed herein may be treated using a CAIX inhibitor, including, breast cancer, bladder cancer, brain cancer, colon cancer, gastric cancer, hepatic cancer, head and neck cancer, lung cancer, ovarian cancer, osteosarcoma, pancreatic cancer, prostate cancer, renal cancer, melanoma, multiple myeloma, leukemia, and lymphoma.

CAIX inhibitors that may be identified as cancer therapeutics include CAIX-specific antibodies, antigen-binding fragments of CAIX-specific antibodies, fusion proteins comprising antigen-binding fragments of CAIX-specific antibodies, small molecule CAIX inhibitors, antisense polynucleotides and short interfering RNAs (e.g., siRNA, miRNA, and shRNA) that interfere, reduce or eliminate expression of a CAIX gene. Exemplary small molecule CAIX inhibitors include those disclosed in WO 2012/021963 and PCT Application No. PCT/IB2011/055312. Exemplary monoclonal and polyclonal antibodies directed against CAIX are disclosed in U.S. Pat. No. 7,378,091. Additional exemplary CAIX inhibitors include those disclosed in U.S. Patent Publication Nos. 2004/0146955 and 2008/0095707. Certain exemplary CAIX inhibitors are also disclosed in the Examples of the present disclosure.

A CAIX inhibitor or a pharmaceutical composition that comprises a CAIX inhibitor may be administered orally, topically, transdermally, parenterally, by inhalation spray, vaginally, rectally, or by intracranial injection, or any combination thereof. In some embodiments, a CAIX inhibitor or a pharmaceutical composition comprising the CAIX inhibitor is administered parenterally, such as via subcutaneous, intravenous, intramuscular, or intracisternal injection, or via infusion techniques.

A CAIX inhibitor or a pharmaceutical composition comprising a CAIX inhibitor is administered at a therapeutically effective dose to a patient who has been diagnosed to contain CSCs according to the method disclosed herein. A "therapeutically effective dose" of a specific therapeutic agent refers to that amount of the agent sufficient to result in reducing the severity of, eliminating, or delaying the onset or reoccurrence of one or more symptoms of cancer in a statistically significant manner. Such a dose may be determined or adjusted depending on various factors including the specific therapeutic agents or pharmaceutical compositions, the routes of administration, the subject's condition, that is, stage of the disease, severity of symptoms caused by the disease, general health status, as well as age, gender, and weight, and other factors apparent to a person skilled in the medical art. Similarly, the dose of the therapeutic for treating a disease or disorder may be determined according to parameters understood by a person skilled in the medical art. Optimal doses may generally be determined using experimental models and/or clinical trials. The optimal dose of a CAIX inhibitor may depend upon the body mass, weight, or blood volume of the subject. For example, an amount between 0.01 mg/kg and 1000 mg/kg (e.g., about 0.1 to 1 mg/kg, about 1 to 10 mg/kg, about 10-50 mg/kg, about 50-100 mg/kg, about 100-500 mg/kg, or about 500-1000 mg/kg) body weight (which can be administered as a single dose, daily, weekly, monthly, or at any appropriate interval) of a CAIX inhibitor may be administered.

Also contemplated is the administration of a CAIX inhibitor or a pharmaceutical composition that comprises a CAIX inhibitor in combination with a second agent useful in treating cancer. Exemplary second agents include biological agents (e.g., anti-EGFR antibodies), chemotherapeutics (e.g., taxane, platinum drugs, fluoropyrimidine, cyclophosphamide, alkylating agents, mitotic inhibitors, antibiotics, antimetabolites, and anti-angiogenic agents), and radiotherapy agents. In a preferred embodiment, the second cancer therapeutic is paclitaxel.

In certain embodiments, a CAIX inhibitor and a second cancer therapeutic may be given simultaneously in the same formulation. Alternatively, the second cancer therapeutic may be administered in a separate formulation but concurrently (i.e., given within less than one hour of each other).

In certain embodiments, the second cancer therapeutic may be administered prior to administration of a CAIX inhibitor (i.e., at least one hour prior to treatment with the A CAIX inhibitor). It is also contemplated that the second cancer therapeutic may be administered subsequent to administration of the CAIX inhibitor (i.e., at least one hour after the administration of the CAIX inhibitor).

Kits

In one aspect, the present disclosure provides a kit comprising protein-binding molecules having specific binding affinity for the biomarkers disclosed herein.

In certain embodiments, the kit comprises protein-binding molecules having specific binding affinity for 2, 3, 4, or 5 of the following different types of markers: (1) cancer stem cell markers, (2) EMT markers, including mesenchymal markers and epithelial markers, (3) stemness markers, (4) mTORC1 markers, and (5) chemokine markers. Preferably, the kit comprises protein-binding molecules having specific binding affinity for 3, 4, or 5 different types of markers provided herein.

The total number of markers for which protein-binding molecules having specific binding affinity are included in the kit of the present disclosure may be at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25.

In certain embodiments, the markers for which protein-binding molecules having specific binding affinity are included in the kit of the present disclosure may be at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 markers selected from the group consisting of (1) cancer stem cell markers: CAIX, EpCAM, ALDH1A3, CD44, ESA, and CD133; (2) mesenchymal markers: smooth muscle actin, Snail-1, Smail-2, Wnt5B, Goosecoid, Zeb2, FoxC2, and p23; and epithelial markers: E-Cadherin and Desmoplakin; (3) stemness markers: Notch 1 and Jagged 1; (4) mTORC1 markers: mTOR, Raptor, 4EBP1, and TSC2; and (5) chemokine markers: RANTES, PIGF, G-CSF, CXCR3, and CXCL10.

For example, the kit may comprise protein-binding molecules having specific binding affinity for at least 3 different markers, each of which is of a type different from the types of the other 2 markers. The kit may comprise protein-binding molecules having specific binding affinity for at least 4 different markers each of which is of a type different from the types of the other 3 markers. The kit may comprise protein-binding molecules having specific binding affinity for at least 5 different markers each of which is of a type different from the types of the other 4 markers. Preferably, the markers are selected from the group consisting of (1) cancer stem cell markers: CAIX, EpCAM, ALDH1A3, CD44, ESA, and CD133; (2) mesenchymal markers: smooth muscle actin, Snail-1, Smail-2, Wnt5B, Goosecoid, Zeb2, FoxC2, and p23; and epithelial markers: E-Cadherin and Desmoplakin; (3) stemness markers: Notch 1 and Jagged 1; (4) mTORC1 markers: mTOR, Raptor, 4EBP1, and TSC2; and (5) chemokine markers: RANTES, PlGF, G-CSF, CXCR3, and CXCL10.

"Specifically binds" or "specific binding" refers to a compound, an antibody, or an antigen-binding fragment of an antibody that recognizes and binds a biomarker protein of interest but does not substantially recognize and bind other molecules in a sample that contains the biomarker protein of interest.

In certain embodiments, the kit comprises an array or a microarray to which the protein-binding molecules are attached.

"Array" refers to an arrangement of agents (e.g., protein, antibodies, nucleic acids, or oligonucleotides) in positionally distinct locations on a substrate. In some instances, the agents on the array are spatially encoded such that the identity of an agent can be determined from its location on the array. A "microarray" generally refers to an array in which detection requires the use of microscopic detection to detect complexes formed with agents on the substrate. A "location" on an array refers to a localized area on the array surface that includes agents, each defined so that it can be distinguished from adjacent locations. Typically, each location includes a single type of agent but this is not required.

In a related aspect, the present disclosure provides a kit comprising oligonucleotide primers and/or probes specific for the biomarkers disclosed herein.

An oligonucleotide primer or probe is specific for a biomarker nucleic acid if it specifically hybridizes to the biomarker nucleic acid or its complement thereof without substantially hybridized to other nucleic acids in a sample that contain the biomarker nucleic acid.

In certain embodiments, the kit comprises oligonucleotide primers or probes for 2, 3, 4, or 5 of the following different types of markers: (1) cancer stem cell markers, (2) EMT markers, including mesenchymal markers and epithelial markers, (3) stemness markers, (4) mTORC1 markers, and (5) chemokine markers. Preferably, the kit comprises protein-binding molecules having specific binding affinity for 3, 4, or 5 different types of markers provided herein.

The total number of markers for which oligonucleotide primers and/or probes are included in the kit of the present disclosure may be at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25.

In certain embodiments, the markers for which oligonucleotide primers and/or probes are included in the kit of the present disclosure may be at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 markers selected from the group consisting of (1) cancer stem cell markers: CAIX, EpCAM, ALDH1A3, CD44, ESA, and CD133; (2) mesenchymal markers: smooth muscle actin, Snail-1, Smail-2, Wnt5B, Goosecoid, Zeb2, FoxC2, and p23; and epithelial markers: E-Cadherin and Desmoplakin; (3) stemness markers: Notch 1 and Jagged 1; (4) mTORC1 markers: mTOR, Raptor, 4EBP1, and TSC2; and (5) chemokine markers: RANTES, PlGF, G-CSF, CXCR3, and CXCL10.

For example, the kit may comprise oligonucleotide primers and/or probes for at least 3 different markers, each of which is of a type different from the types of the other 2 markers. The kit may comprise oligonucleotide primers and/or probes for at least 4 different markers each of which is of a type different from the types of the other 3 markers. The kit may comprise oligonucleotide primers and/or probes for at least 5 different markers each of which is of a type different from the types of the other 4 markers. Preferably, the markers are selected from the group consisting of (1) cancer stem cell markers: CAIX, EpCAM, ALDH1A3, CD44, ESA, and CD133; (2) mesenchymal markers: smooth muscle actin, Snail-1, Smail-2, Wnt5B, Goosecoid, Zeb2, FoxC2, and p23; and epithelial markers: E-Cadherin and Desmoplakin; (3) stemness markers: Notch 1 and Jagged 1; (4) mTORC1 markers: mTOR, Raptor, 4EBP1, and TSC2; and (5) chemokine markers: RANTES, PlGF, G-CSF, CXCR3, and CXCL10.

In certain embodiments, the kit comprises an array or a microarry to which the oligonucleotide probes are attached.

The kits provided herein may be used to detect or quantify levels of biomarkers in a biological sample. For example, the kit comprising protein-binding molecules may be used to measure protein expression levels of biomarkers. The kit comprising biomarker-specific primers or probes may be used to measure gene transcription expression levels of biomarkers.

The following examples are for illustration and are not limiting.

EXAMPLES

Abbreviations:
CA (carbonic anhydrase); TS (tumorsphere); NS (non-silencing); EMT (epithelial to mesenchymal transition); FACS (Fluorescence activated cell sorting); EpCAM (epithelial cell adhesion molecule); RNAi (RNA interference); shRNA (small hairpin RNA); shNS (small hairpin non silencing sequence); shCAIX (small hairpin CAIX specific sequence); IF (immunofluorescence)

Materials and Methods

1. Cell Culture

The acquisition, generation and culture of the luciferase expressing mouse breast cancer cell lines 4T1 have been described (Lou, Preobrazhenska et al. 2008). The MDA-MB-231 LM2-4Luc+ cell line was generously provided by Dr. Robert Kerbel (University of Toronto, Canada) and cells were cultured as described previously (Ebos, Lee et al. 2009). All cells were incubated at 37 degrees C. with 5% $CO_2$ in a humidified incubator ("normoxia").

For culture in hypoxia, cells were maintained in 1% $O_2$ and 5% $CO_2$ balanced with N2 at 37 degrees C. in a humidified incubator in a sealed anaerobic workstation. Stable depletion of murine CAIX in 4T1 cells was carried out as described previously (Lou, McDonald et al. 2011).

2. Tumorsphere Culture

Cultured 4T1 cells were grown as monolayers with twice weekly sub-cultivation in DMEM (Gibco) containing 5% fetal bovine serum (FBS) (Sigma). Subsequently, parental, shNS and shCAIX 4T1 were cultured as Tumor Spheres (TSs) in Mammocult™ media (StemCell Technologies, Vancouver, B.C., Canada) as per the manufacturer's instructions (Lock, McDonald et al. 2012). Alternatively, for spinner culture TS growth, monolayer cells were trypsinized and single-cell suspensions were incubated at $2 \times 10^5$ to $4 \times 10^5$ cells/ml in sealed glass spinner culture flasks (Bellco, Vineland, N.J.) under constant rotation, at 150 RPM, 37° C. in DMEM (5% FBS) pre-equilibrated to 5% $CO_2$ as previously described (Oloumi, MacPhail et al. 2000). Cultures were grown for up to 3 weeks. Media was replenished every 3 days. For hypoxic conditions, spinner flasks were gassed continuously for 3 days with 5% $O_2$ and 5% $CO_2$ balanced with N2.

3. Antibodies

FACS antibodies: human EpCAM(CD326)-AlexaFluor 647™ (Biolegend, San Diego, Calif.); mouse-CD24-APC (Biolegend); mouse/human-CD44-PeCy7 (eBioscience, San Diego, Calif.).

IHC antibodies: human CAIX (R&D systems AF2188); ALDH1A3 (# LS-C97464, Lifespan Biosciences).

IF antibodies: CD133-FITC (eBioscience, San Diego, Calif.); E-cadherin (BD Transduction labs #610181), mouse CAIX (R&D systems AF2344); smooth muscle actin (Sigma); Snail (AbCam #ab17732);

4. Flow Cytometric Analyses and Separation

4T1 TSs were incubated with trypsin, washed once in HF buffer (HBSS containing 2% Fetal Bovine Serum), then stained with anti-CD24-APC and anti-CD44-PECy7 using 0.3 µl of antibody per 106 cells in 100 ul HF, and incubated on ice for 10 min. Following incubation, cells were washed once with HF buffer and resuspended in 300 ul HF buffer containing 4',6-diamidino-2-phenylindole (DAPI; final concentration, 1 µg/ml). Cells were separated on an Aria™ cell sorter (BD Biosciences, San Jose, Calif., USA). Live cells were gated on the basis of forward and side scatter, and single cells were gated on the basis of forward scatter and pulse width. Gates were determined by analysis of unstained cells, isotype specific controls, and single stains. The CD44+CD24−/low or CD44+CD24+ cells were not assessed for purity due to the low numbers of cells obtained. The cell counter of the flow cytometers was used to determine cell numbers. Cells were collected into DMEM media or HF buffer.

For in vivo mouse tumor analysis, excised tumors were finely chopped with a razor blade, digested in DMEM containing 10% collagenase/hyaluronidase mixture for 1.5 h at 37° C., then sequentially treated with trypsin-EDTA, dispase and ammonium chloride (reagents from Stem Cell Technologies, as per manufacturer's instructions). Cells were cultured overnight on standard tissue culture dishes in DMEM+10% FBS. For FACS analysis, plated wells were incubated with trypsin and resuspended in HBSS+2% FBS. Cells were blocked with Mouse Fc block (#553142, BD Pharmingen). Antibody staining and cell sorting was performed as above.

5. Immunofluorescence

4T1 cells cultured on glass coverslips were fixed, permeabilised and immunostained as described previously (Turner, Broad et al. 2006). Parental 4T1 spinner culture TSs were collected, and suspended in OCT freezing media on dry ice. Once frozen, 5 to 7 µm sections were prepared using a Cryostar™ HM560 cryostat (Microm International, GmbH, Walldorf, Germany). Frozen sections were air dried for 30 seconds and transferred to 4% paraformaldehyde for fixation for 20 minutes, washed three times in PBS (5 minutes) and permeabilised in 0.2% triton-X-100 (10 minutes). Subsequent immunostaining steps were described previously (Lock and Hotchin 2009).

6. RNA Extraction and Quantitative PCR

FACS sorted cells were cultured for 72 hours and lysed under hypoxic conditions. mRNA extraction was carried out using QIAGEN RNAeasy™ micro kit (Toronto, Ontario, Canada), as per the manufacturer's instructions. Quantitative PCR was carried out with 5 to 10 ng RNA starting material, using a PreAMP $RT^2$ Mouse Epithelial to Mesenchymal Transition (EMT) PCR Array (PAMM-090, Qiagen) on an Applied Biosystems (Foster City, Calif., USA) 7900HT analyser. The relative fold change of gene expression was calculated by using the standard 2-ΔΔct method (Livak and Schmittgen 2001).

7. Pharmacological Inhibitors

For in vivo studies, the CAIX specific inhibitors CAI017 (Supuran 2008),

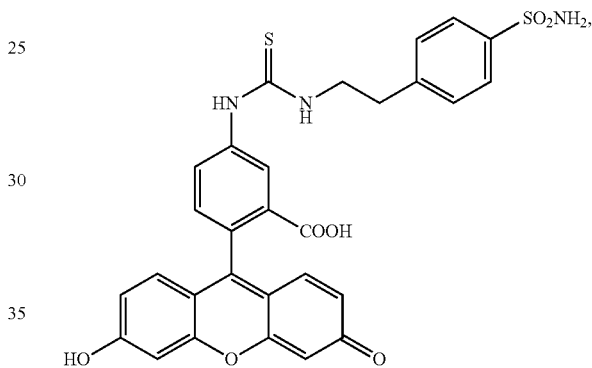

MST-104, a proprietary ureido-sulfonamide with the structure:

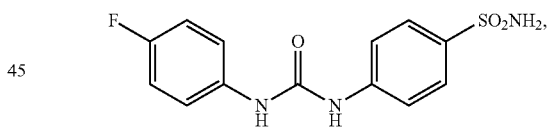

and MST-205, a proprietary glycosylated coumarin 4-methylumbellifer-7-yl-β-L-rhamnopyranoside, with the structure:

MST-205

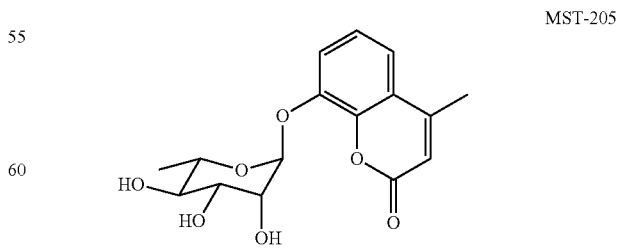

were solubilized and administered as described previously (Lou, McDonald et al. 2011, Supuran 2008). For in vitro studies, CAI017 was added directly to TS culture media at 200 mM, without vehicle. MST-104 was solublised in DMSO and added to culture media at 50 µM, with the same volume of DMSO added to vehicle controls.

8. Mouse Tumor Models

All animal procedures and studies were carried out in accordance with protocols approved by the Institution Animal Care Committee at the BC Cancer Research Centre and the University of British Columbia (Vancouver, BC, Canada). For primary breast tumor xenografts, $2 \times 10^6$ MDA-MB-231 LM2-4Luc+ variant cells were suspended in a 50% Matrigel™/PBS solution and implanted orthotopically in 6-8 week-old female NOD.CB17-prkdcscid/J mice as previously described (Lou, McDonald et al. 2011). Therapy was initiated when tumors reached 200 mm³. Primary tumor growth rates were calculated from caliper measurements using the modified ellipsoid formula (L×W2)/2. Tumor formation and metastasis progression was monitored and quantified using bioluminescent imaging as previously described (Lou, McDonald et al. 2011).

9. Immunohistochemistry

Tumors were harvested, paraffin embedded and tumor sections stained for CAIX (Santa Cruz Biotechnology) as previously described (Lou, McDonald et al. 2011).

10. Statistics

Two-tailed T-tests and descriptive statistics were performed using GraphPad™ software. Unless otherwise stated, error bars represent SEM for a minimum of three independent experiments.

11. RNA Extraction for Analyzing Levels of Chemokine mRNA

4T1-shNS and 4T1-shCAIX cells were seeded to reach 80% confluence the following day. The cells were washed twice with PBS followed by the addition of serum-free media to the cells. The cells were incubated for 24 h in 21% or 1% $O_2$ prior to the media being removed and the cells lysed in their respective $O_2$ tension. mRNA was extracted from lysates using the RNeasy mini-kit (QIAGEN, Toronto, Ontario, Canada) as per the manufacturer's instructions. RNA quantity was determined by Nanodrop and integrity determined by electrophoresis on a 2% agarose gel.

12. cDNA Preparation and Quantitative Real-Time PCR for Chemokine mRNA Analysis 500 ng of total RNA from each sample was used in the preparation of cDNA using the Superscript III First-Strand Synthesis kit (Life Technologies, Carlsbad, Calif., USA). Amplification of the DNA was performed using FAST SYBR Green Master mix real-time qPCR on an Applied Biosystems 7900HT (Foster City, Calif., USA). Quantification of the levels of the individual genes was done using the formula $q=E\hat{}-C_T$, where E represents the primer efficiency and $C_T$ the threshold cycle (Rebollo, Miceli-Royer et al. 2012).

13. Conditioned Media Recovery

4T1-shNS and 4T1-shCAIX cells were grown as described above. After 24 h in their respective $O_2$ tension the media was collected and clarified by centrifugation at 1500 rpm for 5 min at 4° C. The media was filtered through a 0.2 µm syringe filter and stored at −80° C.

14. ELISA

Secreted chemokine levels were assessed from conditioned media using mouse specific CXCL10 and G-CSF Quantikine® ELISA kits (R and D Systems, Minneapolis, Minn., USA) as per the manufacturer's instructions. Conditioned media was normalized based on total protein level.

Example 1

CAIX Expression is Required for Characteristics of Breast Cancer Stem Cells

In vitro proliferation in suspension under serum free conditions as non-adherent tumorspheres has been demonstrated to be a characteristic of breast cancer stem cells (Ponti, Costa et al. 2005).

Figure 2:
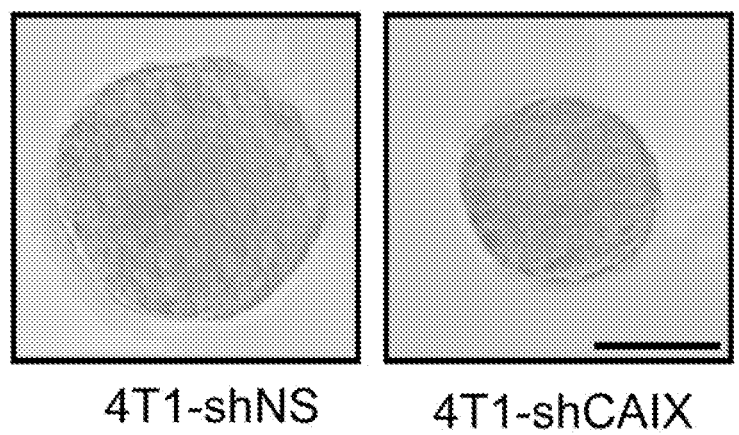
FIG. 2 shows phase contrast micrograph images showing typical 4T1-shNS, or 4T1-shCAIX TSs following 7 days culture in Mammocult™ media. Scale bar=100 µm.

RNA interference (RNAi) was used to stably knock down CAIX expression in the 4T1 mouse breast cancer cell line (4T1-shCAIX), compared to an RNAi non-silencing control (4T1-shNS) (see FIG. 1). 4T1 cells were seeded as single cells and cultured in defined serum-free media using ultralow adherent plates as non-adherent tumorspheres (TS) (FIG. 2). These TS-forming conditions have been shown to promote cancer stem cell growth (Yip, Fombon et al. 2011, Stingl, Eaves et al. 2001, Dontu, Abdallah et al. 2003). Single cell suspensions of 4T1-shNS and 4T1-shCAIX cells were seeded at doubling dilutions and cultured under TS-forming conditions in normoxia (20% oxygen) or hypoxia (1% oxygen) for 7 days.

Figure 3:
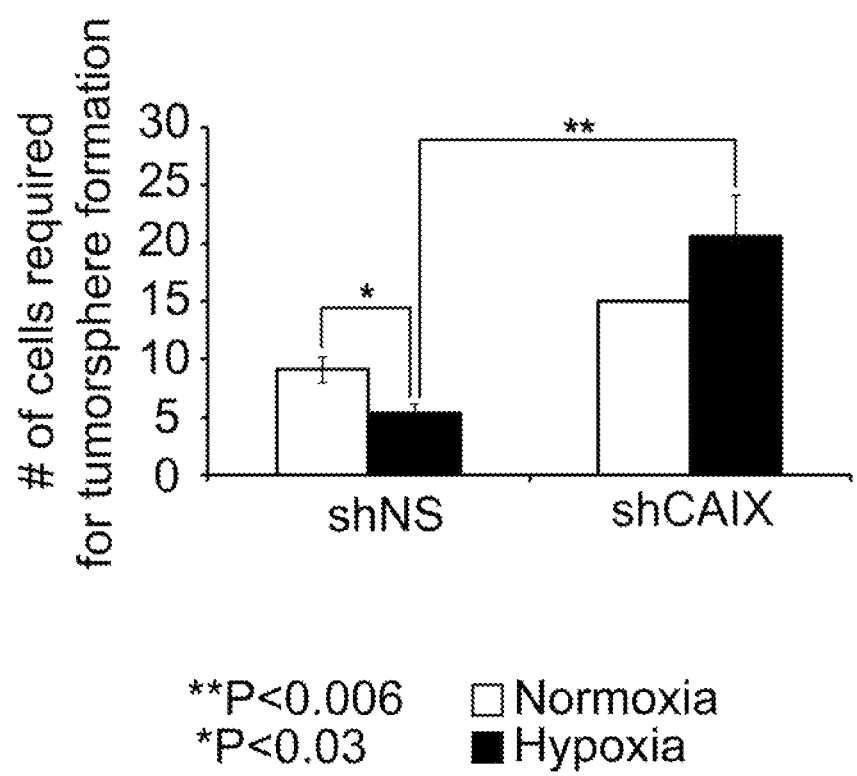
FIG. 3 shows cell numbers required to initiate TS formation under various conditions. 4T1 shNS and shCAIX were seeded at doubling dilutions and cultured under TS-forming conditions in normoxia or hypoxia. Mean±SEM of three independent experiments is shown. Statistical significance was confirmed using T-test, *P<0.03, **P<0.006.

TS-forming ability was assessed as the minimum number of cells required for positive TS growth. No significant difference in the number of cells required to form TSs was observed between shNS-4T1 and shCAIX-4T1 in normoxia). The number of 4T1-shNS cells required to form TSs was significantly reduced in hypoxia (FIG. 3). However, RNAi-mediated knock down of CAIX expression significantly increased the number of seeding cells required to form a TS in hypoxia, suggesting that CAIX expression is required for the CSC expansion in hypoxia observed in control cells (Lock, McDonald et al. 2012).

The CD44+CD24−/low cell signature has previously been described as a breast cancer stem cell population (Ponti, Costa et al. 2005, Al-Hajj, Wicha et al. 2003) and is associated with high risk tumor features and bone marrow metastasis in human patients (Reuben, Lee et al. 2011).

Figure 4:
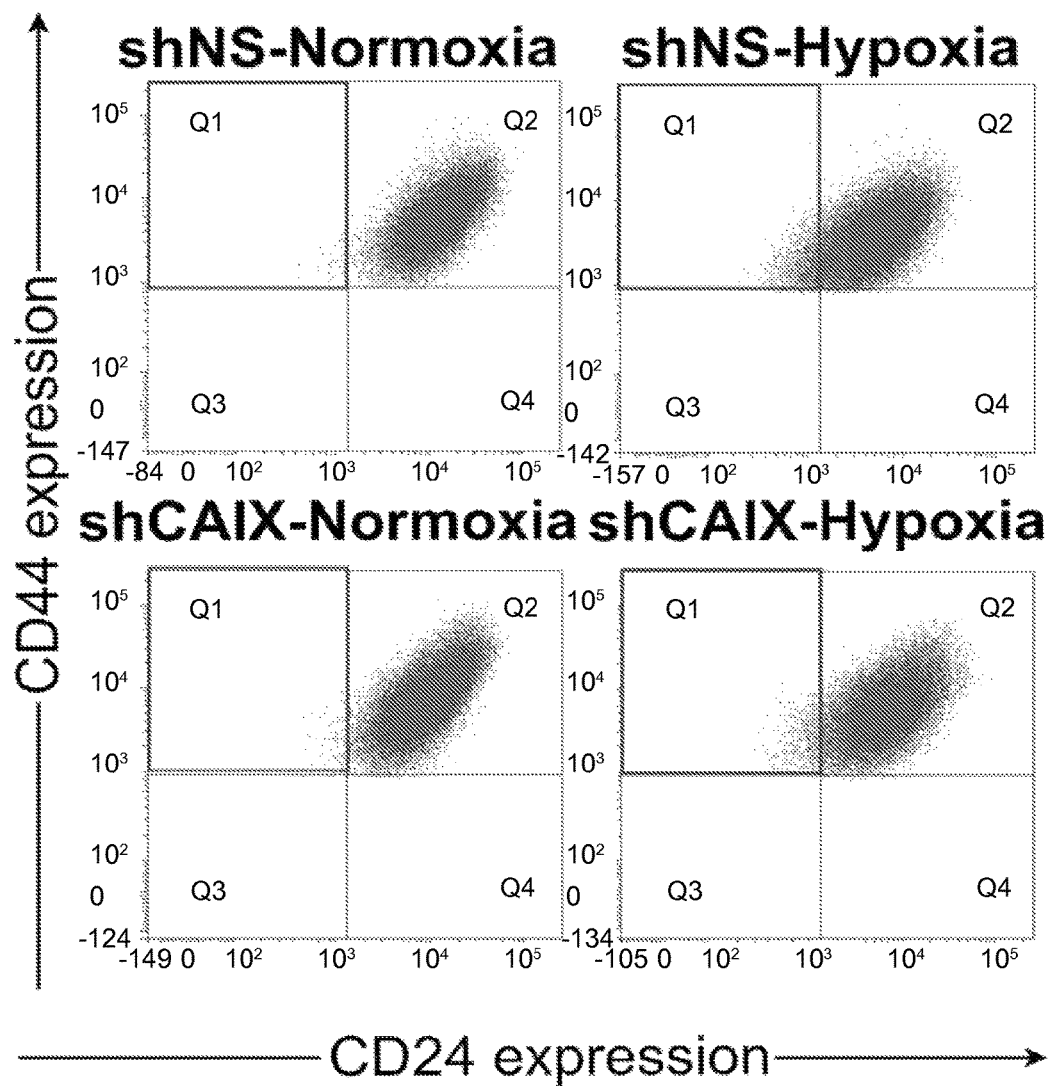
FIG. 4 shows representative FACS plots showing changes in % CD44+CD24−/low cells±SEM. shNS and shCAIX 4T1 cells were cultured as TSs in normoxia or hypoxia, disaggregated and the CD44+CD24−/low population assessed by FACS analysis.
Figure 5:
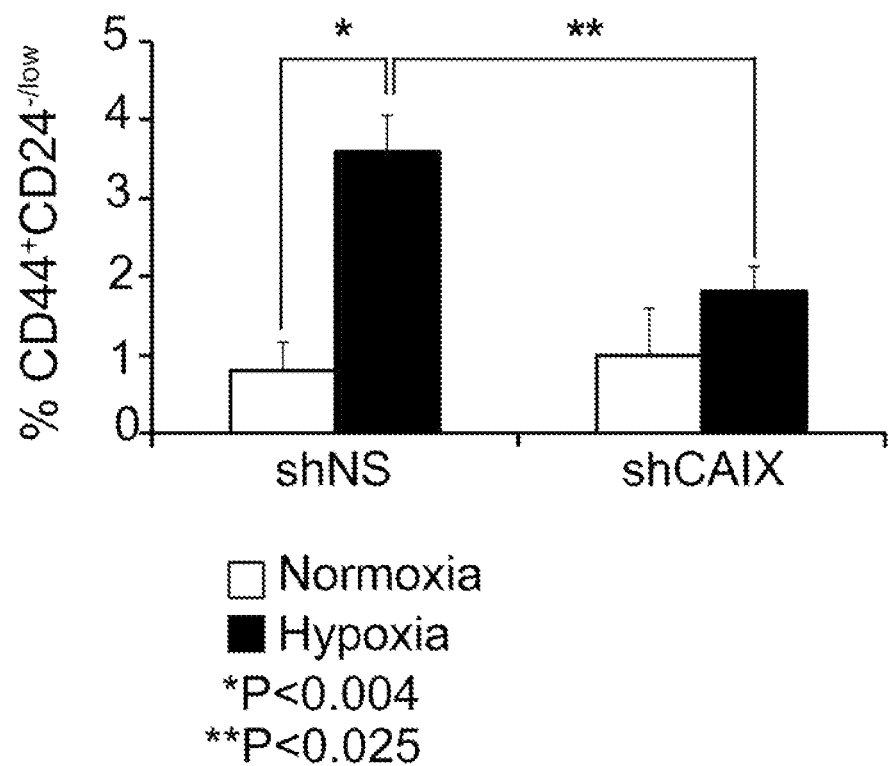
FIG. 5 shows graphical representations of the FACS data showing the mean changes in % CD44+CD24−/low cells±SEM, from 3 independent experiments. Statistical significance was confirmed using T-test, *P<0.004, **P<0.025.

To further assess the role of CAIX in maintaining the hypoxic breast cancer stem cell niche in vitro, shNS-4T1 and shCAIX-4T1 were cultured under TS forming conditions, in normoxia or hypoxia, and used FACS to quantify the CSC population labeled as CD44+CD24−/low (FIGS. 4 and 5). In shNS controls, the CD44+CD24−/low population is increased in hypoxic culture conditions, compared to normoxic controls. However, RNAi-mediated knockdown of CAIX significantly depletes this population in hypoxia (FIG. 5). These data correlate with the differences noted in TS-forming ability in these cells (FIG. 3).

Example 2

CAIX Inhibitors are Capable of Reducing Stem Cell Behavior in Cancer Cells

Figure 6:
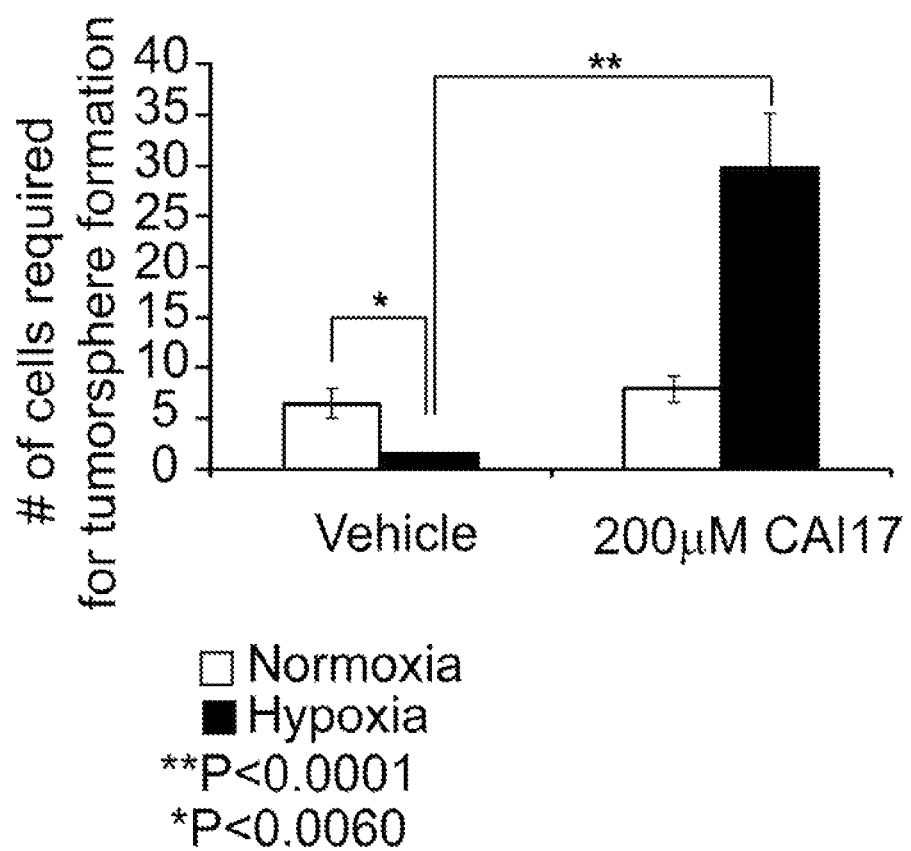
FIG. 6 is a graph of the number of cells required to initiate TS growth. Parental 4T1 were seeded at doubling dilutions and cultured under TS-forming conditions with 200 µM CAI17 or vehicle added, in normoxia or hypoxia. Mean±SEM of three independent experiments is shown. Statistical significance was confirmed using T-test, *P<0.001, **P<0.0060.

To verify these data, a well characterized CAIX small molecule inhibitor, CAI017, was used to inhibit CAIX activity in the parental 4T1 cell line (Lou, McDonald et al. 2011, Supuran 2008). Using the same experimental method described in Example 1, single cell suspensions of parental 4T1 were seeded at doubling dilutions in defined serum-free media, with CAI17 or vehicle added, and cultured as non-adherent TSs in normoxia or hypoxia for 7 days. Again, the number of parental 4T1 cells required to form TSs was significantly reduced in hypoxia, compared to normoxia controls, and inhibition of CAIX activity significantly increased the number of seeding cells required to form a TS in hypoxia, suggesting that CAIX activity alone may regulate the cancer stem cell-like population in this cell line (FIG. 6).

Figure 7:
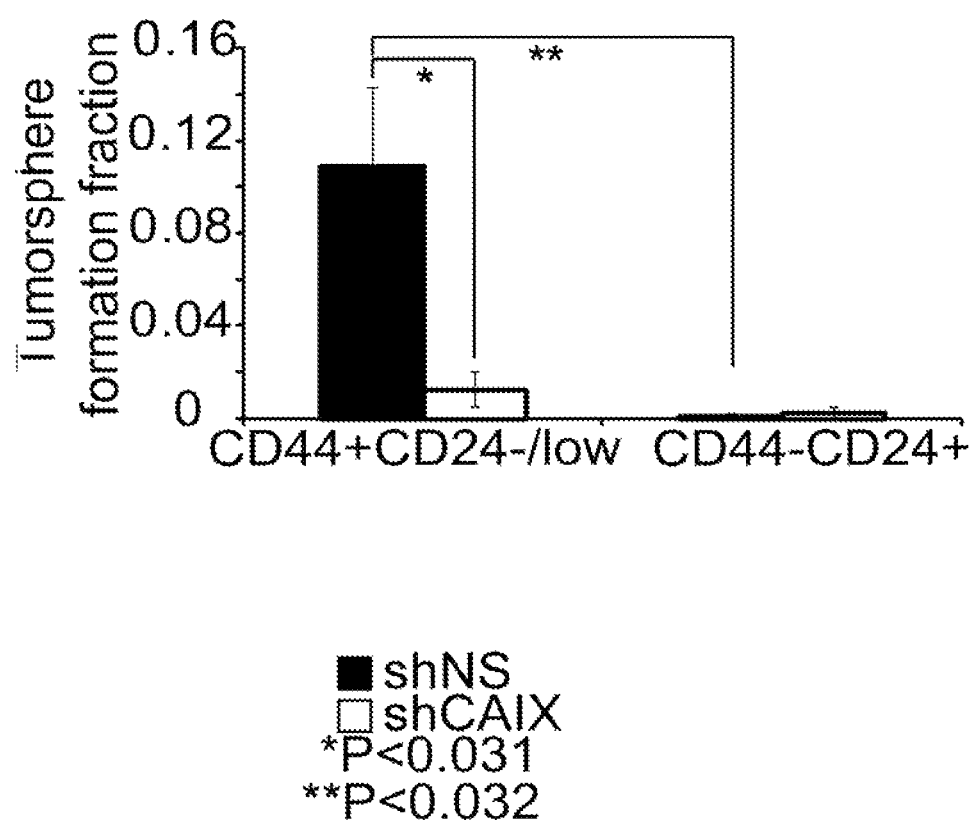
FIG. 7 is graphical depiction of TS formation fraction. 4T1 shNS and shCAIX cultured as TSs in hypoxia were subjected to FACS. CD44+CD24−/low or CD44-CD24+ control cells from both cell lines were seeded at doubling dilutions under TS-forming conditions in hypoxia and the number of cells required for formation was recorded (see supplemental table 1 for raw data). TS formation fraction was calculated, using mean TS formation fraction (±SEM) from 4 independent experiments.

To confirm the "stemness" properties of the CD44+ CD24−/low CSC populations quantified by FACS, TS cultured 4T1 shNS and shCAIX cells were subjected to FACS and CD44+CD24−/low and the control CD44−CD24+ populations collected and seeded at doubling dilutions under TS culture conditions in hypoxia. After 7 days, the number of cells required to form a TS was recorded, and TSs serially passaged in hypoxia. TS formation fraction was calculated as (1÷the number of cells required to form a TS). When TS formation was not observed, this was given a value of 0. As shown in (FIG. 7), viable shNS CD44+CD24− cells formed TSs in every experiment, from a relatively low number of cells, and grew vigorously. Viable shCAIX CD44+CD24− cells often failed to form TSs. On the occasions when TS formation was observed, this required a significantly higher number of cells than did the shNS CD44+CD24−/low population (FIG. 7). Viable control non-CSC populations, shNS CD44−CD24+ and shCAIX CD44−CD24+, showed a similarly poor TS formation fraction. When TS were subjected to serial passage and subsequent hypoxic TS culture conditions, shNS CD44+CD24− TS survived passaging well, up to passage 7 (when culture was ended), indicating stemness in this population. On the occasions when TS growth was observed in shCAIX CD44+CD24−/low populations, this characteristic did not survive past passage 1. Control CD44−CD24+ populations from either cell lines were similarly unable to be passaged beyond passage 1. These data suggest that CAIX depleted CD44+CD24− low cells, despite expressing the CD44+CD24−/low signature, do not display the characteristics associated with stemness in vitro (Lock, McDonald et al. 2012).

TABLE 1

CAIX expression is required for 4T1 CD44+CD24−/low tumorsphere-forming ability in hypoxia
Minimum cell # required for positive TS growth

|  | N = 1 expt | N = 2 expt | N = 3 expt | N = 4 expt |
| --- | --- | --- | --- | --- |
| shNS CD44+CD24−/low | 124 | 7 | 7 | 7 |
| shCAIX CD44+CD24−/low | No TS | No TS | 34 | 46 |
| shNS CD44−CD24+ | No TS | 32 cells | 218 | 761 |
| shCAIX CD44−CD24+ | No TS | No TS | 421 | 101 |

For Table 1 data, 4T1 shNS and shCAIX cells were cultured as TSs in hypoxia, disaggregated, stained for CD44 and CD24, and collected by FACS. CD44+CD24−/low or CD44−CD24+ control cells were collected and seeded at doubling dilutions under tumorsphere-forming conditions in hypoxia and tumorsphere forming efficiency was recorded.

Example 3

Figure 8:
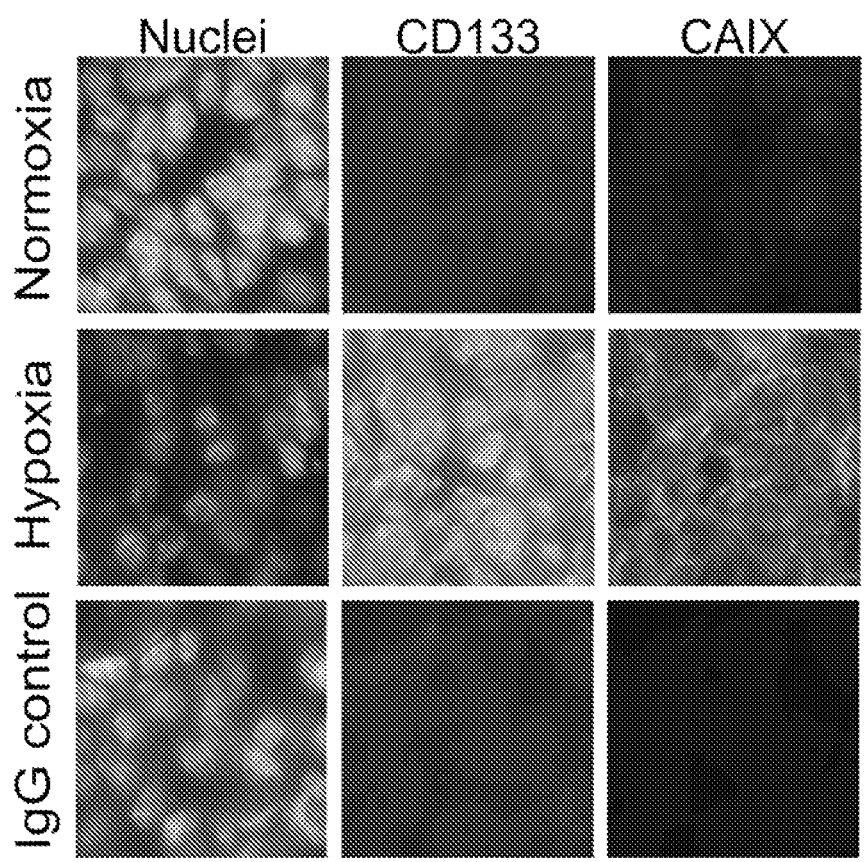
FIG. 8 shows immunostained images of parental 4T1 cultured under constant rotation as tumorspheres under normoxia or hypoxia, frozen, and sectioned. Immunostaining was to assess expression of the cancer stem cell marker CD133 and CAIX. Bar=50 µm.
Figure 9:
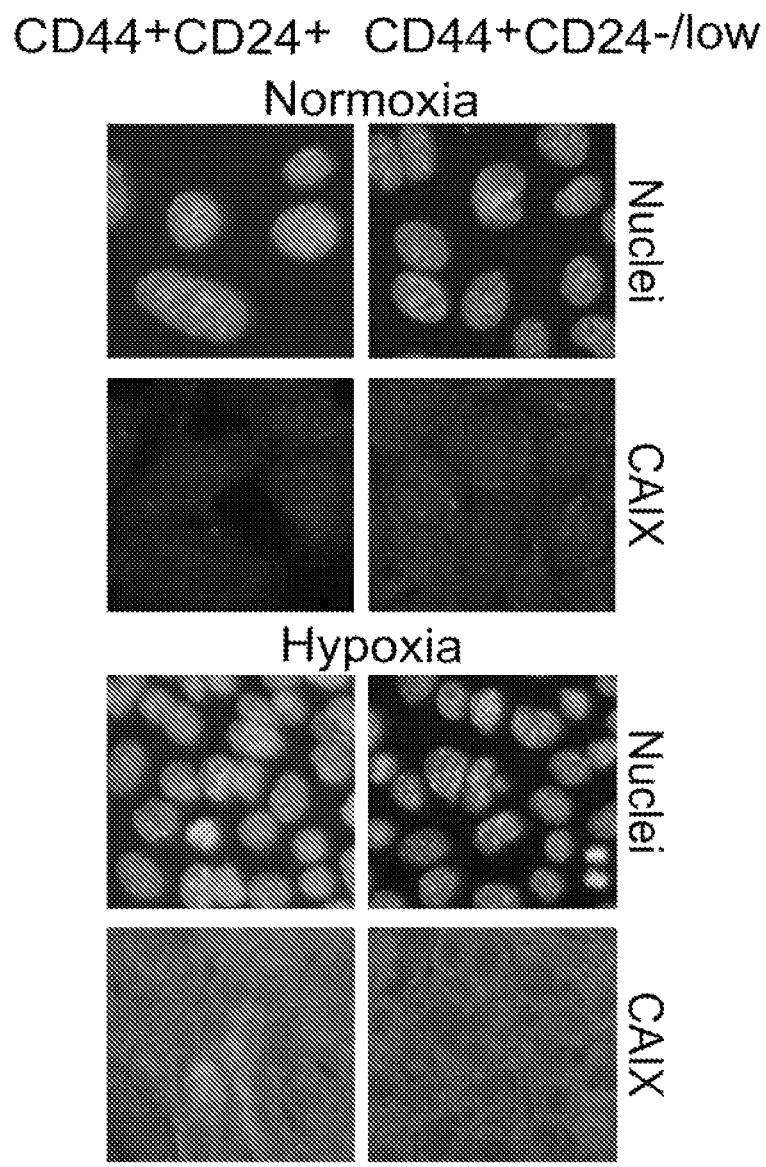
FIGS. 9-12 show immunostained parental 4T1 cells cultured as TSs in normoxia or hypoxia, disaggregated, stained for CD44, CD24 and collected by FACS. CD44+CD24−/low or CD44+CD24+ cells were cultured on glass coverslips in normoxia or hypoxia, as appropriate, then fixed and immunostained for CAIX (FIG. 9); E-cadherin (FIG. 10); a mesenchymal marker e.g. smooth muscle actin (FIG. 11); and the EMT regulator Snail (FIG. 12).
Figure 10:
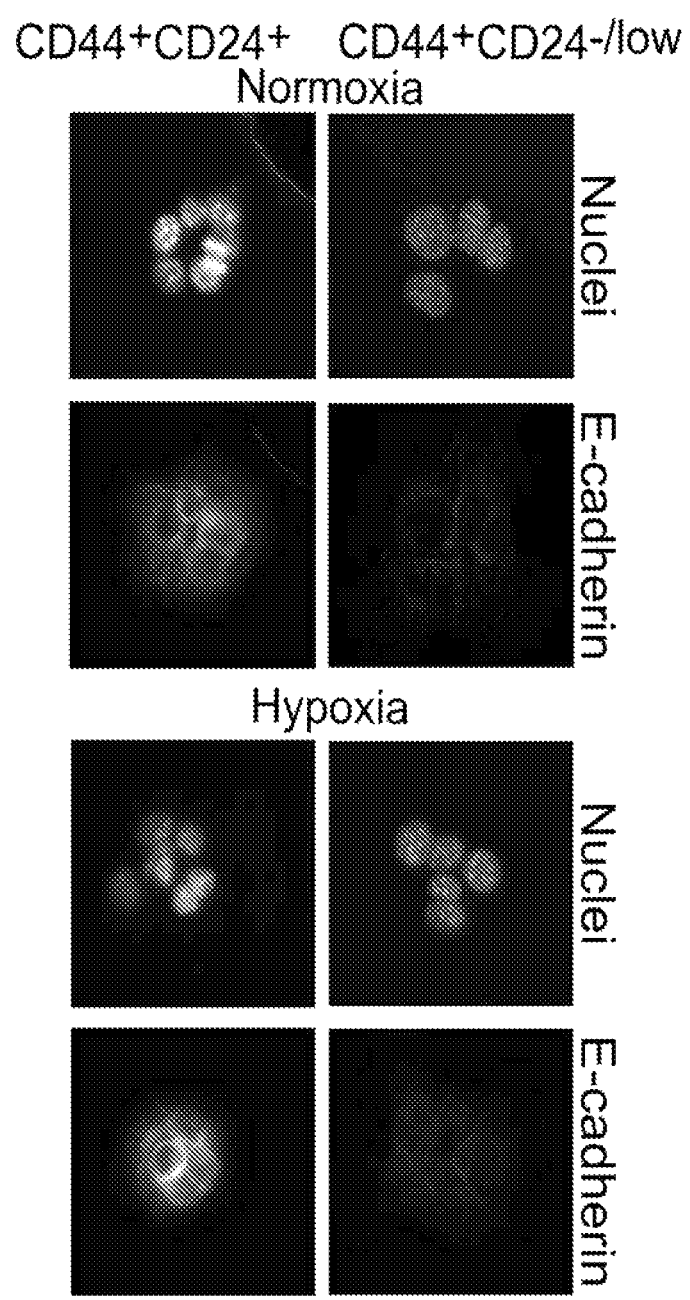
Figure 11:
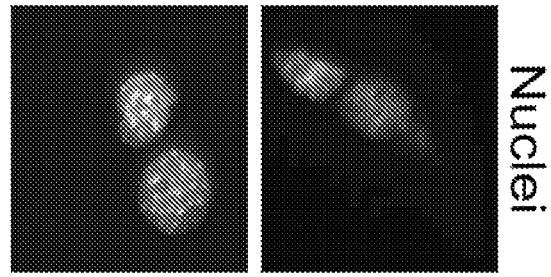
Figure 11:
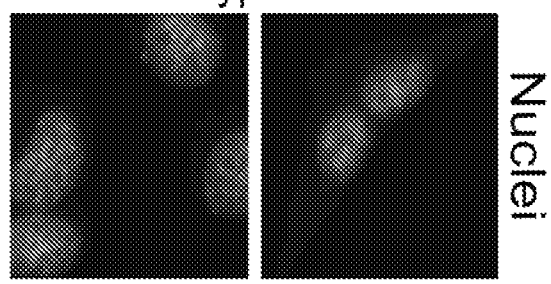
Figure 12:
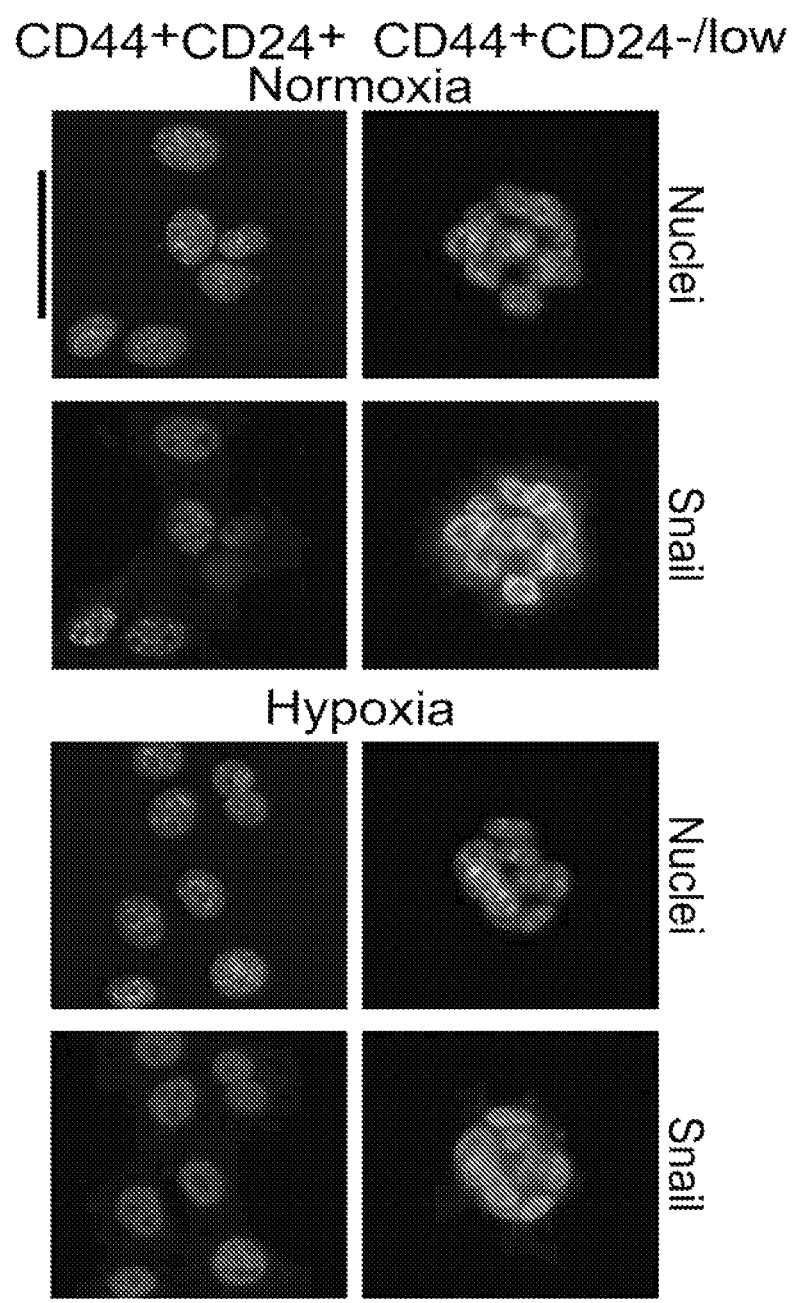

The Mesenchymal Phenotype of Parental 4T1 CD44+CD24−/Low CSC is Observed in Normoxia and Hypdxia Parental 4T1 cells were cultured under tumorsphere (TS) forming conditions in normoxia and hypoxia. After 7 days, TSs were collected, dissociated, and cells stained for CD44 and CD24. CD44+CD24−/low cells or a control CD44+ CD24+ population were cultured for 3 days on glass coverslips in normoxia or hypoxia, then fixed and immunostained for CAIX (FIG. 9) or EMT markers (FIGS. 8, 9 and 10) (Lock, McDonald et al. 2012). Expression of CAIX was upregulated in hypoxic cultures in both CD44+CD24−/low and CD44+CD24+ control populations. No significant CAIX staining was observed in normoxic cultures (FIG. 9). Whereas significant E-cadherin expression was observed at cell boundaries in the CD44+CD24+ control populations in normoxia and hypoxia, significant loss of the expression of the epithelial marker E-cadherin was observed in CD44+ CD24−/low cells in normoxia and hypoxia (FIG. 10). Further evidence of the CD44+CD24−/low mesenchymal phenotype was confirmed by the observed upregulation of the mesenchymal marker smooth muscle actin in CD44+ CD24−/low 4T1 cells, compared to negligible staining in the CD44−CD24+ control population (FIG. 11). Immunofluorescence staining for Snail also demonstrated upregulation of this EMT regulator in the normoxic and hypoxic CD44+ CD24−/low population, compared to less staining in the control CD44+CD24+ populations (FIG. 12).

These data were confirmed in vitro. Parental 4T1 murine breast cancer cells were cultured as TSs under constant rotation for 3 weeks. When TSs reached approximately 150 μm across, cultures were divided and further cultured under normoxia or hypoxia for 3 days. TSs were frozen, sectioned and subjected to immunostaining to assess expression of CAIX and the cancer stem cell marker CD133. The results show that CD133 expression was upregulated in hypoxic TSs compared to normoxic controls. CAIX expression was also upregulated in these cells.

Figure 13:
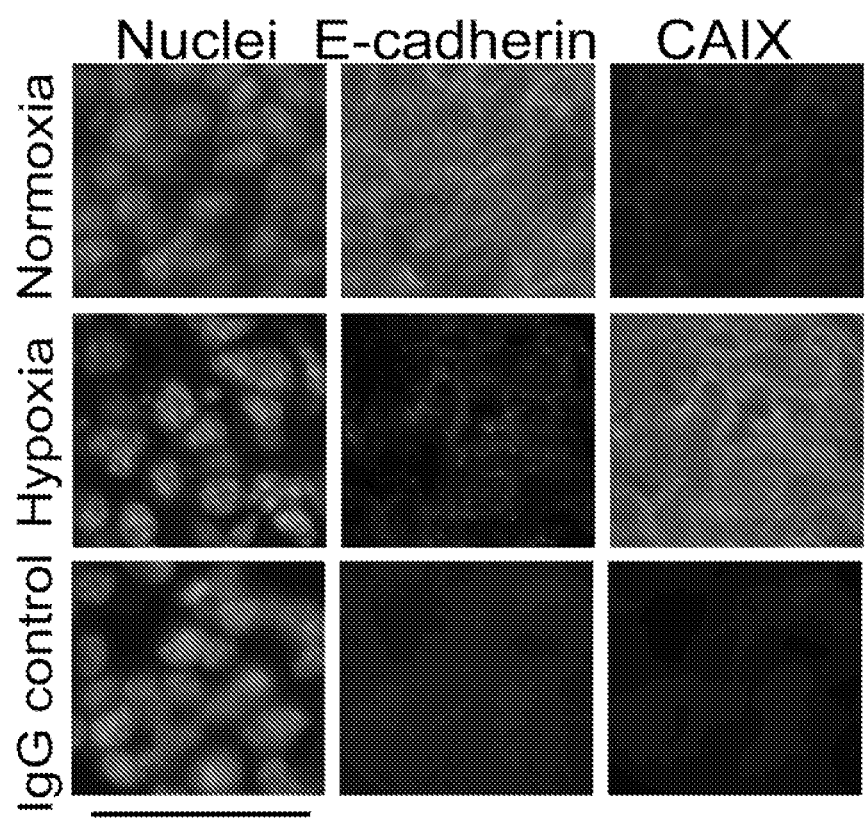
FIGS. 13-15 show immunostained images of parental 4T1 cultured under constant rotation as tumorspheres under normoxia or hypoxia, frozen, and sectioned. Immunostaining was to assess expression of the epithelial marker E-cadherin and CAIX (FIG. 13); the mesenchymal marker smooth muscle actin and CAIX (FIG. 14); and the EMT regulator Snail and CAIX (FIG. 15). Bar=50 µm.
Figure 14:
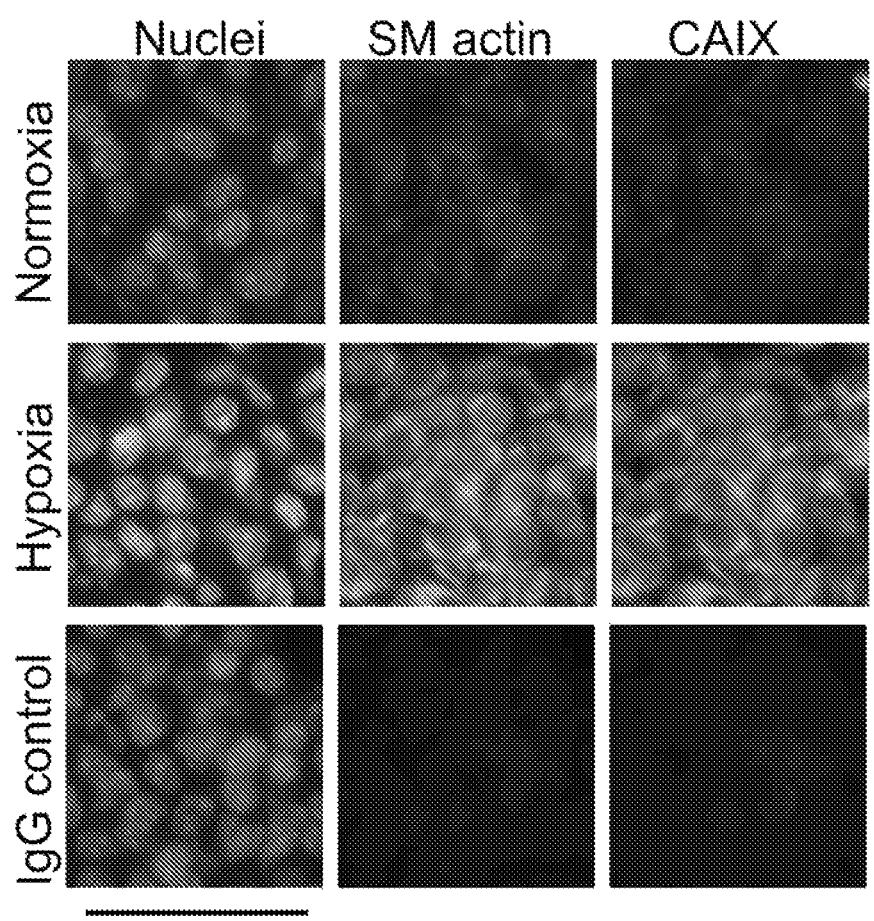
Figure 15:
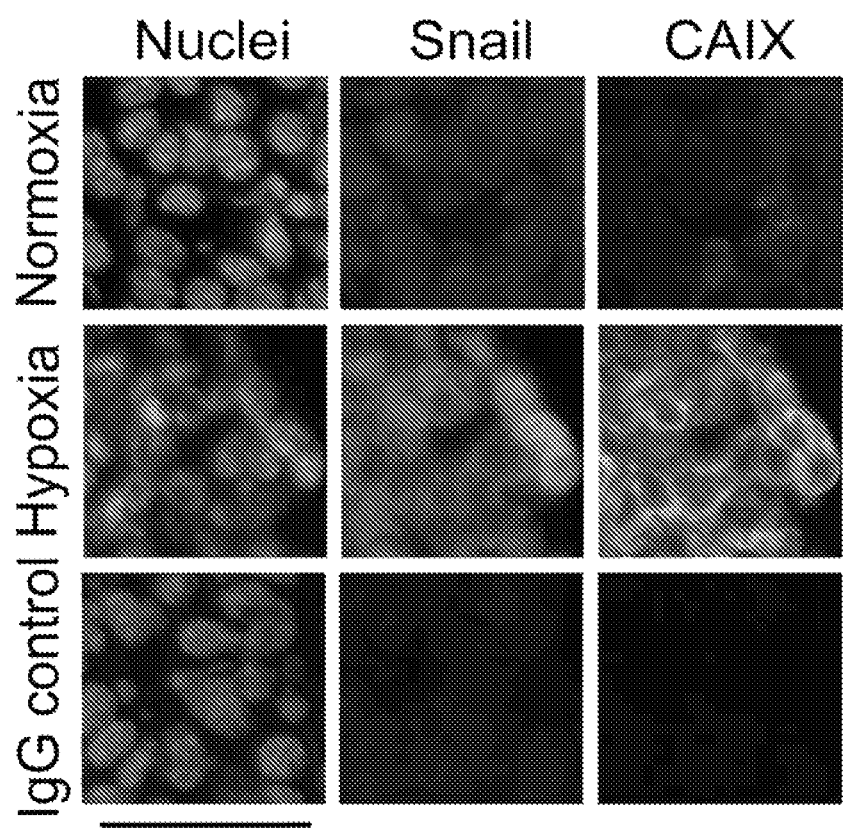

To assess the epithelial phenotype of 4T1 cultures as TSs in hypoxia, sections were co-stained for the epithelial marker E-cadherin and CAIX (FIG. 13). E-cadherin expression at cell boundaries was observed in normoxic tumorspheres, with very little CAIX expression in these cells. E-cadherin expression was downregulated in tumorspheres cultured in hypoxia, concomitant with increased CAIX expression. Expression of the mesenchymal marker smooth muscle actin and the EMT regulator Snail was also assessed in these tumorspheres. Smooth muscle actin expression as well as CAIX expression were upregulated in hypoxia, compared to normoxic controls (FIG. 14). Snail and CAIX expression was increased in hypoxic TS compared to normoxic controls (FIG. 15). Taken together, these data support that in parental 4T1 mouse breast cancer cells, hypoxic tumorsphere culture causes CAIX expression, which correlates with cancer stem cell marker expression and an EMT phenotype. These data confirm hypoxic induction of EMT and maintenance of a stem cell phenotype in this cell line.

Example 4

Figure 16:
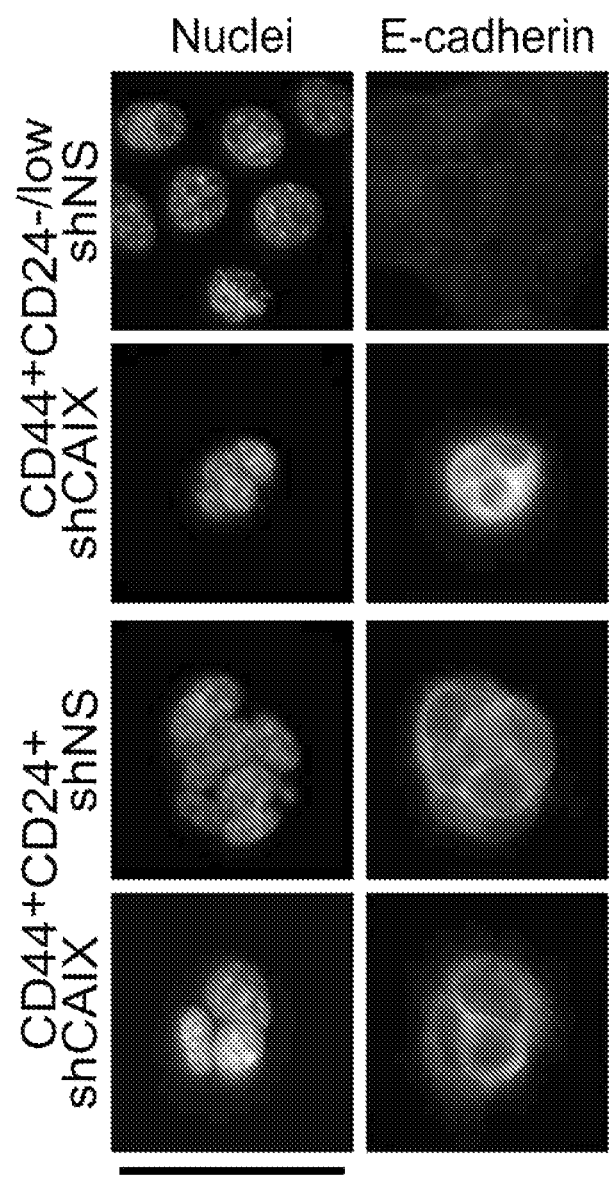
FIGS. 16-18 shows immunostained 4T1 shNS and shCAIX cells cultured as TSs in hypoxia, disaggregated, stained for CD44, CD24 and collected by FACS. Viable CD44+CD24−/low or CD44+CD24+ cells were collected and cultured on glass coverslips in hypoxia for 3 days, fixed and assessed by immunostaining for expression of E-cadherin (FIG. 16); Smooth muscle actin (FIG. 17); and Snail (FIG. 18).

CAIX is Required for the Mesenchymal and "Stemness" Phenotype of 4T1 CD44+CD24−/Low Cells in Hypdxia The requirement for CAIX expression in maintaining the CSC "stemness" of cancer cells was further analyzed by assessing the EMT phenotype. shNS and shCAIX 4T1 cells were cultured in hypoxia for 7 days, dissociated, and the CD44+CD24−/low and control populations were collected by FACS. Cells were cultured under glass coverslips in hypoxia for 3 days, fixed, and assessed by IF (Lock, McDonald et al. 2012). Expression of the epithelial marker E-cadherin is significantly decreased in shNS CD44+CD24−/low cells compared to controls (FIG. 16), suggesting that shNS CD44+CD24−/low cells undergo EMT, similar to 4T1 parental CD44+CD24−/low populations. In contrast, shCAIX CD44+CD24−/low cells continue to express E-cadherin comparable to shCAIX CD44+CD24+ control cells (FIG. 16).

Figure 17:
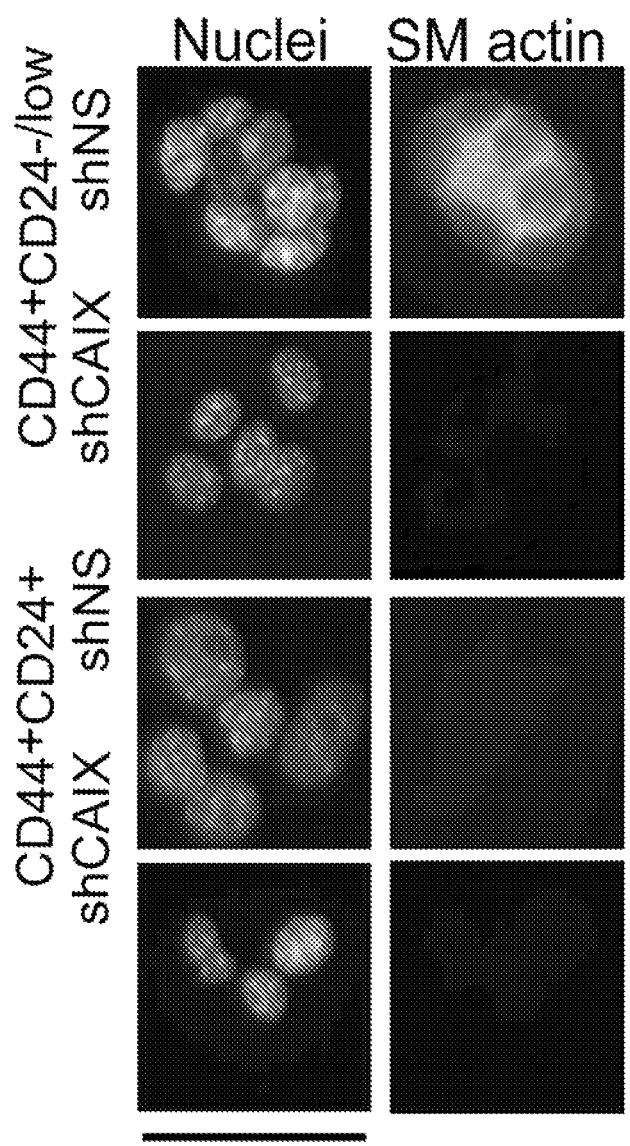
Figure 18:
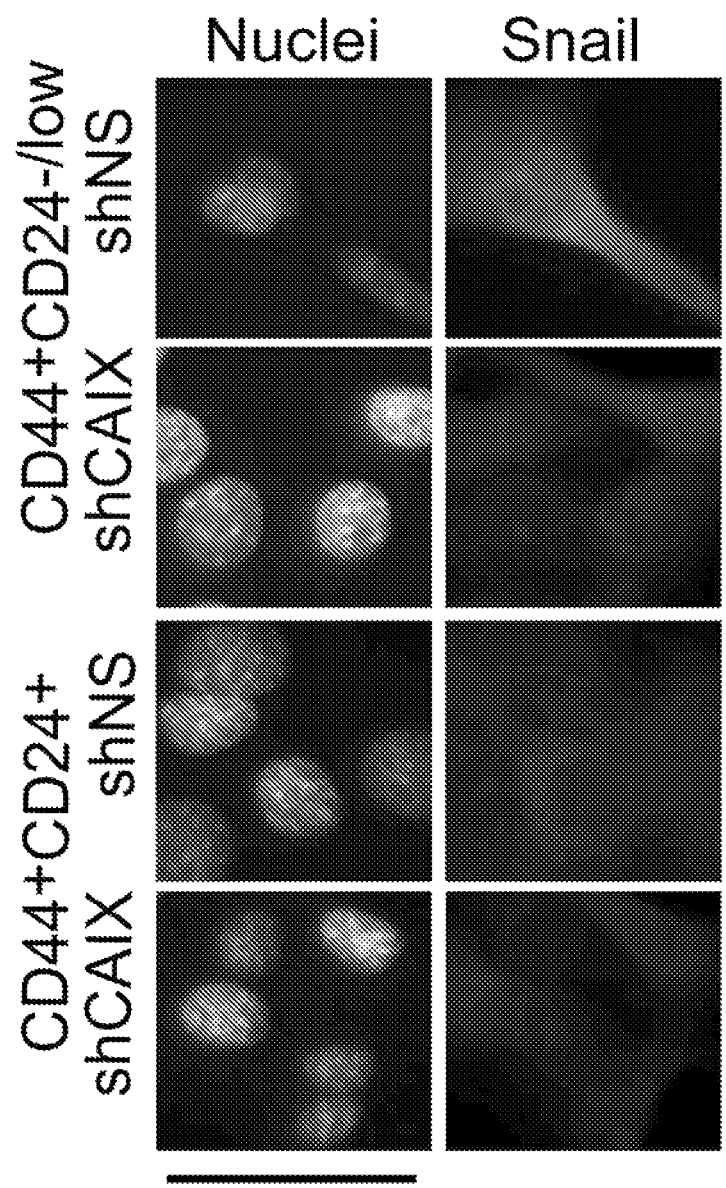

Expression of the mesenchymal marker smooth muscle actin was also assessed. shNS CD44+CD24−/low cells display robust staining for smooth muscle actin, compared to very little staining observed in shNS CD44+CD24+ controls cells. In contrast, following CAIX depletion, shCAIX CD44+CD24−/low cells show very low levels of smooth muscle actin expression, similar to shCAIX CD44+CD24+ controls (FIG. 17). To confirm these data, expression of the EMT regulator Snail was also assessed by IF. Snail expression was upregulated in shNS CD44+CD24−/low cells compared to shCAIX CD44+CD24−/low cells and controls (FIG. 18).

Figure 19:
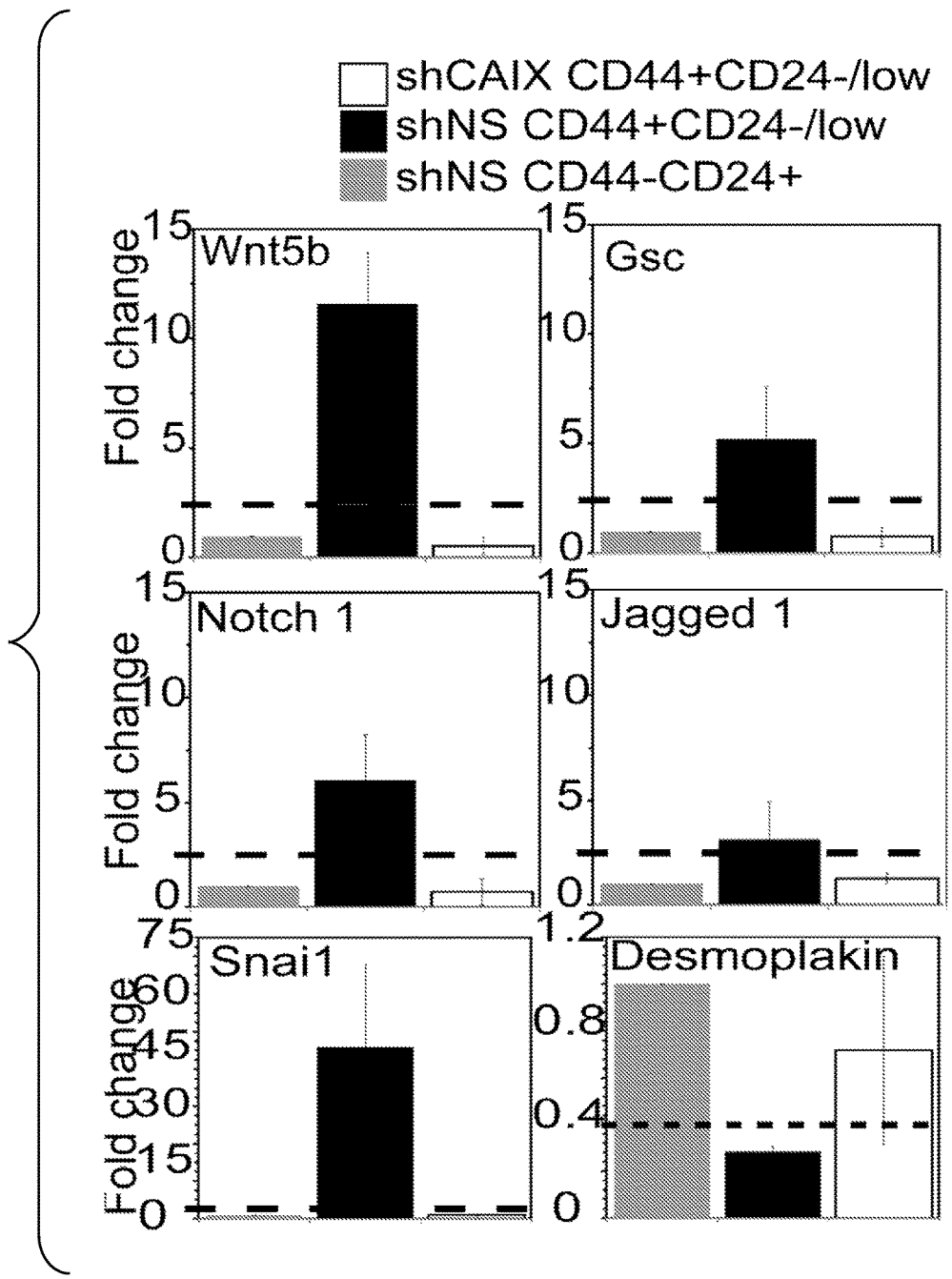
FIG. 19 is a series of graphs showing mRNA levels for various EMT markers. 4T1 shNS and shCAIX cells were cultured as TSs in hypoxia, disaggregated, cells stained for CD44, CD24 and collected by FACS. Viable CD44+CD24−/low or CD44+CD24+ cells were collected and cultured on glass coverslips in hypoxia for 3 days, lysed, RNA extracted and relative mRNA levels of various EMT markers assessed by QPCR. Mean and SEM fold change of three independent experiments are given.

Viable, FACS sorted cells were cultured in hypoxia for 3 days. RNA was extracted, and quantitative PCR was used to assess the relative gene transcription levels of EMT target genes (Lock, McDonald et al. 2012). A mean 3.5 fold decrease in transcription of the epithelial marker Desmoplakin was observed in shNS CD44+CD24−/low cells, compared to controls, with no significant decrease in shCAIX CD44+CD24−/low cells observed (FIG. 19). A similar pattern in E-cadherin transcription was also observed (data not shown). Increased transcription of the mesenchymal marker Vimentin was observed in shNS CD44+CD24−/low cells, compared to controls, with no difference in shCAIX CD44+CD24−/low cells (data not shown). These differences in EMT-target gene transcription verify that CAIX depletion maintains the epithelial phenotype of the CD44+CD24−/low population, in comparison to the confirmed EMT phenotype observed in CAIX expressing shNS CD44+CD24−/low cells in hypoxia.

A significant mean fold increase in transcription of the EMT regulators Snaill (Snail) (45.8 fold) (Cano, Perez-Moreno et al. 2000) and Wnt5b (11.57 fold) (Yook, Li et al. 2005, Malizia, Lacey et al. 2009) was observed in shNS CD44+CD24−/low cells, compared to controls. Goosecoid (Gsc), a known EMT regulator, which is overexpressed in a majority of human breast tumors and promotes metastasis (Hartwell, Muir et al. 2006) was also up regulated by 5.23 fold (Hartwell, Muir et al. 2006) in shNS CD44+CD24−/low cells. Strikingly, no significant increase in transcription of these three EMT regulators was observed in shCAIX CD44+CD24−/low cells (FIG. 19). Transcription of the EMT regulator Zeb2 (Vandewalle, Van Roy et al. 2009) was also upregulated in shNS CD44+CD24−/low cells, compared to shCAIX CD44+CD24−/low cells and controls (data not shown). Transcription of FOXC2, an EMT promoter which is upregulated in aggressive human breast cancers (Mani, Yang et al. 2007), also showed a similar pattern (data not shown). These results demonstrate that CAIX is required for the mesenchymal phenotype and maintenance of breast cancer stem cells in hypoxia.

Transcription of members of the Notch signaling pathway regulators, Notch1 and its ligand Jagged1 were also assessed (Lock, McDonald et al. 2012). Transcription of both Notch1 and its downstream effector Jagged 1 showed a mean 6.09 and 3.12 fold increase, respectively, in shNS CD44+CD24−/low cells compared to controls. In contrast, no significant upregulation in transcription of either of these regulators of stemness was observed in the CAIX-depleted shCAIX CD44+CD24−/low cell population (FIG. 19).

Several genes assessed by quantitative PCR which did not show any significant differences between the analyzed cell populations are shown in Table 2.

TABLE 2

| Nonreactive biomarkers | | | | |
|---|---|---|---|---|
| Gene name | Fold change | shNS CD44−CD24+ | shNS CD44+CD24− | ShCAIX CD44+CD24− |
| Rac1 | mean | 1 | 0.82 | 1.15 |
| | SEM | 0 | 0.04 | 0.16 |
| Tmem132a | mean | 1 | 1.04 | 1.08 |
| | SEM | 0 | 0.02 | 0.46 |
| Moesin | mean | 1 | 1.01 | 1.02 |
| | SEM | 0 | 0.08 | 0.04 |
| Beta 1 Integrin | mean | | 1.03 | 1.00 |
| | SEM | | 0.20 | 0.10 |

4T1 shNS and shCAIX cells were cultured as TSs in hypoxia, disaggregated, cells stained for CD44, CD24 and collected by FACS. Viable CD44+CD24−/low or CD44+CD24+ cells were collected and cultured on glass coverslips in hypoxia for 3 days, lysed, RNA extracted and relative mRNA levels of various EMT markers assessed by QPCR. Table 2 shows a selection of gene targets displaying no significant changes across all cell populations. Mean and SEM fold change of three independent experiments are given.

Figure 20:
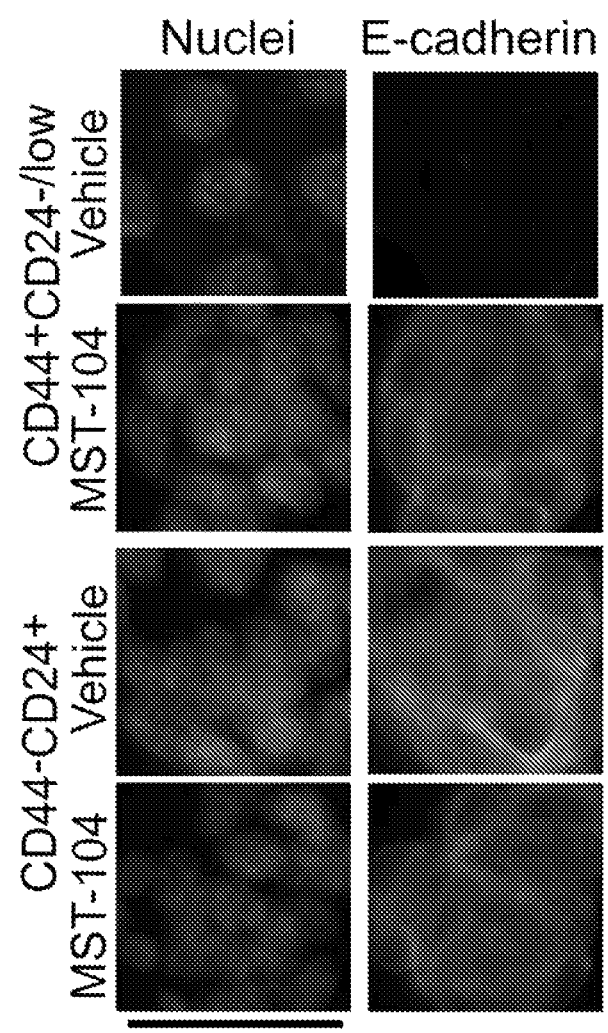
FIG. 20 are images of parental 4T1 cells cultured as TSs in normoxia, disaggregated, stained for CD44, CD24 and collected by FACS. Viable CD44+CD24−/low or CD44−CD24+ cells were collected and cultured on glass coverslips in hypoxia for 5 days, with and without 50 µM MST-104, fixed and assessed by immunostaining for expression of E-cadherin.

To confirm these data, parental 4T1 TSs were analyzed by FACS, CD44+CD24−/low and control CD44−CD24+ cell populations were cultured in hypoxia on glass coverslips in the presence or absence of the CAIX inhibitor MST-104. Cells were fixed and stained for the epithelial marker E-cadherin. As expected, vehicle treated CD44−CD24+ cells show strong E-cadherin staining localized to cell-cell boundaries. In contrast, vehicle treated CD44+CD24−/low cells had very little or no E-cadherin expression. Importantly, CD44+CD24−/low cells treated with CAIX inhibitor MST-104 showed robust E-cadherin staining, very similar to CD44−CD24+ cells treated with MST-104 or vehicle, confirming the epithelial phenotype of these cells (FIG. 20).

Example 5

Figure 21:
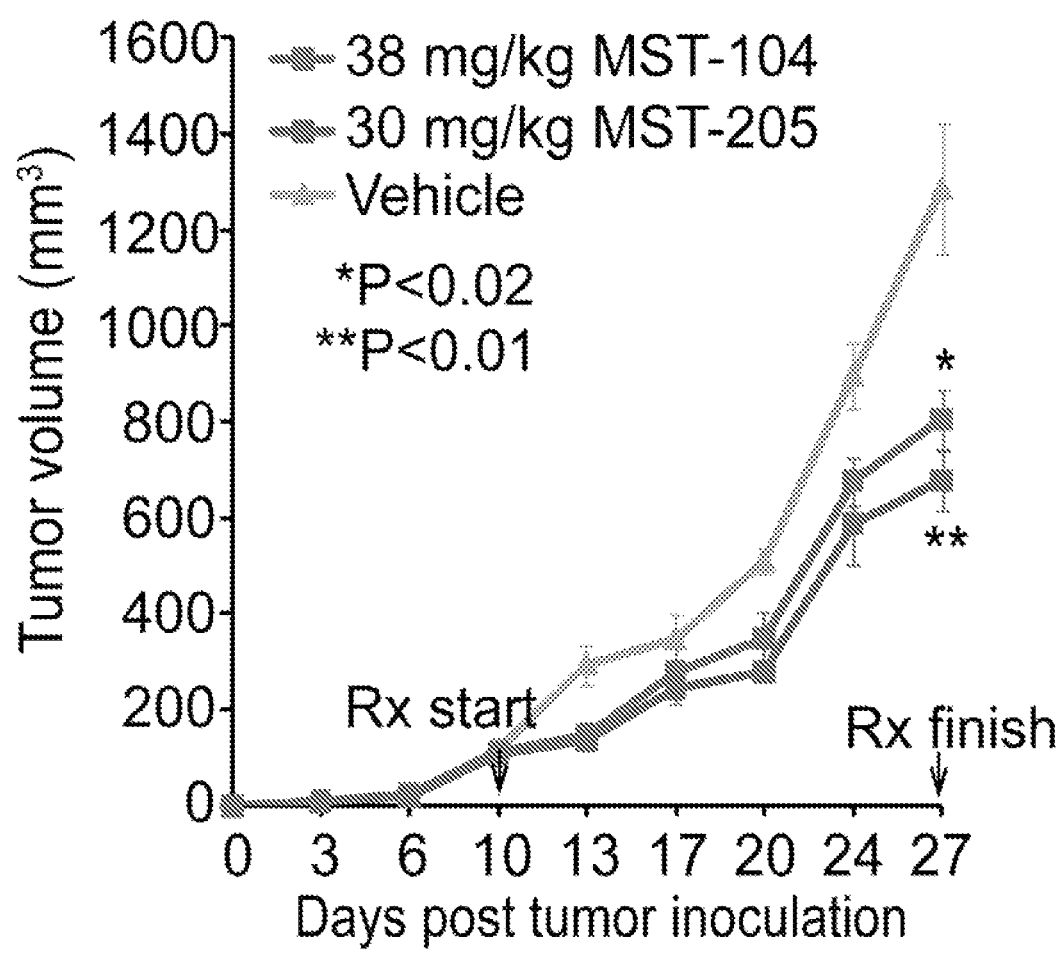
FIG. 21 is a graphical representation of in vivo tumor growth. MDA-MB-231 LM2-4luc+ were implanted orthotopically into NOD/SCID mice. When tumors reached an average of 200 mm$^2$, animals received either vehicle, 38 mg/kg MST-104 or 30 mg/kg MST-205. Subsequent tumor growth was monitored. n=8/group.*P<0.02, **P<0.01.

CAIX-Specific Inhibitors Delay Tumor Growth and the Cancer Stem Cell Population In Vivo To evaluate the effect of CAIX inhibition on tumor growth and cancer stem cell expansion in vivo, primary breast tumor xenografts were established using a variant of the MDA-MB-231 cell line, MDA-MB-231 LM2-4Luc+. These cells are highly metastatic in vivo and robustly induce CAIX expression in hypoxia. Cells were implanted orthotopically and when tumor formation was confirmed, mice were treated with two previously described CAIX-specific inhibitors, the glycosylcoumarin MST-205 and a ureido-sulfonamide MST-104 (Lou, McDonald et al. 2011, Lock, McDonald et al. 2012, Pacchiano, Carta et al. 2011). Tumor growth was assessed by caliper measurement and IVIS imaging. Tumor volume measurements showed significant inhibition of primary tumor growth in mice treated with either inhibitor, compared to vehicle controls, similar to previous reports (FIG. 21) (Lou, McDonald et al. 2011).

Figure 22A:
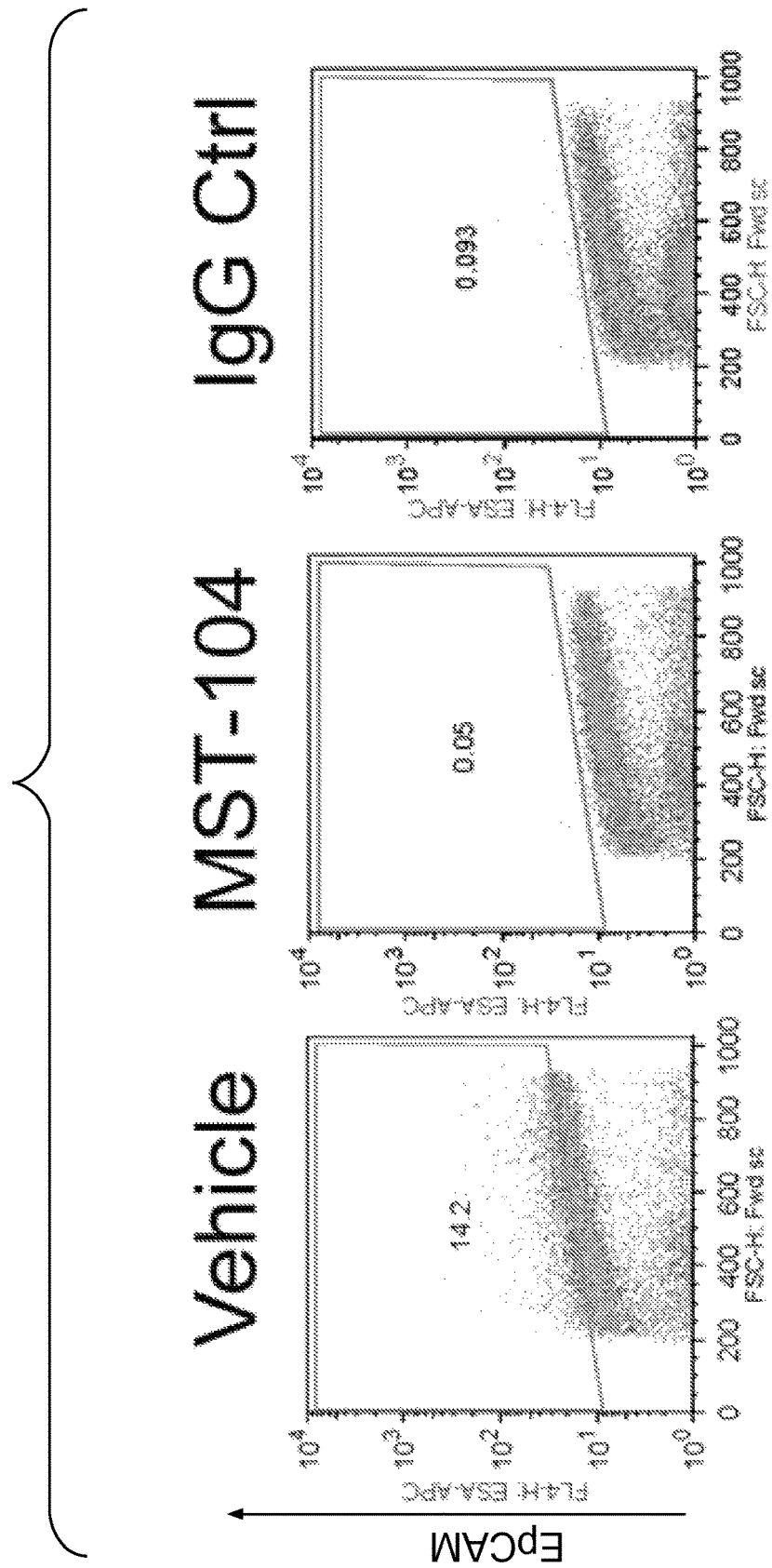
FIGS. 22A and 22B are representative FACS plots (FIG. 22A) and a bar graph (FIG. 22B), showing the mean changes in EpCAM+ cells±SEM, from 3 mice. MDA-MB-231 LM2-4luc+ were implanted orthotopically into NOD/SCID mice. When tumors reached an average of 200 mm$^2$, animals received either vehicle or 38 mg/kg MST-104. After 27 days, primary tumors were removed, dissociated and EpCAM+ cell population assessed by FACS analysis. Statistical significance was confirmed using T-test. *P<0.0331, P<0.0224.
Figure 22B:
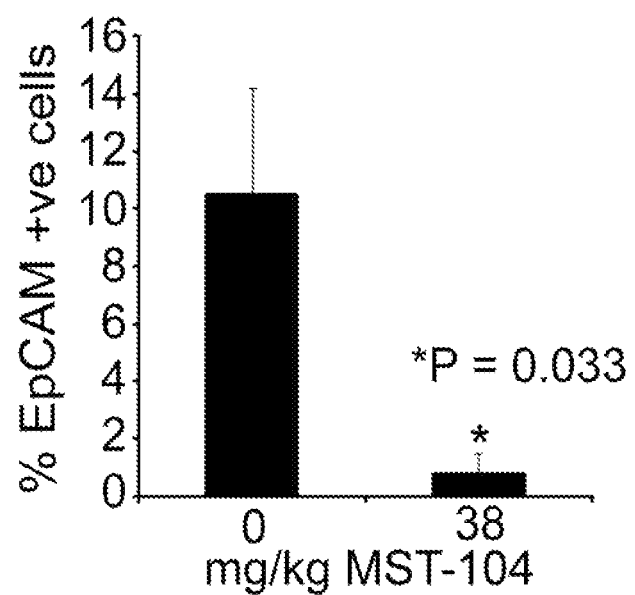
Figure 23A:
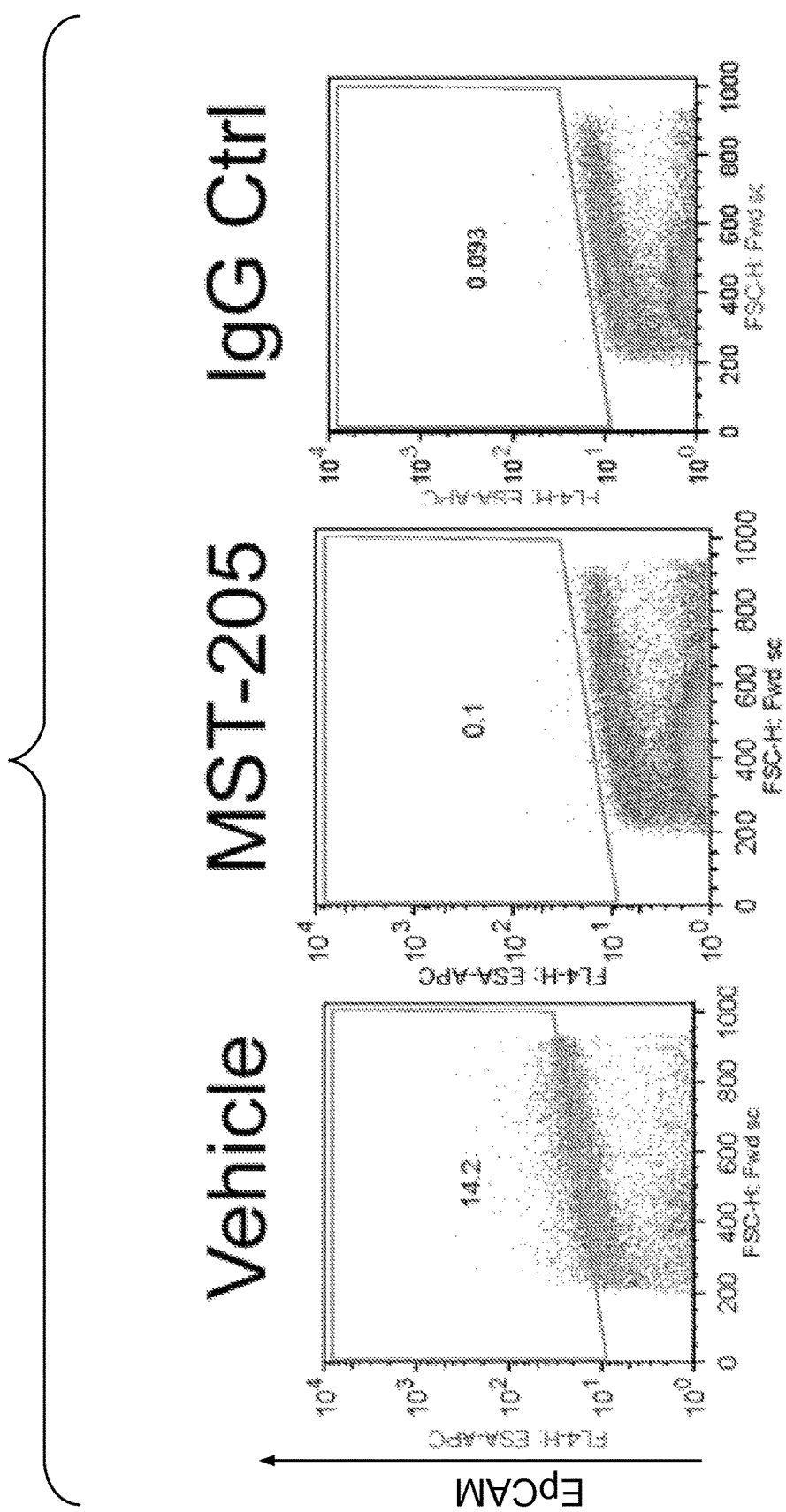
FIGS. 23A and 23B are representative FACS plots (FIG. 23A) and a bar graph (FIG. 23B) showing MDA-MB-231 LM2-4luc+ cells that were implanted orthotopically into NOD/SCID mice. When tumors reached an average of 200 mm$^2$, animals received either vehicle or 30 mg/kg MST-205. After 27 days, primary tumors were removed, dissociated and EpCAM+ cell population assessed by FACS analysis. Representative FACS plots are shown. Bar graph shows the mean changes in EpCAM+ cells±SEM, from 3 mice. Statistical significance was confirmed using T-test. *P<0.0331, P<0.0224.
Figure 23B:
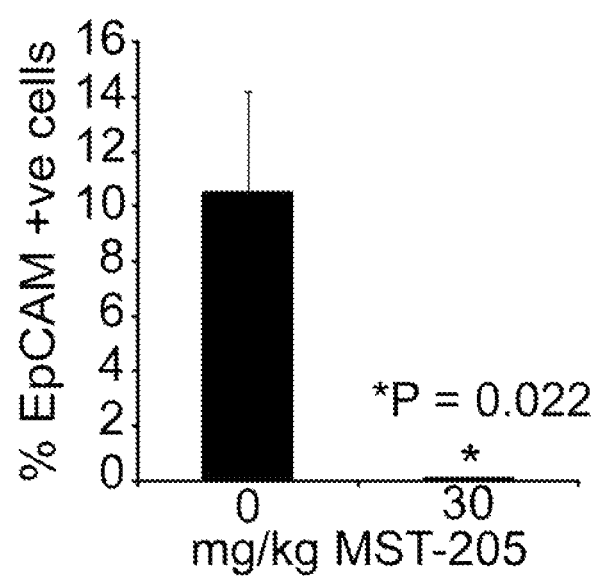

The effect of CAIX inhibition on the primary tumor cancer stem cell population in vivo was quantified. Twenty-seven days post-inoculation, primary tumors were removed, dissociated, cells were labeled for the cancer stem cell marker EpCAM (formerly known as ESA) and assessed by FACS. Vehicle treated LM2-4Luc+ tumors contained a mean 10% EpCAM+ population. In comparison, MST-104 treated tumors displayed a statistically significant reduced EpCAM+ population (FIGS. 22A and 22B). Another class of CAIX inhibitor, MST-205, also displayed a significantly reduced population, compared to vehicle-treated control tumors (FIGS. 23A and 23B).

Figure 24:
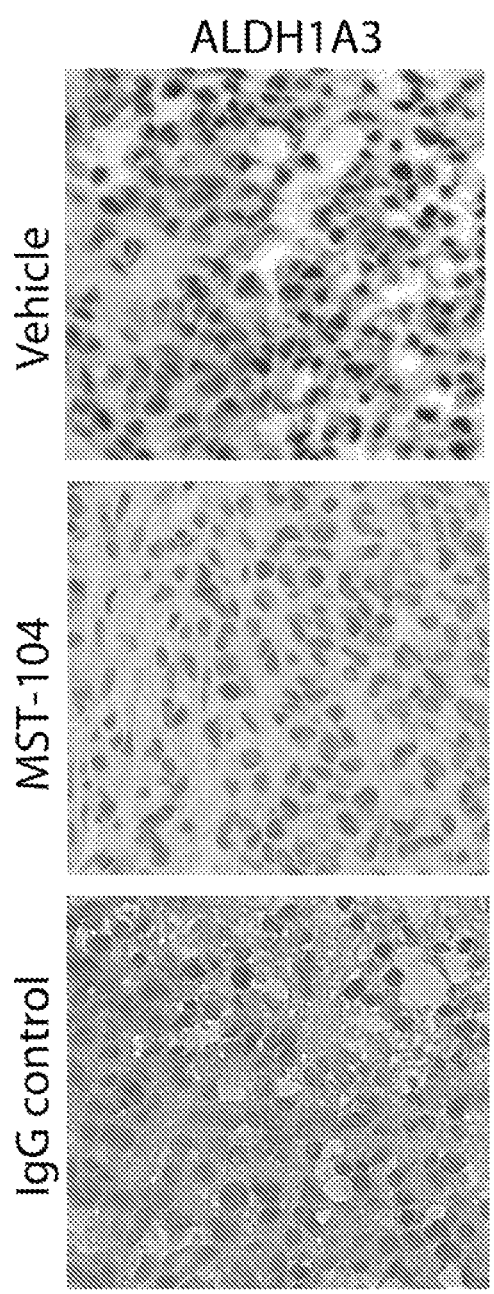
FIG. 24 shows images of IHC-labeled tumors. MDA-MB-231 LM2-4luc+ cells were implanted orthotopically into NOD/SCID mice. When tumors reached an average of 200 mm$^2$, animals received either vehicle, 38 mg/kg MST-104. After 27 days, primary tumors were fixed, sectioned and subjected to IHC to assess expression of the positive cancer stem cell marker ALDH1A3.
Figure 25:
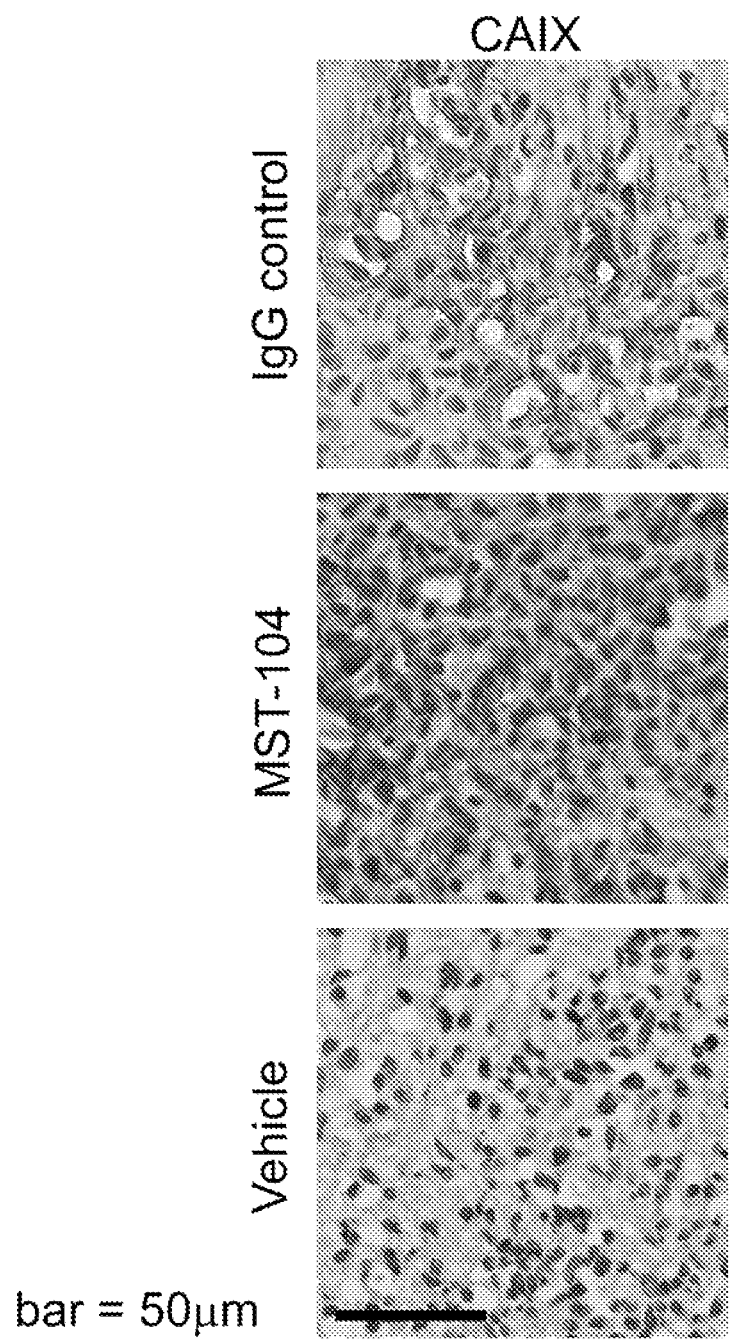
FIG. 25 shows images of IHC labeled tumors. MDA-MB-231 LM2-4luc+ cells were implanted orthotopically into NOD/SCID mice. When tumors reached an average of 200 mm$^2$, animals received either vehicle or 38 mg/kg MST-104. After 27 days, primary tumors were fixed, sectioned and subjected to IHC to assess expression of CAIX.

To confirm the observed differences in the putative cancer stem cell population following CAIX inhibition, tumors were also assessed for ALDH1A3 expression by immunohistochemistry (IHC) (FIG. 24). A small population of ALDH1A3 positive cells were observed in vehicle treated tumors, in perinecrotic regions. Sequential tissue section staining also confirmed CAIX expression in these areas (FIG. 25). In CAIX-inhibitor treated tumors, ALDH1A3 staining was largely absent in perinecrotic areas, whilst CAIX expression was still observed.

Example 6

EpCAM+MDA-MB-231 LM2-4 Subpopulations are Highly Tumorigenic In Vivo

To test whether the selected EpCAM+MDA-MB-231 LM2-4 cells form tumors, we injected 50, 500 and 5000 EpCAM+ or EpCAM-MDA-MB-231 LM2-4 cells, respectively (50,000 EpCAM– ve cells were also injected) into the mammary fat pads of NOD/SCID mice. EpCAM+ cells were highly tumorigenic since tumor formation could be observed from a starting population of very few EpCAM+ cells within a few days. Although EpCAM– cells were also able to form tumors when more cells were injected, the volume of the EpCAM– derived tumors was always much less than that of EpCAM+ derived tumors (Lock, McDonald et al. 2012). Also the rate of tumor progression was slower in EpCAM–-derived tumors than EpCAM+-derived tumors, indicating that EpCAM+ cells formed more aggressive tumors.

These results suggest that the cancer stem cells of MDA-MB-231 LM2-4 were enriched by EpCAM+ selection. These data are similar to the differences in tumor growth observed following xenograft EpCAM+/PROCR+ or EpCAM–/PROCR-MDA-MD-231 breast cancer stem cells (Hwang-Verslues, Kuo et al. 2009).

Example 7

CAIX Inhibition Rescues Paclitaxel-Driven CSC Expansion In Vivo

Figure 26:
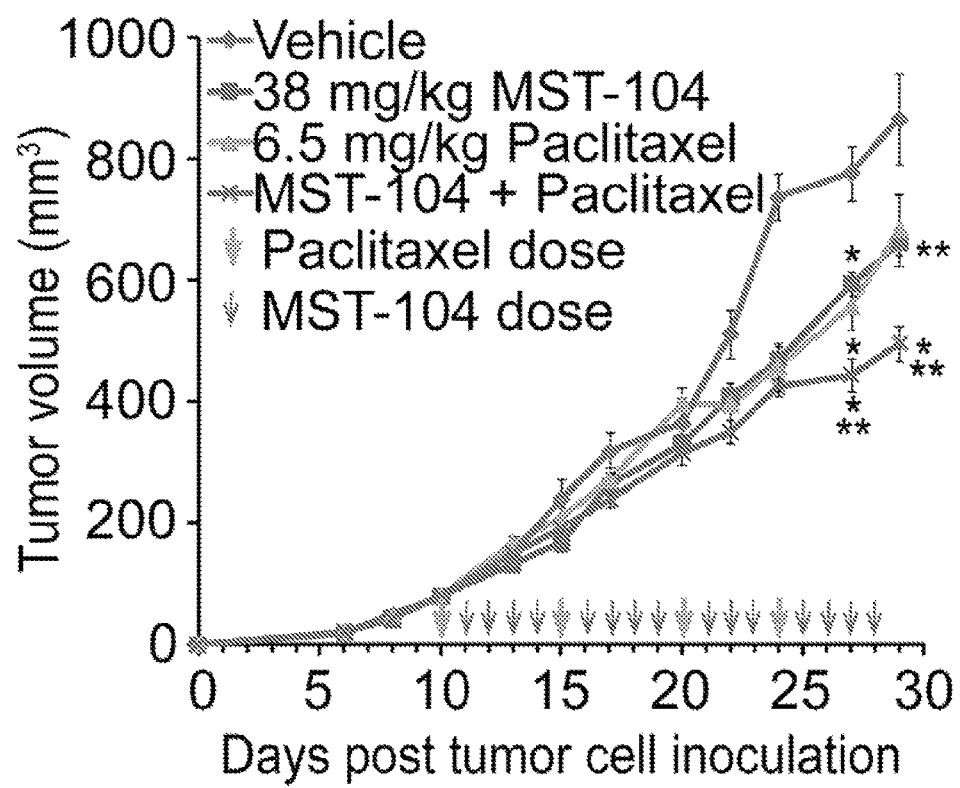
FIG. 26 shows a graphical representation of in vivo tumor growth. MDA-MB-231 LM2-4 Luc+ cells were implanted into NOD/SCID mice, tumors were established for 10 days and treatment was then initiated. Paclitaxel was administered by i.v. injection and MST-104 was provided by i.p. injection according to the dosing schedule outlined in the graph (arrows). n=7-8/group. *P<0.02, **P<0.002.
Figure 27:
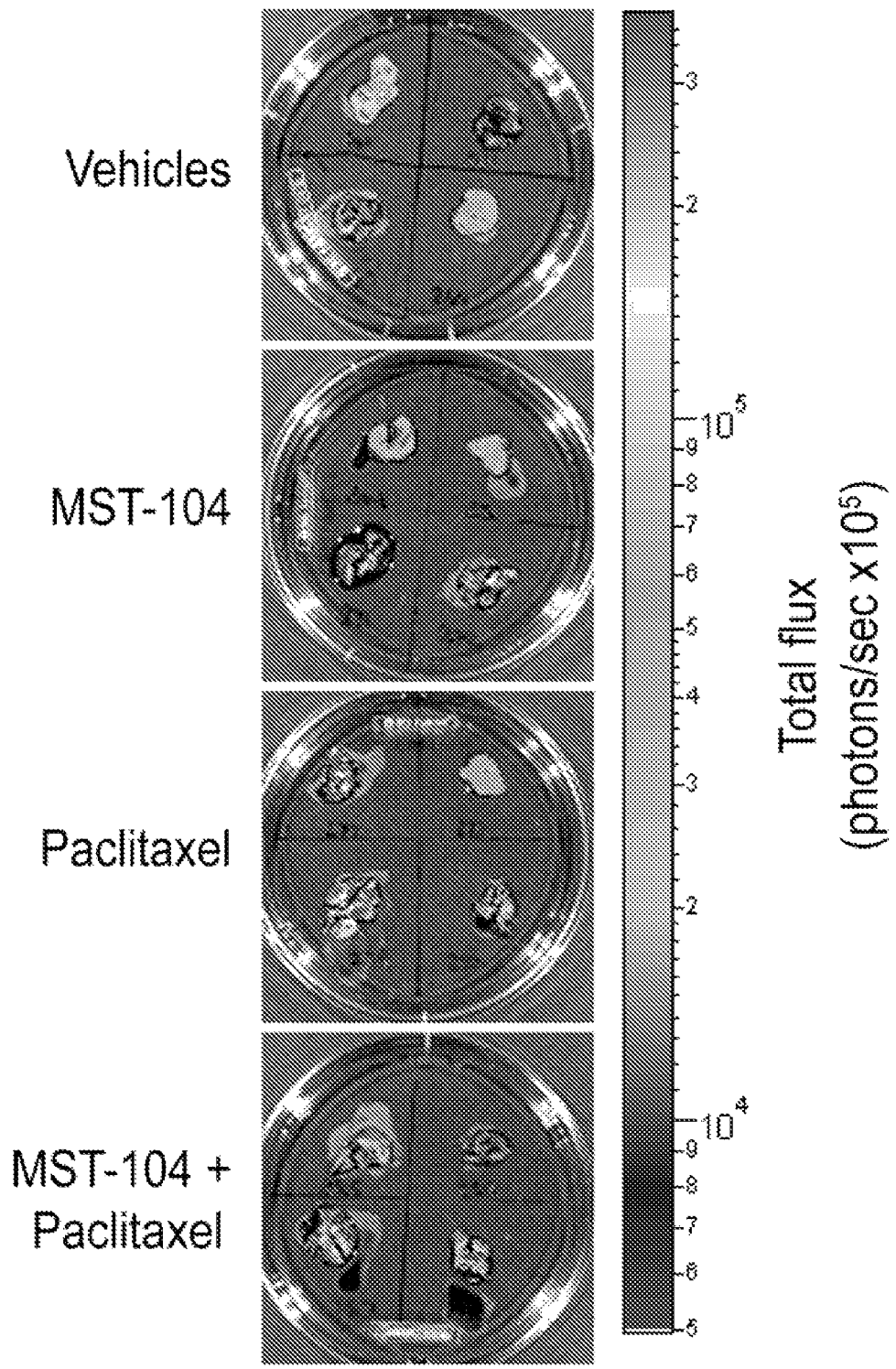
FIG. 27 shows images of lungs resected from mice harboring human breast tumors and subjected to analysis for lung metastases by IVIS ex vivo. Heat maps indicating metastases are overlaid on grayscale images of the lungs.
Figure 28:
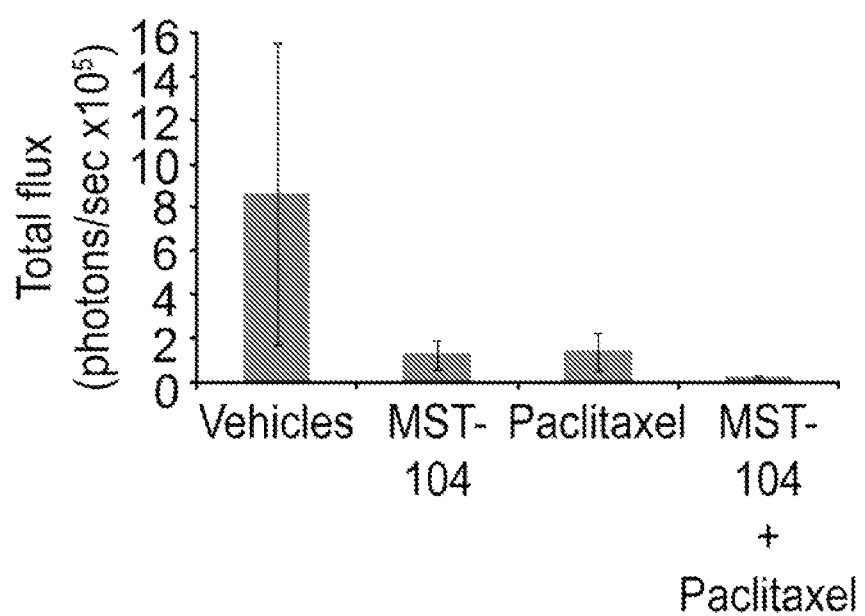
FIG. 28 shows a graphical representation of quantitation of spontaneous lung metastases from mice bearing human orthotopic breast tumors and treated MST-104, in combination with the conventional chemotherapeutic, Paclitaxel. The mean total photon flux±SEM for each group is shown.
Figures 29A, 29B:
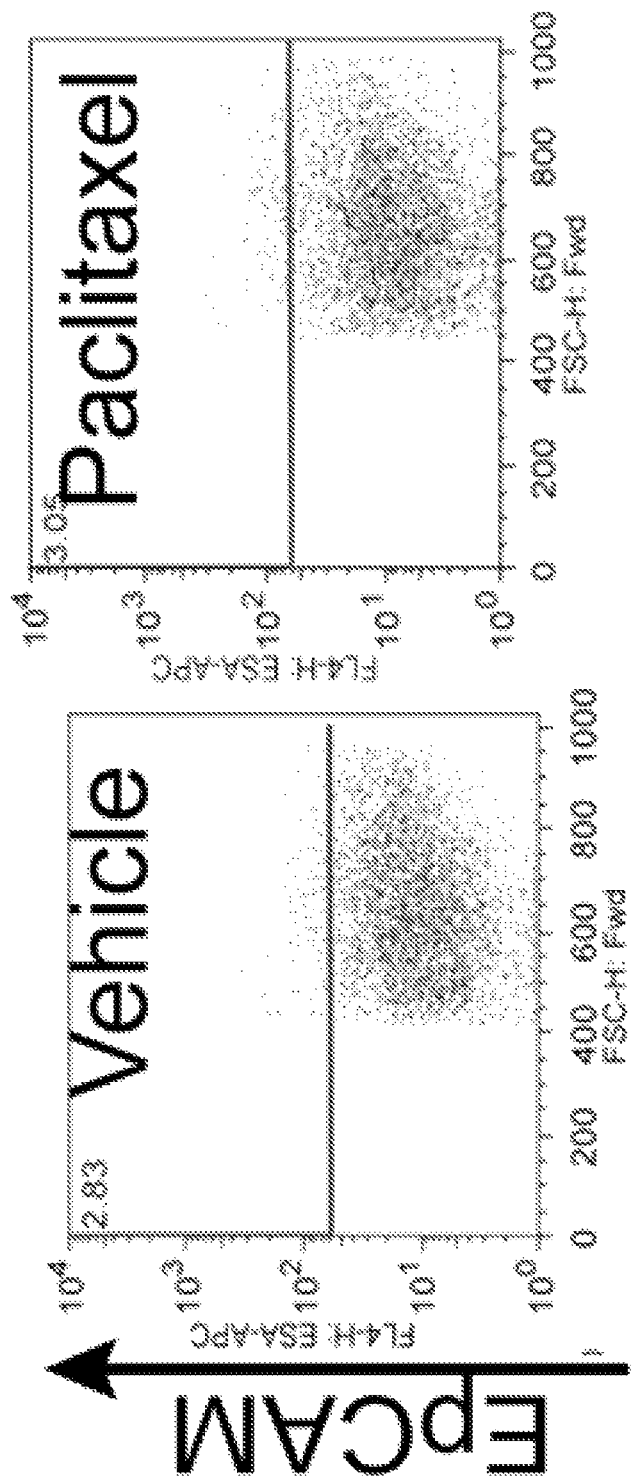
Figure 29E:
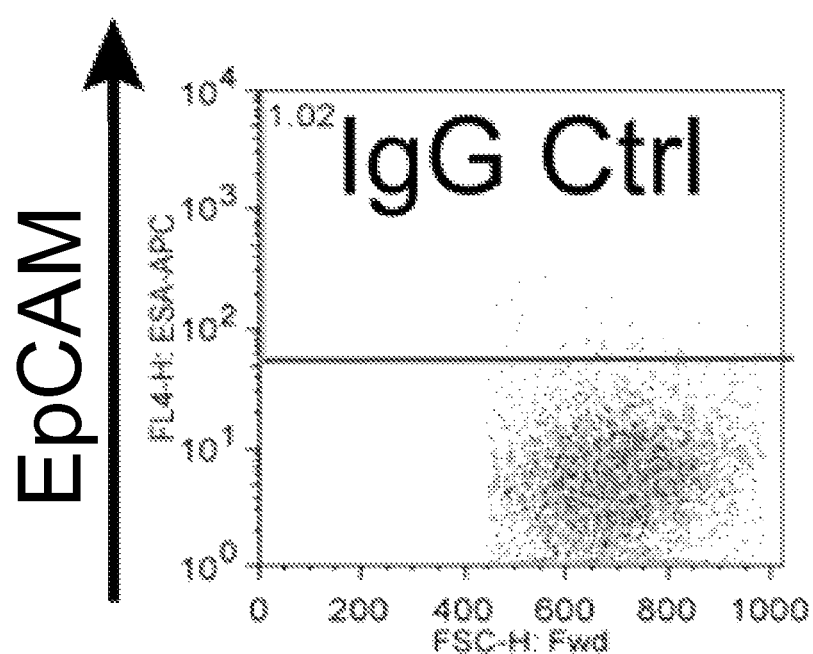
Figure 30:
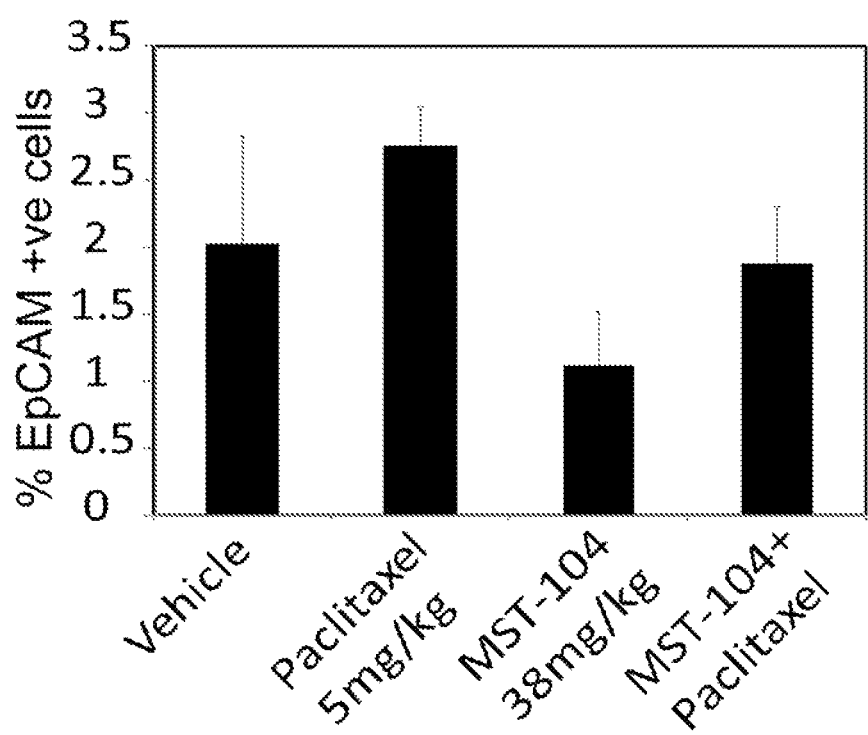
FIG. 30 shows graphical representations of FACS analysis of NOD-SCID mice mammary fat pad inoculated with MDA-MB-231 LM2-4 breast cancer cells, dosed i.v. with Paclitaxel, or MST-104, or both drugs in combination, or vehicle. At the humane end point, tumours were excised and the viable EpCAM positive population was assessed by FACS. Bar chart shows the mean±SEM from three tumors per group.

Paclitaxel is a potent mitotic inhibitor which targets rapidly dividing tumor cells and is the current chemotherapeutic drug of choice for standard breast cancer therapy. The efficacy of CAIX-specific inhibitor treatment with and without paclitaxel treatment on tumor bearing mice was investigated (Lock, McDonald et al. 2012). Sample results description: NOD-SCID mice mammary fat pad were inoculated with LM24 breast cancer cells. After 10 days, mice were dosed with Paclitaxel, or MST-104, or both drugs in combination, or vehicle. Tumor volume was assessed by caliper measurement (FIG. 26) and IVIS imaging of lung metastases are shown in FIG. 27. CAIX inhibitor treatment combined with Paclitaxel suppressed LM 2-4 tumor growth and metastasis in NOD-SCID mice (FIG. 26-28). At the humane end point, tumors were excised and the viable EpCAM positive population was assessed by FACS (FIGS. 29A-29E). As shown in FIG. 30, paclitaxel treatment alone resulted in an increase in the mean percentage of EpCAM+ CSC, compared to vehicle controls. MST-104 treatment alone resulted in a significant decrease on the EpCAM+ population. Importantly, MST-104 treatment, in combination with paclitaxel, rescued the EpCAM+ population back to similar levels as seen with vehicle treated mice (FIG. 30). These data demonstrate the clinical potential of CAIX-specific inhibition on regulation tumor size and CSC population.

Example 8

Figure 31:
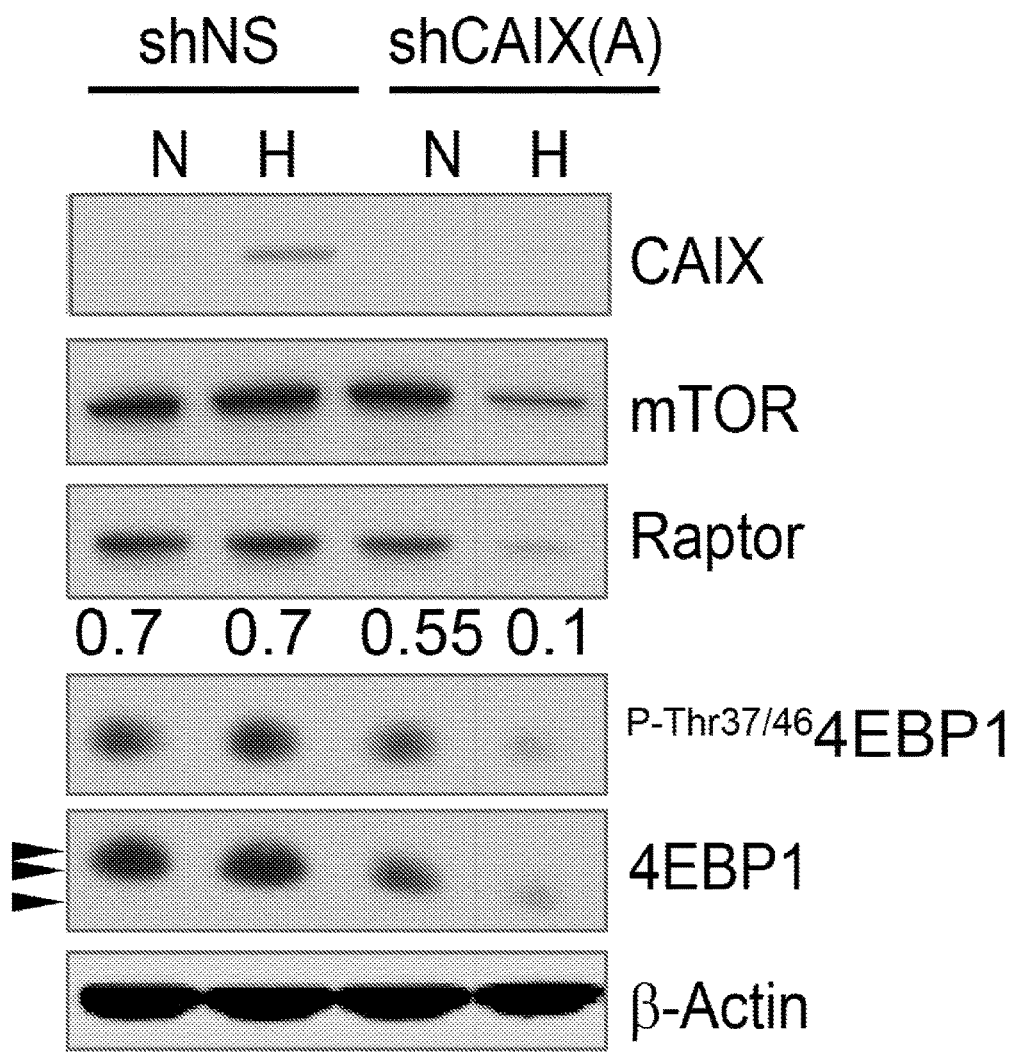
FIG. 31 shows western blots demonstrating the protein levels of several components of the mTOR pathway expressed by 4T1-shNS and 4T1-shCAIX cells cultured as TSs in normoxia (N) or hypoxia (H). Raptor/Actin densitometry values are shown under Raptor immunoblot. Levels of expression of Actin are shown as a loading control.

Depletion of CAIX Expression or Inhibition of CAIX Activity Inhibits the mTOR Pathway mTORC1 signaling was assessed in 4T1 TS lysates cultured in normoxia and hypoxia (Lock, McDonald et al. 2012) (FIG. 31). Depletion of CAIX in hypoxia reduced the expression of mTORC1 components mTOR and Raptor and inhibited downstream signaling to the translation regulator 4EBP1 (FIG. 31), resulting in decreased 4EBP1 phosphorylation and increased mobility (arrowed) (FIG. 31). These data demonstrate that mTOR and its downstream effectors are dependent on CAIX expression in hypoxia. Similar results were observed following CAIX inhibition in parental 4T1 TSs cultured in hypoxia with a CAIX inhibitor (FIG. 32), demonstrating that components of the mTOR pathway can be used as biomarkers of the response to inhibition of CAIX function by cancer cells.

Figure 32:
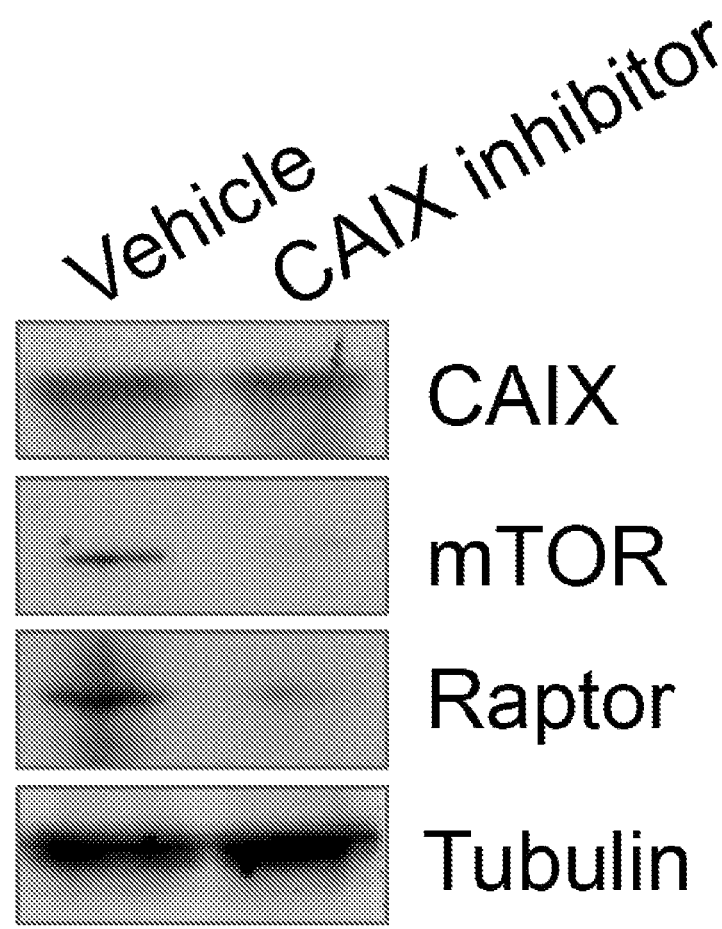
FIG. 32 shows western blots demonstrating the protein levels of mTOR and Raptor expressed by parental 4T1 cells cultured as TSs in hypoxia and treated with a CAIX inhibitor for 7 days. The expression of Tubulin is shown as a loading control.
Figure 33:
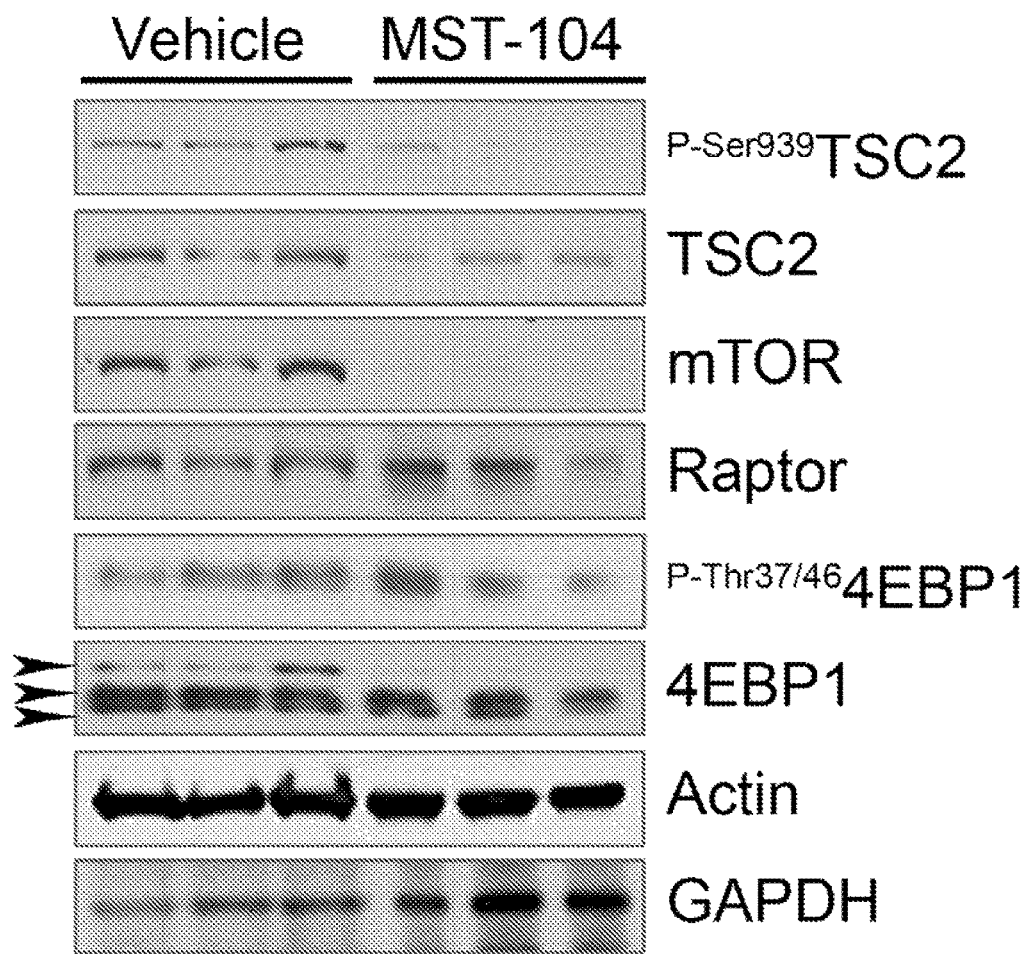
FIG. 33 shows western blots demonstrating the protein levels of several mTOR pathway components expressed by MDA-MB-231 LM2-4Luc$^+$ human breast cancer cells isolated from tumor-bearing mice treated with vehicle or MST-104. Levels of expression of Actin and GAPDH are shown as loading controls.

To assess the effect of inhibition of CAIX activity on the mTOR pathway by breast cancer cells in vivo, orthotopic human primary breast tumors using MDA-MB-231 LM2-4Luc$^+$ cells were established in NOD/SCID mice and treated tumor-bearing animals with vehicle or the CAIX-specific inhibitor MST-104. At the experimental end point, primary tumors were removed, dissociated and viable tumor cells lysed and subjected to Western blotting (Lock, McDonald et al. 2012). Attenuation of CAIX activity in vivo resulted in inhibition of the mTORC1 signaling pathway (FIG. 33), similar to CAIX depletion and inhibition in vitro (FIGS. 31 and 32). CAIX inhibition reduced phosphorylation of $^{Ser939}$TSC2, inhibiting mTORC1 signaling (FIG. 33). Raptor expression was not regulated following CAIX inhibition in vivo (Raptor/Actin densitometry: Vehicle 0.64 mean±0.05 SEM; U-104 mean 0.69±0.14 SEM). However, expression of the mTORC1 component mTOR was abolished, resulting in depleted phosphorylation and expression of the downstream translation regulator 4EBP1 (FIG. 33). These results indicate that CAIX activity is required for mTOR signaling in tumor cells in vivo and demonstrate that components of the mTOR pathway are biomarkers of the response to CAIX-targeted therapy in vivo.

Example 9

Figure 34:
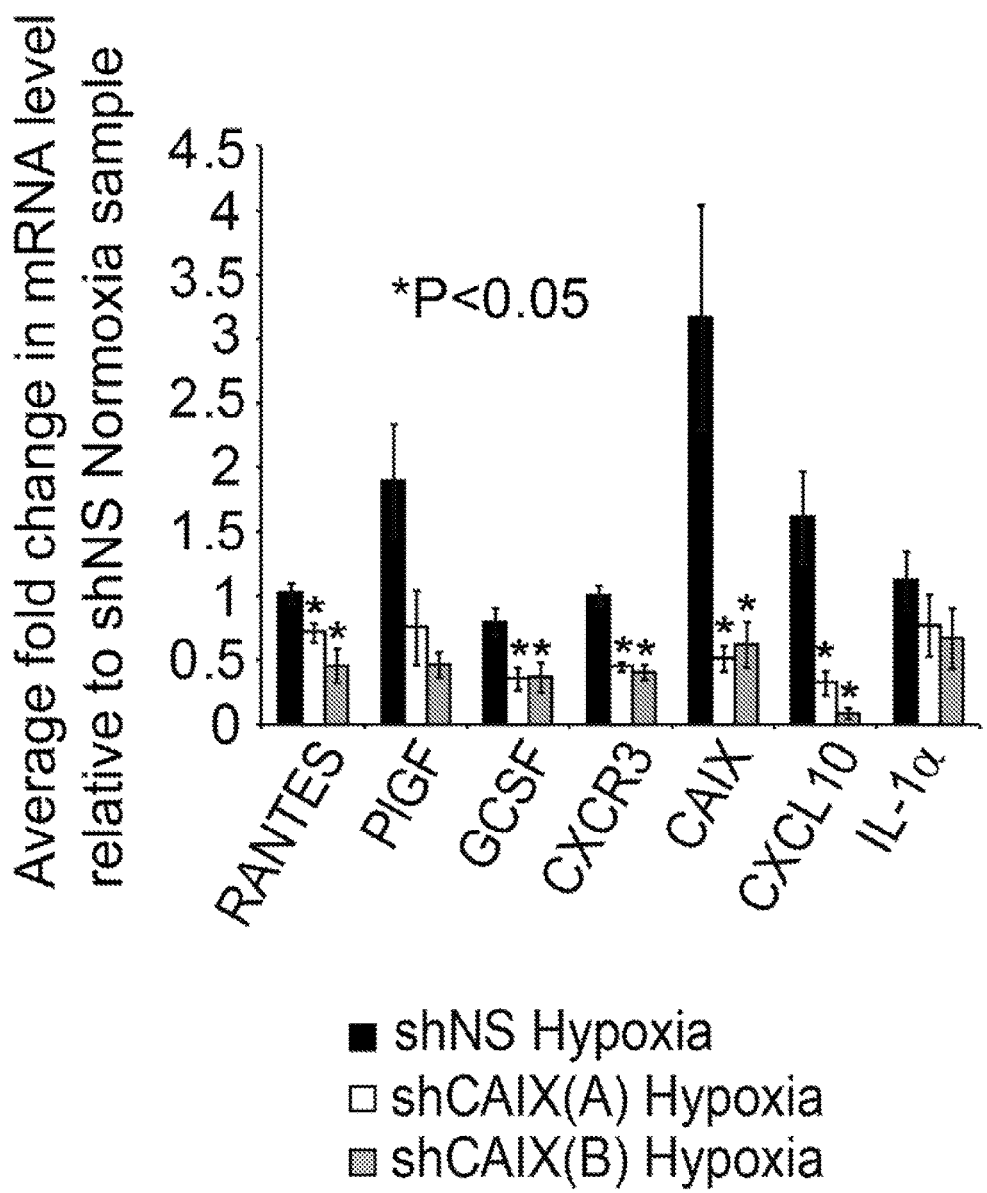
FIG. 34 shows a graph demonstrating the effect of CAIX depletion on the mRNA levels of several chemokine genes by quantitative real-time PCR. 4T1-shNS, 4T1-shCAIX(A) and 4T1-shCAIX(B) cells were cultured in normoxia and hypoxia for 24 h. Cells were harvested, mRNA was extracted, and cDNA was prepared and analyzed by qPCR. The mean fold change±SEM of three independent experiments is shown. Statistical significance was confirmed by T-test, *P<0.05.
Figure 35:
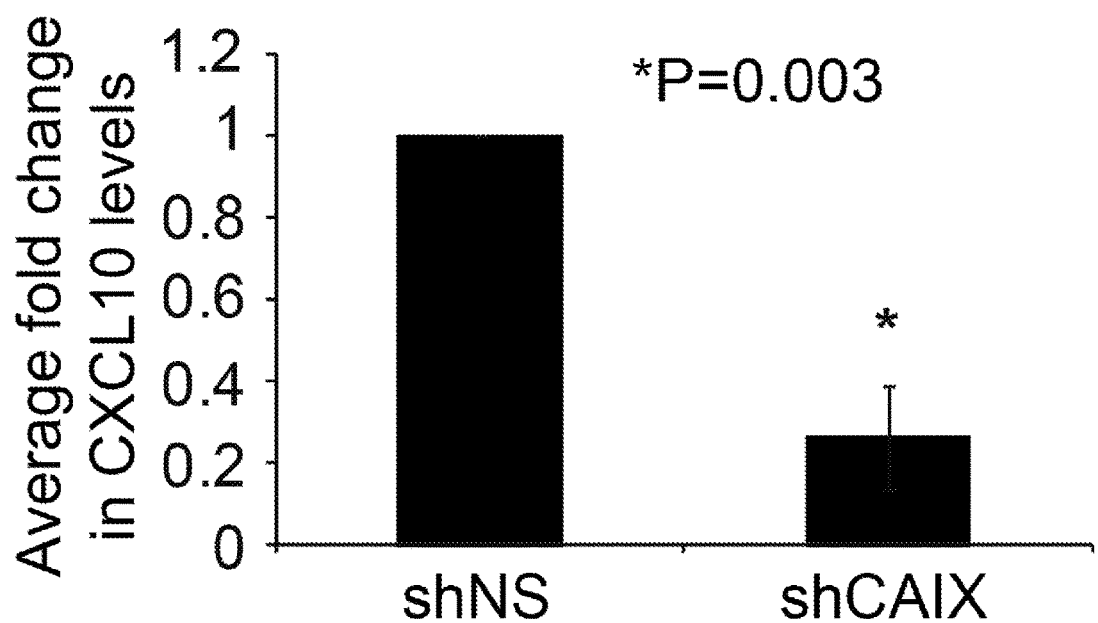
FIG. 35 shows a graphical representation of ELISA data quantifying the amount of mouse CXCL10 present in conditioned media recovered from 4T1-shNS and 4T1-shCAIX cells incubated in hypoxia for 24 h in serum-free growth media. The mean fold change±SEM of three independent experiments is shown. Statistical significance was confirmed by T-test, P=0.003.
Figure 36:
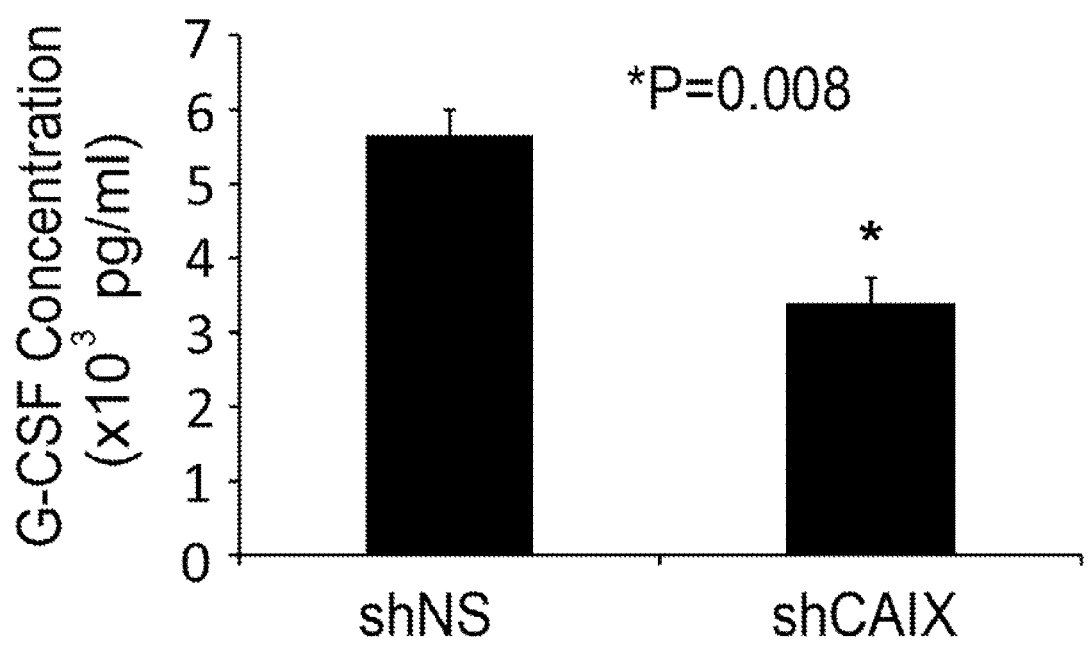
FIG. 36 shows a graphical representation of ELISA data quantifying the levels of mouse G-CSF present in conditioned media recovered from 4T1-shNS and 4T1-shCAIX cells incubated in hypoxia for 24 h in serum-free growth media. The mean concentration±SEM of three independent experiments is shown. Statistical significance was confirmed by T-test, P=0.008.

CAIX is Required for the Secretion of Several Chemokines by Cancer Cells in Hypdxia Using the well established 4T1 model of breast cancer, depletion of CAIX has been shown to block metastasis and ultimately leads to regression of the tumour volume (Lou, McDonald et al. 2011). Analysis of the mRNA levels from 4T1 shNS and shCAIX cells grown in normoxia and hypoxia revealed that the shRNA sequences targeting CAIX are very effective at reducing the CAIX message (FIG. 34), which substantiates previous analysis at the protein level (Lou, McDonald et al. 2011). Depletion of CAIX resulted in a significant reduction in the mRNA levels of several chemokines produced by tumor cells and involved in metastasis (Yu, Kortylewski et al. 2007), including regulated and normal T cell expressed and secreted (RANTES), granulocyte colony stimulating factor (G-CSF), CXC chemokine receptor 3 (CXCR3), and CXCL10 (FIG. 34). The silencing of CAIX also resulted in a reduction in the mRNA level of placental growth factor (PlGF). Furthermore, the decrease in CAIX levels did not lead to a reduction in IL-1α message demonstrating that the effect on the above chemokines is specific. The reduction of G-CSF and CXCL10 mRNA levels was further validated at the protein level by ELISA (FIGS. 35 and 36). Both CXCL10 (FIG. 35) and G-CSF (FIG. 36) protein levels in conditioned media isolated from 4T1 shCAIX cells grown in hypoxia were significantly lower than the non-silencing control cells cultured in the same conditions. These data suggest that CAIX expression by cancer cells in hypoxia influences the pool of secreted factors available to the tumor microenvironment, and these factors are biomarkers of the response to the inhibition of CAIX expression and/or activity by cancer cells.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

REFERENCES

1. Lou Y, Preobrazhenska O, auf dem Keller U, Sutcliffe M, Barclay L, McDonald P C, Roskelley C, Overall C M, Dedhar S. Epithelial-mesenchymal transition (EMT) is not sufficient for spontaneous murine breast cancer metastasis. Dev Dyn 2008; 237:2755-68.
2. Ebos J M, Lee C R, Cruz-Munoz W, Bjarnason G A, Christensen J G, Kerbel R S. Accelerated metastasis after short-term treatment with a potent inhibitor of tumor angiogenesis. Cancer Cell 2009; 15:232-9.
3. Lou Y, McDonald P C, Oloumi A, Chia S, Ostlund C, Ahmadi A, Kyle A, Auf dem Keller U, Leung S, Huntsman D, Clarke B, Sutherland B W, Waterhouse D, Bally M, Roskelley C, Overall C M, Minchinton A, Pacchiano F, Carta F, Scozzafava A, Touisni N, Winum J Y, Supuran C T, Dedhar S. Targeting Tumor Hypoxia: Suppression of Breast Tumor Growth and Metastasis by Novel Carbonic Anhydrase IX Inhibitors. Cancer Res 2011; 71:3364-76.
4. Lock F E, McDonald P C, Lou Y, Serrano I, Chafe S C, Ostlund C, Aparicio S, Winum J-Y, Supuran C T, Dedhar S. Targeting Carbonic anhydrase IX depletes breast cancer stem cells within the hypoxic niche. Oncogene 2012: in press.
5. Oloumi A, MacPhail S H, Johnston P J, Banath J P, Olive P L. Changes in subcellular distribution of topoisomerase IIalpha correlate with etoposide resistance in multicell spheroids and xenograft tumors. Cancer Res 2000; 60:5747-53.
6. Turner F E, Broad S, Khanim F L, Jeanes A, Talma S, Hughes S, Tselepis C, Hotchin N A. Slug regulates integrin expression and cell proliferation in human epidermal keratinocytes. J Biol Chem 2006; 281:21321-31.
7. Lock F E, Hotchin N A. Distinct roles for ROCK1 and ROCK2 in the regulation of keratinocyte differentiation. PLoS One 2009; 4:e8190.
8. Livak K J, Schmittgen T D. Analysis of relative gene expression data using real-time quantitative PCR and the 2(-Delta Delta C(T)) Method. Methods 2001; 25:402-8.
9. Supuran C T. Carbonic anhydrases: novel therapeutic applications for inhibitors and activators. Nat Rev Drug Discov 2008; 7:168-81.
10. Rebollo R, Miceli-Royer K, Zhang Y, Farivar S, Gagnier L, Mager D L. Epigenetic interplay between mouse endogenous retroviruses and host genes. Genome biology 2012; 13:R89.
11. Ponti D, Costa A, Zaffaroni N, Pratesi G, Petrangolini G, Coradini D, Pilotti S, Pierotti M A, Daidone M G. Isolation and in vitro propagation of tumorigenic breast cancer cells with stem/progenitor cell properties. Cancer Res 2005; 65:5506-11.
12. Yip N C, Fombon I S, Liu P, Brown S, Kannappan V, Armesilla A L, Xu B, Cassidy J, Darling J L, Wang W. Disulfuram modulated ROS-MAPK and NFkappaB pathways and targeted breast cancer cells with cancer stem cell-like properties. Br J Cancer 2011; 104:1564-74.
13. Stingl J, Eaves C J, Zandieh I, Emerman J T. Characterization of bipotent mammary epithelial progenitor cells in normal adult human breast tissue. Breast Cancer Res Treat 2001; 67:93-109.
14. Dontu G, Abdallah W M, Foley J M, Jackson K W, Clarke M F, Kawamura M J, Wicha M S. In vitro propagation and transcriptional profiling of human mammary stem/progenitor cells. Genes Dev 2003; 17:1253-70.
15. Al-Hajj M, Wicha M S, Benito-Hernandez A, Morrison S J, Clarke M F. Prospective identification of tumorigenic breast cancer cells. Proc Natl Acad Sci USA 2003; 100: 3983-8.
16. Reuben J M, Lee B N, Gao H, Cohen E N, Mego M, Giordano A, Wang X, Lodhi A, Krishnamurthy S, Hortobagyi G N, Cristofanilli M, Lucci A, Woodward W A. Primary breast cancer patients with high risk clinicopathologic features have high percentages of bone marrow epithelial cells with ALDH activity and CD44(+) CD24(lo) cancer stem cell phenotype. Eur J Cancer 2011.
17. Cano A, Perez-Moreno M A, Rodrigo I, Locascio A, Blanco M J, del Barrio M G, Portillo F, Nieto M A. The transcription factor snail controls epithelial-mesenchymal transitions by repressing E-cadherin expression. Nat Cell Biol 2000; 2:76-83.
18. Yook J I, Li X Y, Ota I, Fearon E R, Weiss S J. Wnt-dependent regulation of the E-cadherin repressor snail. J Biol Chem 2005; 280:11740-8.
19. Malizia A P, Lacey N, Walls D, Egan J J, Doran P P. CUX1/Wnt signaling regulates epithelial mesenchymal transition in EBV infected epithelial cells. Exp Cell Res 2009; 315:1819-31.
20. Hartwell K A, Muir B, Reinhardt F, Carpenter A E, Sgroi D C, Weinberg R A. The Spemann organizer gene, Goosecoid, promotes tumor metastasis. Proc Natl Acad Sci USA 2006; 103:18969-74.
21. Vandewalle C, Van Roy F, Berx G. The role of the ZEB family of transcription factors in development and disease. Cell Mol Life Sci 2009; 66:773-87.
22. Mani S A, Yang J, Brooks M, Schwaninger G, Zhou A, Miura N, Kutok J L, Hartwell K, Richardson A L, Weinberg R A. Mesenchyme Forkhead 1 (FOXC2) plays a key role in metastasis and is associated with aggressive basal-like breast cancers. Proc Natl Acad Sci USA 2007; 104:10069-74.

23. Pacchiano F, Carta F, McDonald P C, Lou Y, Vullo D, Scozzafava A, Dedhar S, Supuran C T. Ureido-substituted benzenesulfonamides potently inhibit carbonic anhydrase IX and show antimetastatic activity in a model of breast cancer metastasis. J Med Chem 2011; 54:1896-902.

24. Hwang-Verslues W W, Kuo W H, Chang P H, Pan C C, Wang H H, Tsai S T, Jeng Y M, Shew J Y, Kung J T, Chen C H, Lee E Y, Chang K J, Lee W H. Multiple lineages of human breast cancer stem/progenitor cells identified by profiling with stem cell markers. PLoS One 2009; 4:e8377.

25. Yu H, Kortylewski M, Pardoll D. Crosstalk between cancer and immune cells: role of STAT3 in the tumour microenvironment. Nature reviews Immunology 2007; 7:41-51.

The invention claimed is:

1. A method for treating cancer in a human patient, comprising:
   (A) isolating a cancer sample from a human patient,
   (B) performing an assay to detect the presence of cancer stem cells in the cancer sample, comprising:
      (a) measuring gene transcription level(s), protein expression level(s), protein modification level(s), or a combination thereof of at least six markers in the cancer sample, wherein the at least six markers are:
         (1) a cancer stem cell marker that is CAIX,
         (2) a mesenchymal marker that is smooth muscle actin,
         (3) an epithelial marker that is E-cadherin,
         (4) a stemness marker that is Notch 1,
         (5) an mTORC1 marker that is mTOR, and
         (6) a chemokine marker that is Granulocyte-Colony Stimulating Factor (G-CSF);
      (b) comparing the level of each of the at least six markers measured in step (a) with a reference level for each of the at least six markers measured in normal or non-tumorigenic cancer cells from the same tissue origin as the cancer sample;
      (c) identifying the cancer sample as containing cancer stem cells if based on the comparing of step (b), an increase in the levels of the cancer stem cell marker, the mesenchymal marker, the stemness marker, the mTORC1 marker, and the chemokine marker and a decrease in the level of the epithelial marker are detected in the cancer sample; and
   (B) administering to the human patient an effective amount of a carbonic anhydrase IX (CAIX) inhibitor.

2. The method of claim 1, wherein the CAIX inhibitor is one of the compounds having the following structures:

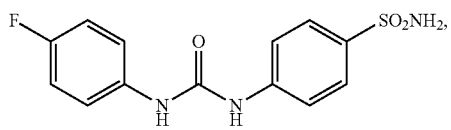 [SMILES: NS(=O)(=O)c1ccc(NC(=O)Nc2ccc(F)cc2)cc1]

and

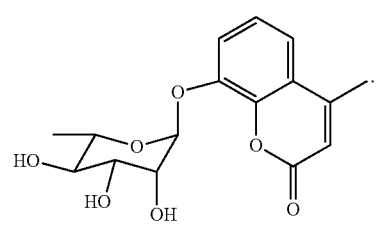

MST-205

3. The method of claim 1, further comprising administering an effective amount of an antiangiogenic agent or a chemotherapeutic agent to the patient.

4. The method of claim 3, wherein the chemotherapeutic agent is taxane.

5. The method of claim 1, wherein step (a) comprises measuring the protein modification level(s) of one or more of the at least six markers.

6. The method of claim 1, wherein step (a) comprises measuring the gene transcription level(s) of one or more of the at least six markers.

7. The method of claim 1, wherein step (a) comprises measuring the protein expression level(s) of one or more of the at least six markers.

8. The method of claim 7, wherein step (a) comprises measuring the level of the chemokine marker secreted by the cells of the cancer sample.

9. The method of claim 5, wherein step (a) comprises measuring the phosphorylation level of one or more of the at least six markers.

10. The method of claim 1, wherein the cancer stem cells are breast cancer stem cells, brain cancer stem cells, colon cancer stem cells, ovarian cancer stem cells, pancreas cancer stem cells, prostate cancer stem cells, melanoma stem cells, or multiple myeloma stem cells.

11. The method of claim 1, wherein the sample is from a cancer patient after a prior cancer treatment.

12. The method of claim 1, wherein step (a) further comprises measuring gene transcription level(s), protein expression level(s), protein modification level(s), or a combination thereof of one or more of additional cancer stem cell markers selected from Epithelial Cell Adhesion Molecule (EpCAM), Aldehyde dehydrogenase 1 family member A3 (ALDH1A3), CD44, and CD133, and
   step (b) further comprises comparing the level of each of the one or more of additional cancer stem cell markers measured in step (a) with a reference level for each of the one or more additional cancer stem cell markers measured in normal or non-tumorigenic cancer cells from the same tissue origin as the cancer sample.

13. The method of claim 12, wherein the additional cancer stem cell markers are selected from Epithelial Cell Adhesion Molecule (EpCAM), CD44, and CD133.

14. The method of claim 1, wherein step (a) further comprises measuring gene transcription level(s), protein expression level(s), protein modification level(s), or a combination thereof of one or more of additional mesenchymal markers selected from zinc finger protein SNA1 (Snail)-1, Snail-2, Wingless-Type MMTV Integration Site Family Member 5B (Wnt5B), Goosecoid, Zinc Finger E-box Binding Homeobox 2 (Zeb2), Forkhead Box Protein C2 (FoxC2), vimentin, and p23, and
   step (b) further comprises comparing the level of each of the one or more additional mesenchymal markers measured in step (a) with a reference level for each of the one or more additional mesenchymal markers measured in normal or non-tumorigenic cancer cells from the same tissue origin as the cancer sample.

15. The method of claim 14, wherein the additional mesenchymal markers are selected from zinc finger protein SNA1 (Snail)-1, Snail-2, and vimentin.

16. The method of claim 1, wherein step (a) further comprises measuring gene transcription level(s), protein expression level(s), protein modification level(s), or a combination thereof of one or more of additional epithelial markers selected from cytokeratin and Desmoplakin, and
step (b) further comprises comparing the level of each of the one or more of additional epithelial markers measured in step (a) with a reference level for each of the one or more additional epithelial markers measured in normal or non-tumorigenic cancer cells from the same tissue origin as the cancer sample.

17. The method of claim 16, wherein the one or more of additional epithelial markers is cytokeratin.

18. The method of claim 1, wherein step (a) further comprises measuring the gene transcription level, the protein expression level, the protein modification level, or a combination thereof of an additional stemness marker that is Jagged 1, and
step (b) further comprises comparing the level of the additional stemness marker measured in step (a) with a reference level for the additional stemness marker measured in normal or non-tumorigenic cancer cells from the same tissue origin as the cancer sample.

19. The method of claim 1, wherein step (a) further comprises measuring gene transcription level(s), protein expression level(s), protein modification level(s), or a combination thereof of one or more of additional mTORC1 markers selected from Regulatory-Associated Protein of mTOR (Raptor), eIf4E-Binding Protein 1 (4EBP1), and Tuberous Sclerosis Complex 2 (TSC2), and
step (b) further comprises comparing the level of each of the one or more of additional mTORC1 markers measured in step (a) with a reference level for each of the one or more additional mTORC1 markers measured in normal or non-tumorigenic cancer cells from the same tissue origin as the cancer sample.

20. The method of claim 19, wherein the one or more of additional mTORC1 markers are selected from Raptor and 4EBP1.

21. The method of claim 1, wherein step (a) further comprises measuring gene transcription level(s), protein expression level(s), protein modification level(s), or a combination thereof of one or more of additional chemokine markers selected from Activation Normal T Expressed and Secreted (RANTES), Phosphatidylinositol-Glycan Biosyntheses Class F Protein (PIGF), C-X-C Motif Chemokine 3 (CXCR3), and C-X-C Motif Chemokine 10 (CXCL10), and
step (b) further comprises comparing the level of each of the one or more of additional chemokine markers measured in step (a) with a reference level for each of the one or more additional chemokine markers measured in normal or non-tumorigenic cancer cells from the same tissue origin as the cancer sample.

22. The method of claim 21, wherein the additional chemokine markers are selected from Activation Normal T Expressed and Secreted (RANTES), Phosphatidylinositol-Glycan Biosyntheses Class F Protein (PIGF), and C-X-C Motif Chemokine 10 (CXCL10).

23. The method claim 1, wherein step (a) further comprises measuring gene transcription level(s), protein expression level(s), protein modification level(s), or a combination thereof of:
one or more additional cancer stem cell markers selected from Epithelial Cell Adhesion Molecule (EpCAM), CD44, and CD133,
one or more additional mesenchymal markers selected from zinc finger protein SNA1 (Snail)-1, Snail-2, and vimentin,
an additional epithelial marker that is cytokeratin,
an additional stemness marker that is Jagged-1,
one or more additional mTORC1 markers selected from Raptor and 4EBP1, and
one or more additional chemokine markers selected from Activation Normal T Expressed and Secreted (RANTES), Phosphatidylinositol-Glycan Biosyntheses Class F Protein (PIGF), and C-X-C Motif Chemokine 10 (CXCL10); and
step (b) further comprises comparing the level of each of the one or more of additional chemokine markers, the one or more additional mesenchymal markers, the additional epithelial marker, the additional stemness marker, the one or more additional mTORC1 markers, and the one or more additional chemokine markers measured in step (a) with a reference level for each of the one or more additional chemokine markers, the one or more additional mesenchymal markers, the additional epithelial marker, the additional stemness marker, the one or more additional mTORC1 markers, and the one or more additional chemokine markers measured in normal or non-tumorigenic cancer cells from the same tissue origin as the cancer sample.

* * * * *

UNITED STATES PATENT AND TRADEMARK OFFICE
CERTIFICATE OF CORRECTION

Page 1 of 1

PATENT NO. : 10,195,174 B2
APPLICATION NO. : 14/353665
DATED : February 5, 2019
INVENTOR(S) : Paul C. McDonald It is certified that error appears in the above-identified patent and that said Letters Patent is hereby corrected as shown below:

On the Title Page

<u>Item (71)</u>:
"British Columbia Cancer Agency, Vancouver (CA)" should read, "British Columbia Cancer Agency Branch, Vancouver (CA)--.

Signed and Sealed this
First Day of October, 2019

Andrei Iancu
*Director of the United States Patent and Trademark Office*